(12) United States Patent
Chandraratna et al.

(10) Patent No.: US 11,517,549 B2
(45) Date of Patent: *Dec. 6, 2022

(54) TREATMENT OF DISEASE WITH ESTERS OF SELECTIVE RXR AGONISTS

(71) Applicant: Io Therapeutics, Inc., Santa Ana, CA (US)

(72) Inventors: Roshantha A. Chandraratna, San Juan Capistrano, CA (US); Martin E. Sanders, Seattle, WA (US)

(73) Assignee: Io Therapeutics, Inc., Spring, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/137,167

(22) Filed: Sep. 20, 2018

(65) Prior Publication Data

US 2019/0083441 A1 Mar. 21, 2019

Related U.S. Application Data

(60) Provisional application No. 62/560,776, filed on Sep. 20, 2017.

(51) Int. Cl.
| | | |
|---|---|---|
| *A61K 31/216* | (2006.01) | |
| *A61P 35/00* | (2006.01) | |
| *A61P 25/16* | (2006.01) | |
| *A61P 25/28* | (2006.01) | |
| *A61P 21/00* | (2006.01) | |
| *A61K 45/06* | (2006.01) | |
| *A61P 37/02* | (2006.01) | |
| *A61K 31/198* | (2006.01) | |
| *A61K 9/00* | (2006.01) | |

(52) U.S. Cl.
CPC .......... *A61K 31/216* (2013.01); *A61K 31/198* (2013.01); *A61K 45/06* (2013.01); *A61P 21/00* (2018.01); *A61P 25/16* (2018.01); *A61P 25/28* (2018.01); *A61P 35/00* (2018.01); *A61P 37/02* (2018.01); *A61K 9/0043* (2013.01); *A61K 9/0053* (2013.01)

(58) Field of Classification Search
CPC .... A61K 31/216; A61K 31/198; A61K 45/06; A61K 9/0043; A61P 21/00; A61P 37/02; A61P 25/28; A61P 25/16; A61P 35/00
See application file for complete search history.

(56) References Cited

U.S. PATENT DOCUMENTS

| | | | |
|---|---|---|---|
| 4,756,911 A | 7/1988 | Drost | |
| 5,378,475 A | 1/1995 | Smith | |
| 5,455,265 A | 10/1995 | Chandraratna | |
| 5,466,861 A | 11/1995 | Dawson et al. | |
| 5,663,367 A | 9/1997 | Vuligonda et al. | |
| 5,675,033 A | 10/1997 | Vuligonda et al. | |
| 5,728,846 A | 3/1998 | Vuligonda et al. | |
| 5,739,338 A | 4/1998 | Beard et al. | |
| 5,763,635 A | 6/1998 | Vuligonda et al. | |
| 5,773,594 A | 6/1998 | Johnson et al. | |
| 5,776,699 A | 7/1998 | Klein et al. | |
| 5,780,647 A | 7/1998 | Vuligonda et al. | |
| 5,817,836 A | 10/1998 | Vuligonda et al. | |
| 5,856,490 A | 1/1999 | Teng | |
| 5,877,207 A | 3/1999 | Klein et al. | |
| 5,917,082 A * | 6/1999 | Vuligonda ............. A61K 31/20 560/100 |
| 5,919,970 A | 7/1999 | Song et al. | |
| 5,952,345 A | 9/1999 | Klein et al. | |
| 5,958,954 A | 9/1999 | Klein et al. | |
| 5,965,606 A | 10/1999 | Teng | |
| 5,998,655 A | 12/1999 | Vuligonda et al. | |
| 6,008,204 A | 12/1999 | Klein et al. | |
| 6,048,873 A | 1/2000 | Vasudevan et al. | |
| 6,034,242 A | 3/2000 | Vuligonda et al. | |
| 6,037,488 A | 3/2000 | Song et al. | |
| 6,043,381 A | 3/2000 | Vuligonda et al. | |
| 6,063,768 A | 5/2000 | First | |
| 6,087,505 A | 7/2000 | Vuligonda et al. | |
| 6,090,810 A | 7/2000 | Klein et al. | |
| 6,114,533 A | 9/2000 | Vuligonda et al. | |
| 6,117,987 A | 9/2000 | Johnson et al. | |
| 6,147,224 A | 11/2000 | Vuligonda et al. | |
| 6,187,750 B1 | 2/2001 | Chein | |
| 6,211,385 B1 | 4/2001 | Vuligonda et al. | |
| 6,218,128 B1 | 4/2001 | Klein et al. | |
| 6,225,494 B1 | 5/2001 | Song et al. | |
| 6,228,848 B1 | 5/2001 | Klein et al. | |

(Continued)

FOREIGN PATENT DOCUMENTS

| | | |
|---|---|---|
| EP | 2322147 A1 | 5/2011 |
| EP | 2556827 A1 | 2/2013 |

(Continued)

OTHER PUBLICATIONS

Inoue et al., Rexinoids isolated from Sophora tonkinensis with a gene expression profile distinct from the synthetic rexinoid bexarotene. J. Nat. Prod. 77:1670-1677 (2014).

(Continued)

*Primary Examiner* — Sahar Javanmard

(74) *Attorney, Agent, or Firm* — K&L Gates LLP; Louis C. Cullman; Michelle Glasky Bergman

(57) ABSTRACT

The present specification provides methods of treating disease with an ester of an RXR agonist or a combination of an ester of an RXR agonist and a thyroid hormone. The esters of an RXR agonist can be useful in the treatment of cancer, nervous system, autoimmune, and muscular disorders.

23 Claims, 12 Drawing Sheets

(56) References Cited

U.S. PATENT DOCUMENTS

| | | |
|---|---|---|
| 6,235,923 B1 | 5/2001 | Song et al. |
| 6,313,163 B1 | 11/2001 | Vuligonda et al. |
| 6,313,168 B1 | 11/2001 | Pacifici et al. |
| 6,387,950 B2 | 5/2002 | Nehme |
| 6,403,638 B1 | 6/2002 | Vuligonda et al. |
| 6,521,624 B1 | 2/2003 | Klein et al. |
| 6,521,641 B1 | 2/2003 | Klein et al. |
| 6,538,149 B1 | 3/2003 | Vuligonda et al. |
| 6,555,690 B2 | 4/2003 | Johnson et al. |
| 6,610,744 B2 | 8/2003 | Teng et al. |
| 6,630,463 B2 | 10/2003 | Kikuchi et al. |
| 6,653,483 B1 | 11/2003 | Johnson et al. |
| 6,720,423 B2 | 4/2004 | Vasudevan et al. |
| 6,720,425 B2 | 4/2004 | Johnson et al. |
| 6,776,984 B1 | 8/2004 | Schwartz |
| 6,818,775 B2 | 11/2004 | Johnson et al. |
| 6,942,980 B1 | 9/2005 | Klein et al. |
| 7,048,946 B1 | 5/2006 | Wong |
| 7,105,566 B2 | 9/2006 | Chandraratna et al. |
| 7,166,726 B2 | 1/2007 | Vuligonda et al. |
| 8,101,662 B2 | 1/2012 | Chandraratna |
| 9,308,186 B2 | 4/2016 | Chandraratna |
| 9,655,872 B2 | 5/2017 | Chandraratna |
| 9,717,702 B2 | 8/2017 | Chandraratna |
| 10,039,731 B2 | 8/2018 | Chandraratna |
| 10,188,618 B2 | 1/2019 | Chandraratna |
| 10,590,059 B2 | 3/2020 | Chandraratna et al. |
| 10,596,133 B2 | 3/2020 | Chandraratna |
| 10,806,713 B2 | 10/2020 | Chandraratna et al. |
| 10,835,507 B2 | 11/2020 | Chandraratna et al. |
| 10,857,117 B2 | 12/2020 | Chandraratna et al. |
| 10,966,950 B2 | 4/2021 | Sanders et al. |
| 10,973,791 B2 | 4/2021 | Chandraratna et al. |
| 10,980,759 B2 | 4/2021 | Chandraratna et al. |
| 11,065,219 B2 | 7/2021 | Chandraratna et al. |
| 2001/0037025 A1 | 11/2001 | Murray et al. |
| 2002/0156022 A1 | 10/2002 | Edwards et al. |
| 2002/0156054 A1 | 10/2002 | Klein et al. |
| 2002/0173631 A1 | 11/2002 | Johnson et al. |
| 2002/0193403 A1 | 12/2002 | Yuan et al. |
| 2003/0013766 A1 | 1/2003 | Lamph et al. |
| 2003/0077664 A1 | 4/2003 | Zhao et al. |
| 2003/0130341 A1 | 7/2003 | Li et al. |
| 2003/0144330 A1 | 7/2003 | Spiegelman |
| 2003/0219832 A1 | 11/2003 | Klein et al. |
| 2004/0005304 A1 | 1/2004 | Brudnak |
| 2004/0049072 A1 | 3/2004 | Ardecky |
| 2004/0147611 A1 | 7/2004 | Yuan et al. |
| 2004/0037025 A1 | 11/2004 | Murray et al. |
| 2005/0004213 A1 | 1/2005 | Sinha et al. |
| 2005/0171151 A1 | 8/2005 | Yuan et al. |
| 2005/0181017 A1 | 8/2005 | Hughes |
| 2005/0244464 A1 | 11/2005 | Hughes |
| 2006/0286127 A1 | 12/2006 | Van Schaack et al. |
| 2007/0054882 A1 | 3/2007 | Klein et al. |
| 2007/0077652 A1 | 4/2007 | Peled et al. |
| 2007/0078129 A1 | 4/2007 | Lagu et al. |
| 2007/0122476 A1 | 5/2007 | Hanshew |
| 2007/0185055 A1 | 8/2007 | Jiang |
| 2007/0265449 A1 | 11/2007 | Vuligonda et al. |
| 2009/0004291 A1 | 1/2009 | Song |
| 2009/0136470 A1 | 5/2009 | Hilde et al. |
| 2009/0203720 A1* | 8/2009 | Zhao .................. A61K 31/00 514/275 |
| 2009/0209601 A1 | 8/2009 | Nagpal et al. |
| 2009/0227674 A1 | 9/2009 | Richon et al. |
| 2010/0112079 A1 | 5/2010 | Mousa et al. |
| 2010/0298434 A1 | 11/2010 | Rouillard |
| 2011/0008437 A1 | 1/2011 | Mtman |
| 2012/0115912 A1 | 5/2012 | Landreth |
| 2012/0238623 A1 | 9/2012 | Chandraratna |
| 2012/0309833 A1 | 12/2012 | Wagner et al. |
| 2013/0190395 A1 | 7/2013 | Chandraratna et al. |
| 2014/0235676 A1 | 8/2014 | Landreth |
| 2014/0286973 A1 | 9/2014 | Powell, Jr. |
| 2015/0038585 A1* | 2/2015 | Chandraratna ...... A61K 31/192 514/569 |
| 2015/0196517 A1 | 7/2015 | Chandraratna et al. |
| 2015/0342917 A1 | 12/2015 | Chandraratna et al. |
| 2016/0263189 A1* | 9/2016 | Burstein .............. A61K 38/185 |
| 2017/0056348 A1 | 3/2017 | Chandraratna et al. |
| 2017/0119713 A1 | 5/2017 | Chandraratna et al. |
| 2017/0119714 A1 | 5/2017 | Chandraratna et al. |
| 2018/0064670 A1 | 3/2018 | Chandraratna et al. |
| 2018/0116985 A1 | 5/2018 | Chandraratna et al. |
| 2018/0263939 A1 | 9/2018 | Chandraratna et al. |
| 2018/0318241 A1 | 11/2018 | Chandraratna et al. |
| 2018/0369181 A1 | 12/2018 | Chandraratna et al. |
| 2019/0117603 A1 | 4/2019 | Chandraratna et al. |
| 2019/0125705 A1 | 5/2019 | Chandraratna et al. |
| 2019/0201358 A1 | 7/2019 | Chandraratna et al. |
| 2019/0231726 A1 | 8/2019 | Chandraratna et al. |
| 2019/0298678 A1 | 10/2019 | Chandraratna et al. |
| 2019/0365681 A1 | 12/2019 | Chandraratna et al. |
| 2019/0381022 A1 | 12/2019 | Chandraratna et al. |
| 2020/0155488 A1 | 5/2020 | Chandraratna et al. |
| 2020/0155489 A1 | 5/2020 | Chandraratna et al. |
| 2020/0163915 A1 | 5/2020 | Chandraratna et al. |
| 2020/0170985 A1 | 6/2020 | Chandraratna et al. |
| 2020/0190008 A1 | 6/2020 | Chandraratna et al. |
| 2020/0390736 A1 | 12/2020 | Sanders et al. |
| 2021/0077445 A1 | 3/2021 | Chandarartna et al. |
| 2021/0128503 A1 | 5/2021 | Chandraratna et al. |
| 2021/0128504 A1 | 5/2021 | Chandarartna et al. |
| 2021/0161874 A1 | 6/2021 | Chandarartna et al. |
| 2021/0205243 A1 | 7/2021 | Chandraratna et al. |
| 2022/0117922 A1 | 4/2022 | Chandraratna et al. |
| 2022/0143000 A1 | 5/2022 | Chandraratna et al. |
| 2022/0151964 A1 | 5/2022 | Chandraratna et al. |

FOREIGN PATENT DOCUMENTS

| | | |
|---|---|---|
| JP | 2010-280585 A | 12/2010 |
| WO | 1994/012880 A2 | 6/1994 |
| WO | 1994/014777 | 7/1994 |
| WO | 1996/039374 A1 | 12/1996 |
| WO | 1997/009297 A2 | 3/1997 |
| WO | 1999/008992 A1 | 2/1999 |
| WO | 1999/033821 A1 | 7/1999 |
| WO | 1999/063980 A1 | 12/1999 |
| WO | 2000/020370 A1 | 4/2000 |
| WO | 2001/007028 A2 | 2/2001 |
| WO | 2002/089781 A2 | 11/2002 |
| WO | 2002/089842 | 11/2002 |
| WO | 2003/027090 A2 | 4/2003 |
| WO | 2003/062369 | 7/2003 |
| WO | 2003/078567 | 9/2003 |
| WO | 2003/093257 A1 | 11/2003 |
| WO | 2003/101928 | 12/2003 |
| WO | 2004/046096 | 6/2004 |
| WO | 2005/013949 A2 | 2/2005 |
| WO | 2005/027895 A2 | 3/2005 |
| WO | 2007/022408 A2 | 2/2007 |
| WO | 2007/041076 A2 | 4/2007 |
| WO | 2007/041398 | 4/2007 |
| WO | 2008/157394 A2 | 12/2008 |
| WO | 2010/041149 A2 | 4/2010 |
| WO | 2010/041449 | 4/2010 |
| WO | 2010/132671 A1 | 11/2010 |
| WO | WO2010132671 | * 11/2010 |
| WO | 2011/006157 A2 | 1/2011 |
| WO | 2013/020966 | 2/2013 |
| WO | 2013/090616 A1 | 6/2013 |
| WO | 2015/059632 A1 | 4/2015 |
| WO | 2015/066197 A1 | 5/2015 |
| WO | 2016/144976 A1 | 9/2016 |
| WO | 2017/075610 | 5/2017 |
| WO | 2017/075612 A1 | 5/2017 |
| WO | 2017/155577 A1 | 9/2017 |
| WO | 2017/155578 A1 | 9/2017 |

(56) References Cited

FOREIGN PATENT DOCUMENTS

| WO | 2019/046591 A1 | 3/2019 |
|---|---|---|
| WO | 2019/060600 A1 | 3/2019 |

OTHER PUBLICATIONS

"Intranasal medication delivery—brief overview of the concept." Intranasal.net. Accessed Feb. 24, 2017.
Io Therapeutics, Inc. Brochure for the Symposium on IRX4204 at the 11th International Conference on Alzheimer's and Parkinson's Diseases (2013).
Jassem et al., A randomized phase III trial comparing bexarotene/cisplatin/vinorelbine versus cisplatin/vinorelbine in chemotherapy-nave-patients with advanced or metastatic non-small cell lung cancer (NSCLC) Journal of Clinical Oneology, 2005 ASCO Annual Meeting Proceedings, vol. 23, No. 16S, Part I of II (Jun. 1 Supllement), Abstract 7024 (2005).
Johnson et al., Synthesis and biological activity of high-affinity retinoic acid receptor antagonists. Bioorganic & Medicinal Chemistry, vol. 7, No. 7, pp. 1321-1338 (1999).
Kagechika et al., Synthetic retinoids: recent developments concerning structure and clinical utility. Journal of Medicinal Chemistry, vol. 48, No. 19: 5875-5883, (2005).
Kawata et al., RXR partial agonist produced by side chain repositioning of alkoxy RXR full agonist retains antitype 2 diabetes activity without the adverse effects. J Med. Chem. 58(2):912-926 (2015).
Kimura et al., IL-6: Regulator of Treg/Th17 balance. Eur. J. Immunol., 40:1830-1835 (2010).
Kim et al., Immunopathogenesis and therapy of cutaneous T cell lymphoma. Science in Medicine, The JCI Textbook of Molecular Medicine. Editors Marks et al., p. 164 (2007).
Klein et al., Cardiovascular involvement in general medial conditions. Thyroid disease and the heart. Circulation, 116:1725-1735 (2007).
Klein et al., Identification and functional separation of retinoic acid receptor neutral antagonists and inverse agonists. The Journal of Biological Chemistry, vol. 271, No. 37, pp. 22692-22696, 1996.
Knol et al., Absence of modulation of CD4+CD25high regulatory T cells in CTCL patients treated with bexarotene. Experimental Dermatology, 19:e95-e102 (2010).
Kotani et al., A naturally occurring rexinoid, honokiol, can serve as a regulator of various retinoid X receptor heterodimers. Biol. Pharm. Bull. 35(1):1-9 (2012).
Laclair et al., Treatment with bexarotene, a compound that increases apolipoprotein-E, provides no cognitive benefit in mutant APP/PS1 mice, Molecular Neurodegeneration 8:18 (10pp) (2013).
Lampen et al., Effects of receptor-selective retinoids on CYP26 gene expression and metabolism of all-trans-retinoic acid in intestinal cells. Drug Metabolism & Disposition, vol. 29, No. 3, pp. 742-747 (2001).
Lefebvre et al., Retinoid X receptors: common heterodimerization partners with distinct functions. Trends Endocrinol. Metab. 21:676-683 (2010).
Levasque et al., Nur77 and retinoid X receptors: crucial factors in dopamine-related neuroadaptation. Trends in Neuroscience, vol. 30, No. 1, pp. 22-30 (2007).
Li et al., Distinct Mechanisms of Glucose Lowering by Specific Agonists for Peroxisomal Proliferator Activated Receptor gamma and Retinoic Acid X Receptors, Journal of Biological Chemistry 280(46):38317-38327, 2005.
Liu et al., Combination Therapy of Insulin-Like Growth Factor Binding Protein-3 and Retinoid X Receptor Ligands Synergize on Prostate Cancer Cell Apoptosis In vitro and In vivo. Clin Cancer Res, 11(13):4851-4856 (2005).
Lowenthal et al., The Ethics of Early Evidence—Preparing for a Possible Breakthrough in Alzheimer's Disease, N Engl J Med., 367(6):488-490 (2012).

Macchia et al., RXR receptor agonist suppression of thryoid function: central effects in the absence of thyroid hormone receptor. Am. J. Physiol. Endocrinol. Metab., vol. 283, pp. E326-E331 (2002).
Mangelsdorf et al., Characterization of three RXR genes that mediate the action of 9-cis retinoic acid. Genes and Development 6:329-344 (1992).
Marketwire 2012: IRX4204 as a Potential Disease-Modifying Treatment for Alzheimer's Disease.
Marks et al., Science in Medicine: The JCI textbook of Molecular Medicine, p. 164 (2007).
Martin et al., Induction of the fatty acid transport protein 1 and acyl-CoA synthase genes by dimer-selective rexinoids suggests that the peroxisome proliferator-activated receptor-retinoid X receptor heterodimer is their molecular target. JBC 275(17):12612-12618 (2000).
McFarland et al., Low dose bexarotene treatment rescues dopamine neurons and restores behavioral function in models of Parkinson's disease. ACS Chem. Neurosci. 4:1430-1438 (2013).
Migliore, Intranasal Delivery of GDNF for the Treatment of Parkinson's Disease. Doctoral Thesis, Pharmaceutical Sciences, Northeastern University, Boston, MA (2008).
Miller et al., Initial clinical trial of a selective retinoid X receptor ligand, LGD1069. J Clin Oncol., 15(2):790-795 (1997).
Monahan et al., Neuroinflammation and peripheral immune infiltration in Parkinson's disease: an autoimmune hypothesis. Cell Transplant, 17:363-372 (2008).
Morris & Burns, Insulin: An Emerging Treatment for Alzheimer's Disease Dementia? Curr. Neurol. Neurosci. Rep. 12(5):520-527 (2012).
Munhoz et al., Parkinson's disease and thyroid dysfunction. Parkinsonism & Related Disorders, 10(6):381-383 (2004).
National Multiple Sclerosis Society, Medications, accessed May 12, 2017, pp. 1-5.
Natrajan et al., Retinoid X receptor activation reverses age-related deficiencies in myelin debris phagocytosis and remyelination. Brain A Journal of Neurology, 138:3581-3597 (2015).
Nishimaki-Mogami et al., The RXR agonists PA024 and HX630 have different abilities to activate LXR/RXR and to induce ABCA1 expression in macrophage cell lines. Biochemical Pharmacology, 76: 1006-1013 (2008).
Ohsawa et al., Modification of the lipophilic domain of RXR agonists differentially influences activation of RXR heterodimers. ACS Med Chem Lett., 1:521-525 (2010).
Olson et al., Immunomodulation as a neuroprotective and therapeutic strategy for Parkinson's disease. Curr Opin Pharmacol. 26:87-95 (2016).
Park et al., Salvage chemotherapy of gemcitabine, dexamethasone, and cisplatin (GDP) for patients with relapsed or refractory peripheral T-cell lymphomas: a consortium for improving survival of lymphoma (CISL) trial. Ann. Hematol., vol. 94, No. 11, pp. 1845-1851, see abstract (2015).
Perlmann et al., A novel pathway for vitamin A signaling mediated by RXR heterodimerization with NGFI-B and NURR1. Genes & Develop. 9:769-782 (1995).
Petty et al., Weekly paclitaxel (Taxol®), carboplatin (Paraplatin®), and bexarotene (Tagretin®) for the treatment of patients with advanced non-small cell lung cancer: Efficacy results from a Phase I/II study. Journal of Clinical ONcolocy, 2005 ASCO Annual Meeting Proceedings, vol. 23, No. 16S, Part I of II (June 1 Supplement) Abstract 7243 (2005).
Pierrot et al., Targretin Improves Cognitive and Biological Markers in a Patient with Alzheimer's Disease. Journal of Alzheimer's Disease, 49:271-276 (2016).
Price et al., Comment on ApoE-directed Therapeutics Rapidly Clear beta-Amyloid and Reverse Deficits in AD Mouse Models. Science 340:924-d (2013).
Ramaswamy et al., Trophic factors therapy in Parkinson's disease. Prog. Brain Res., 175:201-216 (2009).
Ramlau et al., Randomized phase III trial comparing bexarotene (L1069-49)/cisplatin/vinorelbine with cisplatin/vinorelbine in chemotherapy-naïve patients with advanced or metastic non-small-cell lung cancer: Spirit I. J. Clin. Oncol., 26:1886-1892 (2008).

(56) References Cited

OTHER PUBLICATIONS

Reynolds et al., Regulatory T cells attenuate Th17 cell-mediated nigrostriatal dopaminergic neurodegneration in a model of Parkinson's disease. J. Immunol., vol. 184, pp. 2261-2271 (2010).
Riancho et al., Neuroprotective effect of bexarotene in SOD1G93A mouse model of amyotrophic lateral sclerosis. Frontiers in Cellular Neuroscience 9:Article 250 (2015).
Rigas et al., Emerging role of rexinoids in non-small cell lung cancer: Focus on bexarotene. The Oncologist, 10:22-33 (2005).
Rizvi et al., A phase I study of LGD1069 in adults with advanced cancer. Clin. Cancer Res., 5:1658-1664 (1999).
Sacchetti et al., Requirements for heterodimerization between orphan nuclear receptor Nurr1 and Retinoid X Receptors. The Journal of Biological Chemistry, 277(38):35088-35096 (2002).
Salama et al., Role of L-thyroxin in counteracting rotenone induced neurotoxocity in rats. Environmental Toxicology and Pharmacology, 35:270-277 (2013).
Sherman et al., Central hypothyroidism associated with retinoid X receptor-selective ligands. The New England Journal of Medicine, vol. 340, No. 14, pp. 1075-1079 (1999).
Silvestroff et al., Cuprizone-induced demyelination in the rat cerebral cortex and thyroid hormone effects on cortical remyelination. Experimental Neurology, 235, pp. 357-367 (2012).
Smit et al., Bexarotene-induced hypothrodism: bexarotene stimulates the peripheral metabolism of thyroid hormones. J. Clin. Endocrinol. Metab., 92(7):2496-2499 (2007).
Suh et al., Prevention and treatment of experimental breast cancer with the combination of a new selective estrogen receptor modulator, Arzoxifene, and a new rexinoid, LG 100268. Clin Cancer Res, 8:3270-3275 (2002).
Takahashi et al., Novel retinoid X receptor antagonists: specific inhibition of retinoid synergism in RXR-RAR heterodimer actions. Journal of Medicinal Chemistry, vol. 45, No. 16, pp. 3327-3330 (2002).
Teng et al., Identification of highly potent retinoic acid receptor alpha-selective antagonists. Journal of Medicinal Chemistry, vol. 40, pp. 2445-2451 (1997).
Tesseur et al., Comment on ApoE-directed Therapeutics Rapidly Clear beta-Amyloid and Reverse Deficits in AD Mouse Models. Science, 340:924-e (2013).
Tovar-Y-Romo et al., Trophic factors as modulators of motor neuron physiology and survival: implications for ALS therapy. Frontiers in Cellular Neuroscience, 8:Article 61 (2014).
Trillo et al., Ascending monoaminergic systems alterations in Alzheimer's disease. Translating basic science into clinical care. Neuroscience and Biobehavioral Riviews, 37:1363-1379 (2013).
U.S. Appl. No. 16/228,217, filed Dec. 20, 2018.
U.S. Appl. No. 16/083,619, filed Sep. 10, 2018.
U.S. Appl. No. 15/769,551, filed Apr. 18, 2018.
U.S. Appl. No. 16/083,799, filed Sep. 10, 2018.
U.S. Appl. No. 16/222,518, filed Dec. 17, 2018.
Uslu et al., Doxazosin: a new cytotoxic agent for prostate cancer? BJU International, vol. 85, pp. 672-675 (2000).
Veeraraghavalu et al., Comment on "ApoE-directed Therapeutics Rapidly Clear beta-Amyloid and Reverse Deficits in AD Mouse Models. Science 340:924-f, 2013.
Volakakis et al., Nurr1 and Retinoid X Receptor ligands stimulate Ret signaling in dopamine neurons and can alleviate alpha-synuclein disrupted gene expression. J. Neurosci, 35(42):14370-14385 (2015).
Walkley et al., Retinoic acid receptor anatagonism in vivo expands the numbers of precursor cells during granulopoiesis. Leukemia, vol. 16, No. 9, pp. 1763-1772 (2002).
Wallen-Mackenzie et al., Nurr1-RXR heterodimers mediate RXR ligand-induced signaling in neuronal cells. Genes and Development, 17: 3036-3047 (2003).
Wang et al., Selective brain penetrable Nurr1 transactivator for treating Parkinson's disease. Oncotarget 7(7):7469-7479 (2016).
Wang, (2013) Slide presentation at the Symposium on IRX4204 at the 11th International Conference on Alzheimer's and Parkinson's Diseases: The Novel RXR agonist IRX4204 as a Potential Disease-Modifying Agent in Alzheimer's Disease.
WebMD, Common Drugs and Medicines to Treat Multiple Sclerosis; Drugs & Medications Search, accessed May 12, 2017; pp. 1-3.
Xiao et al., Retinoic acid increases Foxp3+ regulatory T cells and inhibits development of TH17 cells by enhancing TFG-β-driven Smad3 signaling and inhibiting IL-6 and IL-23 receptor expression. The Journal of Immunology, 181:2277-2284 (2008).
Xiao et al., Adenomatous polyposis coli (APC)-independent regulation of beta-catenin degradation via a retinoid X receptor-mediated pathway. Journal of Biological Chemistry, vol. 278, No. 32, pp. 29954-29962 (2003).
Yacila & Sari, Potential Therapeutic Drugs and Methods for the Treatment of Amyotrophic Lateral Sclerosis. Curr. Med. Chem., 21(31):3583-3593 (2014).
Yamada et al., Retinoid X receptor ligands: a patent review (2007-2013). Expert Opin. Ther. Patents, 24(4):443-452 (2014).
Zapata-Gonzalez et al., 9-cis-retinoic acid (9cRA), a retinoid X receptor (RXR) ligand, exerts immunosuppressive affects on dendritic cells by RXR-dependent activation: inhibition of peroxisome proliferator-activated receptor gamma blocks some of the 9cRA activities, and precludes them to mature phenotype development. The Journal of Immunogloy, 178:6130-6139 (2007).
Zhang et al., Thyroid hormone potentially benefits multiple sclerosis via facilitating remyelination. Mol. Neurobiol., 53, pp. 4406-4416 (2016).
U.S. Appl. No. 16/296,012, filed Mar. 7, 2019.
Alcala-Barraza et al., Intranasal delivery of neurotrophic factors BDNF, CNTF, EPO, and NT-4 to the CNS. Journal of Drug Targeting, 18(3):179-190 (2009).
Altucci L et al., RAR and RXR modulation in cancer and metabolic disease. Nature Review Drug Discovery, vol. 6: 793-810 (2007).
Alzforum 2013: Can Cancer Therapy Be Neurodegenerative Wonder Drug?
Annerbo et al., Review Article: A clinical review of the association of thyroid stimulating hormone and cognitive impairment. ISRN Endocrinology, vol. 2013, Article ID 856017, 6 pages (2013).
Balasubramanian et al., Suppression of human pancreatic cancer cell proliferation by AGN194204, an RXR-selective retinoid. Carcinogenesis, 2004, vol. 25, No. 8, pp. 1377-1385.
Balducci et al., The Continuing Failure of Bexarotene in Alzheimer's Disease Mice. J Alzheimers Dis., 46:471-482 (2015).
Benson et al., All-trans retinoic acid mediates enhanced T reg cell growth, differentiation, and gut homing in the face of high levels of co-stimulation. The Journal of Experimental Medicine, vol. 204, No. 8, pp. 1765-1774 (2007).
Beyer et al., Weight change and body composition in patients with Parkinson's disease. J. Am. DietAssoc., vol. 95, pp. 979-983 (1995).
Bilbao et al., Insulin-like growth factor-1 stimulates regulatory T cells and suppresses autoimmune disease. EMBO Mol. Med., 6(11):1423-1435 (2014).
Blumenschein et al., A randomized phase III trial comparing bexarotene/carboplatin/paclitaxel versus carboplatin/paclitaxel in chemotherapy-naive patients with advanced or metastatic non-small cell lung cancer (NSCLC). Journal of Clinical Oncology, 2005 ASCO Annual Meeting Proceedings, vol. 23, No. 16S, Part I of II, Abstract 7001 (2005).
Bordoni et al., Bexarotene improves TTP in untreated, advanced NSCLC, when given in combination with carbolalin/paclitaxel. Journal of Clinical Oncology, ASCO 2005 Annual Meeting, Abstract 7270.
Breen et al., Regulation of Thyroid-Stimulating Hormone beta-Subunit and Growth Hormone Messenger Ribonucleic Acid Levels in the Rat: Effect of Vitamin A Status, Endocrinology 136:543-9 (1995).
Cal et al., Doxazosin: a new cytotoxic agent for prostate cancer? BJU Int. 85:672-675 (2000).
Dalza et al., Thyroid hormone activates oligodendrocyte precursors and increases a myelin-forming protein and NGF content in the spinal cord during experimental allergic encephalomyelitis. PNAS, vol. 99, No. 5, pp. 3258-3263 (2002).

(56) References Cited

OTHER PUBLICATIONS

Coya et al., Retinoic Acid Inhibits In Vivo Thyroid-Stimulating Hormone Secretion, Life Sciences, Pharmacology Letters, 60:247-50, 1997.
Cramer et al., ApoE-directed therapeutics rapidly clear β-amyloid and reverse deficits in AD mouse models. Science, 335(6075): 1503-1506 (2012).
Drowe et al., A retinoid X receptor (RXR)-selective retinoid reveals that RXR-alpha is potentially a therapeutic target in breast cancer cell lines, and that it potentiates antiproliferative and apoptotic responses to peroxisome proliferator-activated receptor ligands. Breast Cancer Res., vol. 6, No. 5, pp. R546-R555 (2004).
Cummings et al., Double-blind, placebo-controlled, proof-of-concept trial of bexarotene Xin moderate Alzheimer's disease. Alzheimer's Research & Therapy, 8:4 (2016).
Debnath & Berk, Th17 Pathway—Mediated Immunopathogenesis of Schizophrenia: Mechanisms and Implications. Schizophrenia Bulletin, 40(6):1412-1421 (2014).
Dell'Acqua ML et al., Functional and molecular evidence of myelin- and neuroprotection by thyroid hormone administration in experimental allergic encephalomyelitis. Neuropath. Appl. Neurobiol., 38:454-470 (2012).
D'Intino G et al., Triiodothyronine administration ameliorates the demyelination/remyelination ratio in a non-human primate model of multiple sclerosis by corrected tissue hypothyroidism. J Neuroendocrin., 23:778-790 (2011).
Dore et al., Insulin-like growth factor I protects and rescues hippocampal neurons against beta-amyloid- and human amylin-induced toxicity. Proc. Natl. Acad. Sci. USA, 94:4772-4777 (1997).
Duvic et al., Phase 2 and 3 Clinical Trial of Oral Bexarotene (Targretin Capsules) for the Treatment of Refractory or Persistent Early-Stage Cutaneous T-Cell Lymphoma, Arch Dermatol. 137:581-593, 2001.
Estephan et al., Phase II trial of gemcitabine (G), carboplatin (C) and bexarotene (B) in patients (pts) with newly diagnosed, locally-advanced or metastatic non-small cell carcinoma of the lung. Journal of Clinical Oncology, 2005 ASCO Annual Meeting Proceedings, vol. 23, No. 16S, Part I of II (Jun. 1 Supplement, Abstract 7308 (2005).
Elias et al., Retinoic acid inhibits TH17 polarization and enhances FoxP3 expression through a Stat-3/Stat-5 independent signaling pathway. Blood, vol. 111, No. 3, pp. 1013-1020 (2008).
Fitz et al., Comment on ApoE-directed Therapeutics Rapidly Clear beta-Amyloid and Reverse Deficits in AD Mouse Models. Science 340:924-c (2013).
Franco et al., Thyroid hormones promote differentiation of oligodendrocyte progenitor cells and improve remyelination after cuprizone-induced demyelination. Experimental Neurology, 212, pp. 458-467, 2008 (2008).
Freiherr et al., Intranasal Insulin as a Treatment for Alzheimer's Disease: A Review of Basic Research and Clinical Evidence. CNS Drugs 27:505-514 (2013).
Friling et al., Activation of retinoid X receptor increases dopamine cell survival in models for Parkinson's disease. BMC Neuroscience, 10: 146 (2009).
Fu et al., Thyroid hormone prevents cognitive deficit in a mouse model of Alzheimer's disease. Neuropharmacology, 58:722-729 (2010).
Gibb et al., The substantia nigra and ventral tegmental area in Alzheimer's disease and Down's sydrome. J. Neurol. Neurosurg. and Psychiatry, 52:193-200 (1989).
Golub et al., Molecular classification of cancer: Class discovery and class prediction by gene expression monitoring. Science, vol. 286, Oct. 15, 1999, pp. 531-537.
Gonzalez et al., T-cell-mediated regulation of neuroinflammation involved in neurodegenerative diseases. J Neuroinflam 11:201-212 (2014).
Govindan et al., Phase II trial of bexarotene capsules in patients with non-small-cell lung cancer (NSCLC) who have Failed at least 2 prior systemic therapies for Stage IIIB/IV disease. Journal of Clinical Oncology, 2005 ASCO Annual Meeting Proceedings, vol. 23, No. 16S, Part I of II, Abstract 7116 (2005).
Graber et al., Protective autoimmunity in the nervous system. Pharmacol. Therapeut., 121:147-159 (2009).
Haugen et al., The Thyrotrope-Restricted Isoform of the Retinoid-X Receptor-y1 Mediates 9-cis-Retinoic Acid Suppression of Thyrotropin-beta Promoter Activity. Molecular Endocrinology 11:481-9, 1997.
Henkel et al., Regulatory T-lymphocytes mediate amyotrophic lateral sclerosis progression and survival. EMBO Mol. Med., 5:64-79 (2012).
Hu et al., Imbalance between IL-17A-Producing Cells and Regulatory T Cells during Ischemic Stroke. Mediators of Inflammation 2014: Article ID 813045, 2014.
Huang et al., Retinoid X receptor gamma signaling accelerates CNS remyelination, Nature Neuroscience, 14(1): 45-53, 2011 (Epub Dec. 5, 2010).
International Search Report and Written Opinion dated Mar. 28, 2013 for International Application Serial No. PCT/US2012/069566 filed on Dec. 13, 2012.
International Search Report and Written Opinion dated Jan. 5, 2017 for International Application Serial No. PCT/US2016/059770 filed Oct. 31, 2016.
International Search Report for PCT/US2007/011730 dated May 2, 2008.
International Search Report and Written Opinion dated Sep. 25, 2007 for International Application No. PCT/US2006/038252 filed on Oct. 2, 2006.
International Search Report and Written Opinion dated Dec. 29, 2016 for International Application No. PCT/US2016/059775 filed on Oct. 31, 2016.
International Search Report and Written Opinion dated Jan. 10, 2017 for International Application No. PCT/US2016/059776 filed on Oct. 31, 2016.
International Search Report and Written Opinion dated Dec. 29, 2016 for International Application No. PCT/US2016/059779 filed on Oct. 31, 2016.
International Search Report and Written Opinion dated May 22, 2017 for International Application No. PCT/US2016/059772 filed on Oct. 31, 2016.
International Search Report and Written Opinion dated Jan. 18, 2019 for International Application No. PCT/US2018/052031 filed on Sep. 20, 2018.
International Search Report and Written Opinion dated Dec. 11, 2018 for International Application No. PCT/US2018/048876 filed on Aug. 30, 2018.
International Application Serial No. PCT/US2018/052031 filed on Sep. 20, 2018.
Kabbinavar et al., An open-label phase II clinical trial of the RXR agonist IRX4204 in taxane-resistant, castration-resistant metastatic prostate cancer (CRPC). Journal of Clinical Oncology, vol. 32, No. 15 Suppl, p. 5073 (2014).
Supplementary European Search Report for European Patent Application Serial No. 16861059 dated May 16, 2019.
Assaf et al., Minimizing adverse side-effects of oral bexarotene in cutaneous T-cell lymphoma: an expert opinion. British Journal of Dermatology, 155, pp. 261-266 (2006).
Diab et al., Ligands for the peroxisome proliferator-activated receptor-gamma and the retinoid X receptor exert additive anti-inflammatory effects on experimental autoimmune encephalomyelitis. Journal of Neuroimmunology, 148, pp. 116-126 (2004).
Farmer et al., Retinoic acid receptor ligands based on the 6-cyclopropyl-2,4-hexadienoic acid. Bioorganic & Medicinal Chemistry Letters, 13:261-264 (2003).
Koivusalo et al., The cytotoxicity of chemotherapy drugs varies in cervical cancer cells depending on the p53 status Cancer Biology and Therapy, vol. 3278(11):1177-1183 (2004).
Liu et al., Mechanism of selective retinoid X receptor agonist-induced hypothroidism in the rat. Endocrinology, 143 (8):2880-2885 (2002).
Supplementary European Search Report for European Patent Application Serial No. 16861057 dated May 22, 2019.

(56) References Cited

OTHER PUBLICATIONS

Vuligonda et al., Enantioselective syntheses of potent retinoid X receptor ligands: Differential biological activities of individual antipodes. J. Med. Chem., 44. pp. 2298-2303 (2001).
Agarwal et al., Possible involvement of Bcl-2 pathway in retinoid X receptor alpha-induced apoptosis of HL-60 cells. Biochem Biophys Res Commun 230, 251-253 (1997).
Alsudais et al., Retinoid X receptor-selective signaling in the regulation of Akt/protein kinase B isoform-specific expression. The Journal of Biological Chemistry, vol. 291, No. 6, pp. 3090-3099 (2015).
Andreaone et al., Cerebral atrophy and white matter disruption in chronic schizophrenia. EUR Arch Psychiatry Clin Neurol 257:3-11 (Feb. 2007).
Andreaone et al., Cortical white-matter microstructure in schizophrenia. British J Psychiatry 191:113-119 (Aug. 2007).
Aranami et al., Th17 cells and autoimmune encephalomyelitis (EAE/MS). Allergology International, 57:115-120 (2008).
Banati et al., Inflammatory reaction in experimental autoimmune encephalomyelitis (EAE) is accompanied by a microglial expression of the betaA4-amyloid precursor protein (APP). Gila 14:209-215 (1995).
Becher et al., Th17 cytokines in autoimmune neuro-inflammation. Curr Opin Immunol 23(6):707-712 (2011).
Bendele, Animal models of rheumatoid arthritis. J Musculoskel Neuron Interact, 1(4):377-385 (2001).
Bettelli et al., Induction and effector functions of Th17 cells. Nature 453(7198):1051-1057 (2008).
Brown et al., Stable transfection of U937 cells with sense or antisense RXR-alpa cDNA suggests a role for RXR-alpha in the control of monoblastic differentiation induced by retinoic acid and vitamin D. Exp Cell Res 236, 94-102 (1997).
Certo et al., Activation of RXXR/PPARy underlies neuroprotection by bexarotene in ischemic stroke. Pharm. Resc. 102:298-307 (2015).
Chandraratna et al., Treatment with retinoid X receptor agonist IRX4204 ameliorates experimental autoimune encephalomyelitis. Am J Transl Res 8(2):1016-1026 (2016).
Chinese Office Action, dated May 21, 2020, for Chinese Patent Application No. 201680083364.8 (original and translation included).
Davis et al., White matter changes in schizoprenia—Evidence for myelin-related dysfunction. Arch Gen Psychiatry 60:443-456 (2003).
Debnath & Berk, Functional implications of the IL-23/IL-17 immune axis in schizophrenia. Mol Neurobiol, 54:8170-8178 (2017).
Defacque et al., Synergistic differentiation of U937 cells by all-trans retinoic acid and 1 alpha, 25 dihydroxyvitamin D3 is associated with the expression of retinoid X receptor alpha. Biochem Biophys Res Commun 203, 272-280 (1994).
Ding et al., Activation of Th17 cells in drug naive, first episode schizophrenia. Progress in Neuro-Pyschopharmacology & Biological Psychiatry, 51:78-82 (2014).
Domingues et al., Functional and pathogenic differences of Th1 and Th17 cells in experimental autoimmune encephalomyelitis. PLOS One, 5(11):e15531 (2010).
Drexhage et al., An activated set point of T-cell monocyte inflammatory networks in recent-onset schizophrenia patients involves both pro- and anti-inflammatory forces. International Journal of Neuropsychopharmacology, 14:746-755 (2011).
Extended European Search Report, dated Oct. 1, 2019, for European Application No. 16893789.4 filed Oct. 31, 2016.
Extended European Search Report for EP 16861057, dated May 22, 2019.
Flygt et al., Myelin loss and oligodendrocyte pathology in white matter tracts following traumatic brain injury in the rat. European Journal of Neuroscience 38:2153-2165 (2013).
Flynn et al., Abnormalities of myelination in schizophrenia detected in vivo with MRI, and post-mortem with analysis of oligodendrocyte proteins. Molecular Psychiatry, 8:811-820 (2003).
Gilgun-Sherki et al., Riluzole suppresses experimental autoimmune encephalomyelitis: implications for the treatment of multiple sclerosis. Brain Research, 989:196-201 (2003).
Graeppi-Dulac et al., Endocrine Side-Effects of Anti-Cancer Drugs: The impact of retinoids on the thyroid axis. European Journal of Endocrinology, 170(6), R253-R262 (2014).
Haqqani et al., Intercellular interactomics of human brain endothelial cells and Th17 lymphocytes: a novel strategy for identifying therapeutic targets of CNS inflammation. Cardiovascular Psychiatry and Neurology 2011: ID175364 (2011).
Harris, Retinoid therapy for rheumatoid arthritis. Annals of Internal Medicine, vol. 100(1), pp. 146-147 (1984).
Ho et al., Synergistic anticellular effect of a combination of beta-interferon and retinoic acid against U937 cells. Cancer Res 45, 5348-5351 (1985).
Hsu et al., Generation and characterization of monoclonal antibodies directed against the surface antigens of cervical cancer cells. Hybrid Hybridomics, vol. 23, No. 2, pp. 121-125 (2004)—abstract.
Inglese et al., Therapeutic strategies in multiple sclerosis: A focus on neuroprotection and repair and relevance to schizophrenia. Schizophrenia Research, 161:94-101 (2015).
Johnson et al., Axonal pathology in traumatic brain injury. Exp Nuerol, 246:35-43 (2013).
Jones et al., Animal models of schizophrenia. British Journal of Pharmacology, 164:1162-1194 (2011).
Kebir et al., Human Th17 lymphocytes promote blood-brain barrier disruption and central nervous system inflammation. Nat Med 13(10):1173-1175 (2007).
Kim, Chang H. Regulation of FoxP3+ regulatory T cells and Th17 cells by retinoids. Clinical and Developmental Immunology, vol. 2008, 12 pages (2008).
Komiyama et al., IL-17 plays an important role in the development of experimental autoimmune encephalomyelitis. J. Immunol., 177:566-573 (2006).
Koster et al., Emerging drugs for schizophrenia: an update. Expert Opin Emerging Drugs, 19(4):511-531 (2014).
Lalloyer et al., Rexinoid bexarotene modulates triglyceride but not cholesterol metabolism in the liver. Arterioscler Thromb Vase Biol 29(10):1488-1495 (2009).
Li et al., Plasma levels of Th17-related cytokines and complement C3 correlated with aggressive behavior in patients with schizophrenia Psychiatry Research, 246:700-706 (2016).
Liby et al., A new rexinoid, NXR194204, prevents carcinogenesis in both the lung and mammary gland. Clin Cancer Res, 13(20):6237-6243 (2007).
Mai et al., T helper 17 cells interplay with CD4+CD25highFoxp3+ Tregs in regulation of inflammations and autoimmune diseases. Front Biosci, 15:986-1006 (2010).
Mehta et al., Activation of retinoid receptors RAR alpha and RXR alpha induces differentiation and apoptosis, respectively, in HL-60 cells. Cell Growth Differ 7, 179-186 (1996).
Miller et al., Meta-analysis of cytokine alterations in schizophrenia: Clinical status and antipsychotic effects. Biol Psychiatry, 70(7):663-671 (2011).
Miller et al., Meta-analysis of lymphocytes in schizophrenia: Clinical status and antipsychotic effects. Biol Psychiatry 73(10):993-999 (2013).
Mor et al., Autoimmune encephalomyelitis and uveitis induced by T cell immunity to self beta-synuclein. The Journal of Immunology, 170:628-634 (2003).
Moriya et al., Edaravone, a free radical scavenger, ameliorates experimental autoimmune encephalomyelitis. Neuroscience Letters, 440:323-326, 2008.
Mucida et al., Supplemental Online Material: Reciprocal Th-17 and regulatory T cell differentiation mediated by retinoic acid. Retrieved on Mar. 5, 2021. Retrieved from internet, url:www.sciencemag.org/cgi/conent/full/1145697/DC1>(Year:2007).
Mucida et al., Reciprocal Th-17 and regulatory T cell differentiation mediated by retinoic acid. Science, vol. 317 (5835), pp. 256-260 (2007).
Murphy et al., Infiltration of Th1 and Th17 cells and activation of microglia in the CNS during the course of experimental autoimmune encephalomyelitis. Brain Behavior and Immunity, 24:641-651 (2010).
Nagy et al., Activation of retinoid X receptors induces apoptosis in HL-60 cells. Mol Cell Biol 15, 3540-3551 (1995).

(56) References Cited

OTHER PUBLICATIONS

Pasternak et al., The extent of diffusion MRI markers of neuroinflammation and white matter deterioration in chronic schizophrenia. Schizophrenia Research, 161(1):113-118 (2015).
Reagan-Shaw et al., Dose translation from animal to human studies revisted. FASEB J, 22:659-661 (2007).
Rostami et al., Role of Th17 cells in the pathogenesis of CNS inflammatory demyelination. J. Neurol Sci, 330:76-87 (2013).
Saresella et al., T helper-17 activation dominates the immunologic milieu of both amyotrophic lateral sclerosis and progressive multiple sclerosis. Clincal Immunology, 148:79-88 (2013).
Schneider et al., Hyperphosphorylation and aggregation of Tau in experimental autoimmune encephalomyelitis. J Biol Chem 279(53):55833-55839 (2004).
Segal, Th17 cells in autoimmune demyelinating disease. Semin Immunopathol, 32(1):71-77 (2010).
Science Daily [online] (2007), Potential role for retinoic acid in autoimmune and inflammatory diseases identified, La Jolla Institute for Allergy and Immunology p. 1-3 Retrieved from the internet, Retrieved on Mar. 5, 2021, <url:www.sciencedaily.com/releases/2007/06/070614151809.htm> (Year:2007).
Singaporean Written Opinion, dated Sep. 26, 2019, for Singaporean Application No. 11201807250P filed on Oct. 31, 2016.
Singaporean Written Opinion, dated Sep. 16, 2019, for Singaporean Application No. 11201807255Y filed on Oct. 31, 2016.
Smith, A comprehensive macrophage-T-lymphocyte theory of schizophrenia. Medical Hypotheses, 39:248-257 (1992).
Stromnes et al., Differential regulation of central nervous system autoimmunity by TH1 and TH17 cells. Nat Med, 14(3):337-342 (2008).
Trapp et al., Axonal transection in the lesions of multiple sclerosis. N Engl J Med 338:278-785 (1998).
U.S. Appl. No. 16/898,230, filed Jun. 10, 2020.
U.S. Appl. No. 17/064,969, filed Oct. 7, 2020.
U.S. Appl. No. 17/126,714, filed Dec. 18, 2020.
U.S. Appl. No. 17/126,787, filed Dec. 18, 2020.
U.S. Appl. No. 17/150,646, filed Jan. 15, 2021.
Waite et al., Review Article: Th17 response and inflammatory autoimmune diseaes. International Journal of Inflammation, vol. 2012, Article ID 819467, 10 pp (2011).
Wikipedia, Experimental autoimmune encephalomyelitis, https://en.wikipedia.org/wiki/Experimental_autoimmune_encephalomyelitis, accessed Jul. 1, 2019 (last edited on Feb. 10, 2019).
Wikipedia, Schizophrenia, https://www.nimh.nih.gov/health/statistics/schizophrenia.html, accessed Feb. 20, 2020.
Zhang et al., Induction of apoptosis by bexarotene in cutaneous T-cell lymphoma cells: relevance to mechanism of therapeutic action. Clin Cancer Res 8, 1234-1240 (2002).
Zhao et al., Application of thyroid hormone in animal models of multiple sclerosis. Drug Evaluation Research, 39 (1):148-151 (2016).
Hueber et al., Effects of AIN457, a fully human antibody to interleukin-17A, on psoriasis, rheumatoid arthritis, and uveitis. Science Translational Medicine, vol. 2, Issue 52, 52ra72 (2010).
Rittenhouse et al., Thyroxine administration prevents *streptococcal* cell wall-induced inflammatory responses. Endocrinology, 138(4):1434-1439 (1997).
Singaporean Written Opinion, dated Apr. 22, 2021, for Singaporean Application No. 11201807255Y filed on Oct. 31, 2016.
Sugiyama et al., Dysfunctional blood and target tissue CD4+ CD25high regulatory T cells in psoriasis: Mechanism underlying unrestrained pathogenic effector T cell proliferation. J. Immunol, 174:164-173 (2005).

\* cited by examiner

FIG. 9A
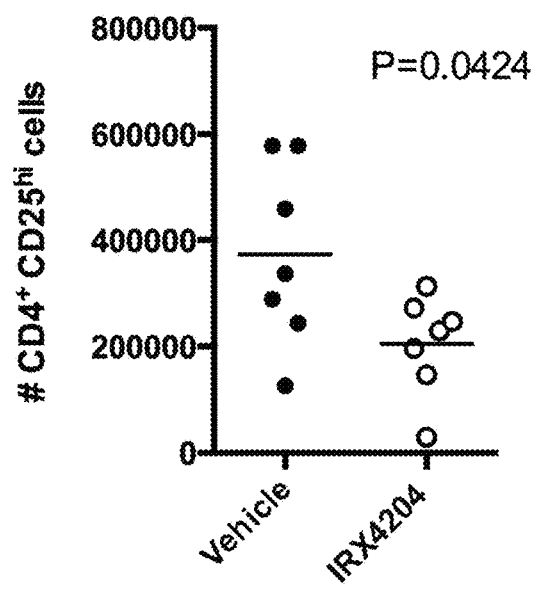
FIG. 9C
FIG. 9B
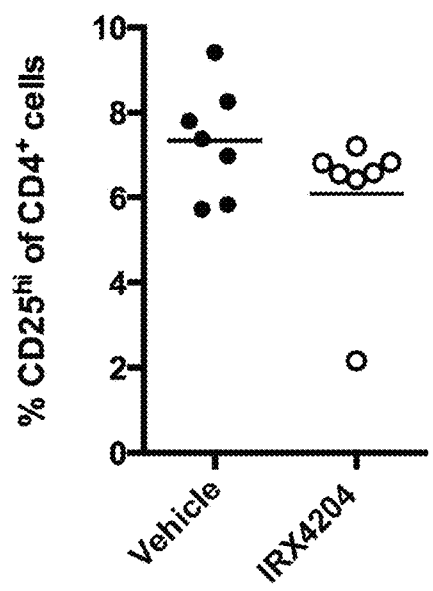
FIG. 9D
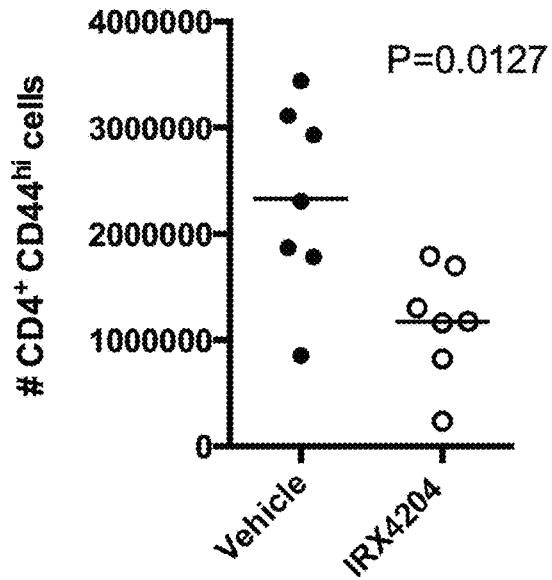
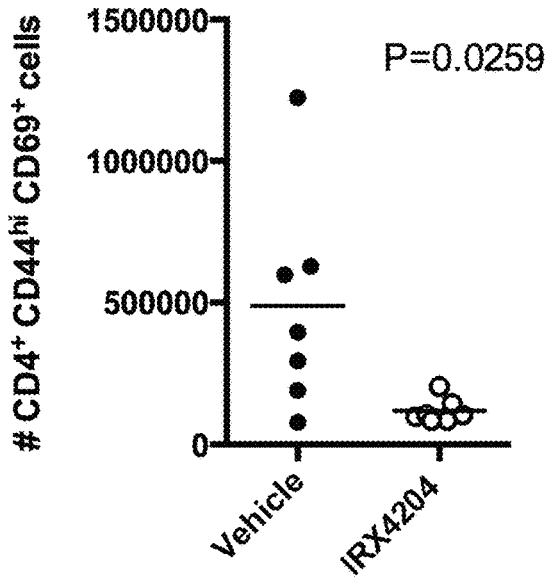

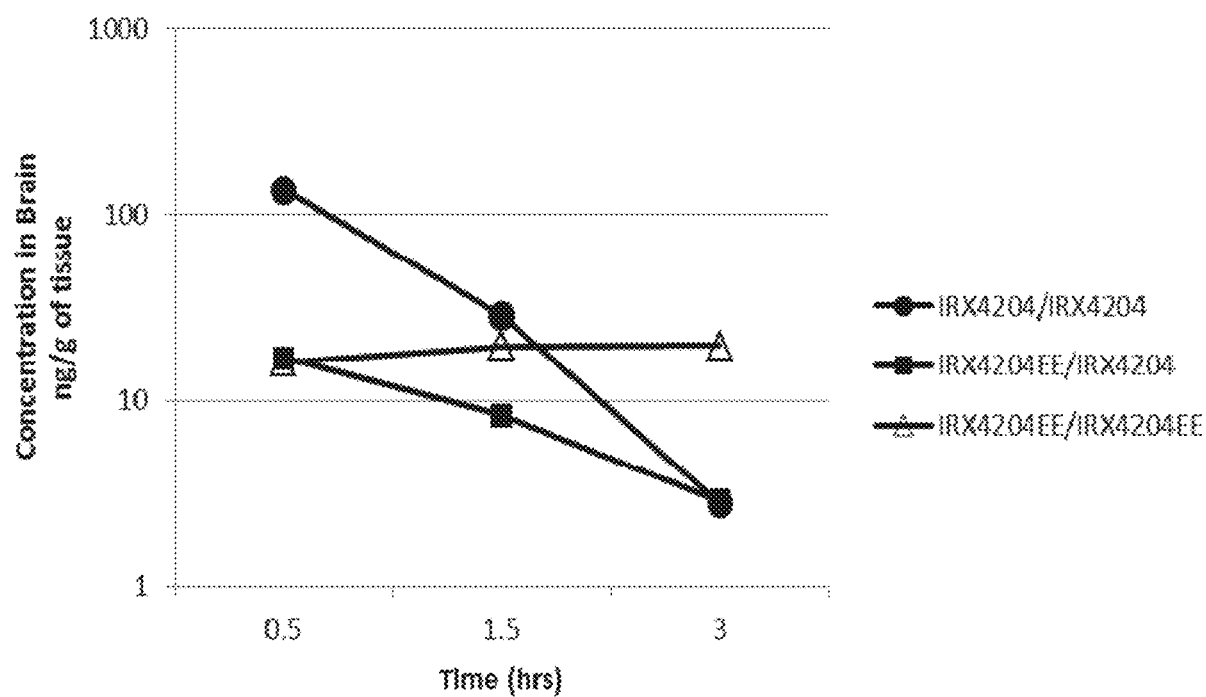

TREATMENT OF DISEASE WITH ESTERS OF SELECTIVE RXR AGONISTS

RELATED APPLICATIONS

This application claims the benefit of U.S. Provisional Patent Application 62/560,776, filed Sep. 20, 2017, the entire contents of which are incorporated by reference herein.

FIELD

The present disclosure is directed to methods of treating nervous system disorders or cancer with esters of retinoid X receptor (RXR) agonists.

BACKGROUND

The current standard of care treatment for nervous system diseases include several anti-inflammatory and immunomodulatory drugs that promote clinical benefit by modulating the patient's inflammatory/immune responses. While these therapies delay disease progression, they are unable to reverse the pathology or restore neurological function. One way to achieve significant advancement in the current standard of care for nervous system disorder patients is to promote remyelination or neuroprotection, or both, and thereby regenerate or maintain healthy axons and neurons.

SUMMARY

Disclosed herein are methods of treating nervous system disorders, cancer, muscular disorders, and autoimmune disorders, the methods comprising the step of administering to an individual in need thereof a therapeutically effective amount of an ester of a RXR agonist, wherein administration of the ester of the RXR agonist provides the RXR agonist which treats the disease or disorder in the individual.

Also disclosed herein are methods of treating a nervous system disorder, cancer, muscular disorders, and autoimmune disorders, the methods comprising the step of administering to an individual in need thereof a therapeutically effective amount of an ester of a RXR agonist and a therapeutically effective amount of a thyroid hormone, wherein administration of the ester of the RXR agonist provides the RXR agonist and the combination of the RXR agonist and the thyroid hormone treats the disease or disorder in the individual.

Also disclosed herein are methods of promoting survival or repair of neurons or glial cells in a patient with a nervous system disorder, the method comprising the step of administering to an individual in need thereof a therapeutically effective amount of an ester of an RXR agonist and a therapeutically effective amount of a thyroid hormone, wherein administration of the ester of the RXR agonist provides the RXR agonist and the combination of the RXR agonist and the thyroid hormone treats the nervous system disorder in the individual.

In some embodiments, the ester of the RXR agonist has the structure of Formula II

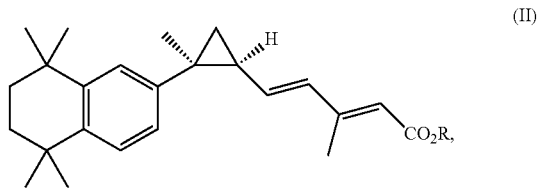

wherein R is lower alkyl of 1 to 6 carbons.

In some embodiments, the ester of the RXR agonist is 3,7-dimethyl-6(S),7(S)-methano,7-[1,1,4,4-tetramethyl-1,2,3,4-tetrahydronaphth-7-yl]2(E),4(E) heptadienoic ethyl ester (IRX4204EE). In some embodiments, the ester of a RXR agonist is an ester of bexarotene. In yet other embodiments, the ester of a RXR agonist is an ester of LG268.

In some embodiments, the ester of the RXR agonist treats the nervous system disorder in the individual by both promoting remyelination and by preventing demyelination by neuroprotection and modulating the individual's immune system. In certain embodiments, the combination of the ester of the RXR agonist and thyroxine treats the nervous system disorder in the individual by both promoting remyelination and neuroprotection of neurons and modulating the individual's immune system.

In some embodiments, the thyroid hormone is thyroxine.

In some embodiments, the nervous system disorder is a central nervous system (CNS) disorder such as multiple sclerosis, diffuse white matter injury in pre-term infants, neuromyelitis optica, acute disseminated encephalomyelitis, Marburg multiple sclerosis, diffuse myelinoclastic sclerosis (Schilder's disease), Balo concentric sclerosis, solitary sclerosis, optic neuritis, transverse myelitis, amyotrophic lateral sclerosis, leukodystrophy (multiple variants, e.g. adrenoleukodystrophy, adrenomyeloneuropathy), Parkinson's disease, Alzheimer's disease, progressive supranuclear palsy, stroke, traumatic brain injury, radiation induced neuroinflammation, radiation somnolence syndrome, Devic's disease, inflammatory demyelinating diseases, CNS neuropathies, central pontine myelinolysis, Tabes dorsalis (syphilitic myelopathy), progressive multifocal leukoencephalopathy, or leukodystrophy.

In some embodiments, the disease of the central nervous system is Parkinson's disease, Alzheimer's disease, a multiple sclerosis, an optic neuritis, a stroke, a CNS trauma, amyotrophic lateral sclerosis, a neuropathy, a nervous system hypoxia, a CNS toxicity, a dementia, a retinopathy, Huntington's disease, a synucleinopathy, epilepsy, autism, schizophrenia, depression, or and aging-related CNS degeneration.

In some embodiments, the CNS disorder is a demyelination-related disorder such as multiple sclerosis or radiation-induced central nervous system inflammation.

In some embodiments, the CNS disorder is a peripheral nervous system disorder such as Guillain-Barré Syndrome, acute inflammatory demyelinating polyneuropathy, chronic inflammatory demyelinating polyneuropathy, demyelinating diabetic neuropathy, progressive inflammatory neuropathy, drug- or toxin-induced neuropathy, such as chemotherapy-induced neuropathy or organophosphate-induced neuropathy, anti-MAG peripheral neuropathy, Charcot-Marie-Tooth Disease, or copper deficiency.

In some embodiments, the therapeutically effective amount of the ester of the RXR agonist is about 0.001 mg/day to about 1000 mg/day. In some embodiments, the therapeutically effective amount of the ester of the RXR agonist is about 10 mg/day to about 1000 mg/day. In some embodiments, the therapeutically effective amount of thyroxine is about 12.5 µg/day to about 250 µg/day.

In some embodiments, the ester of the RXR agonist is administered by nasal administration. In some embodiments, both the ester of the RXR agonist and thyroxine are administered by nasal administration. In some embodiments, the ester of the RXR agonist is administered orally. In some embodiments, the ester of the RXR agonist and the thyroxine are administered substantially simultaneously. In some embodiments, the ester of the RXR agonist and thyroxine are administered on different schedules. In some embodiments, the thyroid hormone is administered orally or subcutaneously.

In some embodiments, treatment with the combination of ester of the RXR agonist and thyroxine reduces at least one symptom of the demyelination-related disorder, wherein the at least one symptom reduced is inflammation, fatigue, dizziness, malaise, elevated fever and high body temperature, extreme sensitivity to cold in the hands and feet, weakness and stiffness in muscles and joints, weight changes, digestive or gastrointestinal problems, low or high blood pressure, irritability, anxiety, or depression, blurred or double vision, ataxia, clonus, dysarthria, fatigue, clumsiness, hand paralysis, hemiparesis, genital anesthesia, incoordination, paresthesias, ocular paralysis, impaired muscle coordination, weakness (muscle), loss of sensation, impaired vision, neurological symptoms, poor short-term memory, long-term memory loss, confusion, hallucinations, delusions, paranoia, impaired reasoning or judgement, unsteady gait, spastic paraparesis, incontinence, hearing problems, or speech problems. In some embodiments, treatment with the combination of ester of the RXR agonist and thyroxine reduces at least two symptoms of the demyelination-related disorder. In some embodiments, treatment with the combination of ester of the RXR agonist and thyroxine reduces at least five symptoms of the demyelination-related disorder.

Also disclosed herein are methods of treating multiple sclerosis, the method comprising the step of administering to an individual in need thereof a therapeutically effective amount of an ester of 3,7-dimethyl-6(S),7(S)-methano,7-[1,1,4,4-tetramethyl-1,2,3,4-tetrahydronaphth-7-yl]2(E),4(E) heptadienoic acid. In some embodiments the ester is a $C_{1-6}$ alkyl ester, such as an ethyl ester. Some embodiments further comprise administration of a thyroid hormone, such as thyroxine, wherein administration of the combination treats the multiple sclerosis in the individual and wherein the combination causes greater improvement in multiple sclerosis than the ester or the thyroid hormone alone.

Also disclosed herein are methods of treating a CNS demyelination-related disorder, the method comprising the step of administering to an individual in need thereof a therapeutically effective amount of an ester of 3,7-dimethyl-6(S),7(S)-methano,7-[1,1,4,4-tetramethyl-1,2,3,4-tetrahydronaphth-7-yl]2(E),4(E) heptadienoic acid. In some embodiments the ester is a $C_{1-6}$ alkyl ester, such as an ethyl ester. Some embodiments further comprise administration of a thyroid hormone, such as thyroxine, wherein administration of the combination treats the CNS demyelination-related disorder in the individual and wherein the RXR agonist is delivered directly to the CNS of the individual by intrathecal administration, epidural administration, cranial injection or implant, or nasal administration and wherein the combination causes greater improvement in the CNS demyelination-related disorder than the ester or the thyroid hormone alone.

Also disclosed herein are methods of treating Parkinson's Disease, the method comprising the step of administering to an individual in need thereof a therapeutically effective amount of an ester of 3,7-dimethyl-6(S),7(S)-methano,7-[1,1,4,4-tetramethyl-1,2,3,4-tetrahydronaphth-7-yl]2(E),4(E) heptadienoic acid. In some embodiments the ester is a $C_{1-6}$ alkyl ester, such as an ethyl ester. Some embodiments further comprise administration of a thyroid hormone, such as thyroxine, wherein administration of the combination treats the Parkinson's Disease in the individual and wherein the combination causes greater improvement in the Parkinson's Disease than the ester or the thyroid hormone alone.

Also disclosed herein are methods of treating Alzheimer's Disease, the method comprising the step of administering to an individual in need thereof a therapeutically effective amount of an ester of 3,7-dimethyl-6(S),7(S)-methano,7-[1,1,4,4-tetramethyl-1,2,3,4-tetrahydronaphth-7-yl]2(E),4(E) heptadienoic acid. In some embodiments the ester is a $C_{1-6}$ alkyl ester, such as an ethyl ester. Some embodiments further comprise administration of a thyroid hormone, such as thyroxine, wherein administration of the combination treats the Alzheimer's Disease in the individual and wherein the combination causes greater improvement in the Alzheimer's Disease than the ester or the thyroid hormone alone.

In some embodiments, the ester is an ethyl ester of 3,7-dimethyl-6(S),7(S)-methano,7-[1,1,4,4-tetramethyl-1,2,3,4-tetrahydronaphth-7-yl]2(E),4(E) heptadienoic acid.

In some embodiments, the method further comprises administration of a thyroid hormone. In some embodiments, the method further comprises determining free serum thyroxine; and adjusting the dose of thyroxine to keep thyroxine levels in a euthyroid range.

In some embodiments of methods disclosed herein, the method further comprises administration of a neurotrophic factor, or neurotrophic factor mimetic. In some embodiments, the RXR agonist is IRX4204. In some embodiments, the RXR agonist is bexarotene. In some embodiments, the neurotrophic factor is BDNF, GDNF, NGF, NT-3, bFGF, CNTF, NT-4/5, IGF, or insulin, or a mimetic thereof, or a combination of two or more thereof. In some embodiments, the neurotrophic factor is GDNF, or a GDNF mimetic, and the CNS disease is Parkinson's disease. In some embodiments, the neurotrophic factor is GDNF, or a GDNF mimetic, and the CNS disease is multiple sclerosis. In some embodiments, the neurotrophic factor is GDNF, or a GDNF mimetic, and the CNS disease is amyotrophic lateral sclerosis. In some embodiments, the neurotrophic factor is GDNF, or a GDNF mimetic, and the CNS disease is Alzheimer's disease. In some embodiments, the neurotrophic factor is BDNF and the CNS disease is Alzheimer's disease. In some embodiments, the neurotrophic factor is insulin or insulin-like growth factor, and the CNS disease is Alzheimer's disease. In some embodiments, the neurotrophic factor is BDNF and the CNS disease is multiple sclerosis. In some embodiments, the neurotrophic factor is BDNF, and the CNS disease is stroke, nervous system trauma, aging, or dementia. In some embodiments, the neurotrophic factor is BDNF, or GDNF, or insulin, or a mimetic thereof, or a combination of two or more thereof, and the CNS disease is aging-related CNS neurodegeneration. In some embodiments the neurotrophic factor is IGF, or a mimetic thereof, and the CNS disease is Parkinson's Disease, or Alzheimer's disease, or amyotrophic lateral sclerosis, or multiple sclerosis, or aging-related neurodegeneration. In some embodiments, the neurotrophic factor or mimetic is administered by oral, parenteral, nasal, or topical routes, or by controlled release.

Also disclosed herein is a combination of an RXR agonist, a thyroid hormone, and a neurotrophic factor, or neurotrophic factor mimetic, for in vitro promotion of survival or growth of neurons or glial cells, for subsequent implantation into the nervous system of a patient with a nervous system disorder.

Also disclosed herein are methods of providing a dose of IRX4204 to a patient in need thereof, comprising a step of administering a $C_{1-6}$ alkyl ester of IRX4204, wherein an effective dose of the $C_{1-6}$ ester of IRX4204 is lower than a corresponding effective dose of IRX4204.

Also disclosed herein are methods of providing a dose of IRX4204 to a patient in need thereof, comprising a step of administering a $C_{1-6}$ ester of IRX4204, wherein the dose of the $C_{1-6}$ alkyl ester of IRX4204 is greater than the maximum tolerated dose of IRX4204.

Also disclosed herein are methods of providing a dose of IRX4204 to a patient in need thereof, comprising a step of administering a $C_{1-6}$ alkyl ester of IRX4204, wherein Cmax of the active species is less than would result from administration of a same dose of IRX4204.

Also disclosed herein are methods of providing a dose of IRX4204 to a patient in need thereof, comprising a step of administering a $C_{1-6}$ alkyl ester of IRX4204, wherein Tmax of the active species is greater than would result from administration of a same dose of IRX4204.

In some embodiments, Cmax is determined in the blood. In some embodiments, Cmax is determined in the brain.

In some embodiments, the $C_{1-6}$ alkyl ester of IRX4204 is IRX4204 ethyl ester.

In some embodiments, amounts of IRX4204 and a $C_{1-6}$ alkyl ester of IRX4204 are compared on a mass basis. In some embodiments, amounts of IRX4204 and a $C_{1-6}$ alkyl ester of IRX4204 are compared on a molar basis.

Also disclosed herein are methods of treating cancer comprising providing a dose IRX4204 according to methods disclosed herein.

Also disclosed herein are methods of treating a nervous system disorder comprising providing a dose IRX4204 according to methods disclosed herein. In some embodiments, the nervous system disorder is a demyelination-related disorder. In some embodiments, the nervous system disorder is selected from the group of Parkinson's disease, multiple sclerosis, and Alzheimer's disease.

Also disclosed herein is the use of a $C_{1-6}$ alkyl ester of IRX4204 for providing a dose of IRX4204 to a patient in need thereof.

Also disclosed herein is a $C_{1-6}$ alkyl ester of IRX4204 for use in providing a dose of IRX4204 to a patient in need thereof.

Also disclosed herein is a $C_{1-6}$ alkyl ester of IRX4204 for use in the manufacture of a medicament for providing a dose of IRX4204 to a patient in need thereof.

In some embodiments of the uses disclosed herein, the patient in need thereof has cancer.

In some embodiments of the uses disclosed herein, the patient in need thereof has a nervous system disorder. In some embodiments, the nervous system disorder is selected from the group of Parkinson's disease, multiple sclerosis, and Alzheimer's disease.

With respect to alternative elements of the herein disclosed embodiments, for example, the various disorders to be treated, the various esters encompassed by $C_{1-6}$ alkyl ester, dosages, and dose ranges, some embodiments specifically include a species or subgenus, while other embodiments specifically exclude a species or subgenus. For example, in various embodiments the ester is the methyl ester, is the ethyl ester, or is not a hexyl ester.

BRIEF DESCRIPTION OF THE DRAWINGS

FIG. 3A depicts the number of CD4$^+$ cells and FIG. 3B depicts the number of CD11c$^+$ CD11b$^+$ cells (myeloid DC) in mice treated with the RXR agonist IRX4204 (4204) versus the vehicle control.

FIG. 9A-D depicts quantification (FIG. 9A) and frequency (FIG. 9B) of CD4+CD25hi cells, total number of effector and memory CD4 T cells (FIG. 9C), and total number of activated CD4 T cells (FIG. 9D) in splenocytes from EAE mice treated with 200 µg/day of IRX4204 or control.

FIG. 13A-B depict the concentrations of IRX4204 and IRX4204EE in plasma (FIG. 13A) and brain tissue (FIG. 13B) following an intravenous injection of one or the other into mice. The curves are labeled to indicate which substance was injected and which substance was assayed for before and after a slash "/", respectively. IRX4204EE/IRX4204 would indicate that the ethyl ester of IRX4204 (IRX4204EE) was injected but the data plotted is the concentration of IRX4204 following such injection.

DETAILED DESCRIPTION

Figure 1:
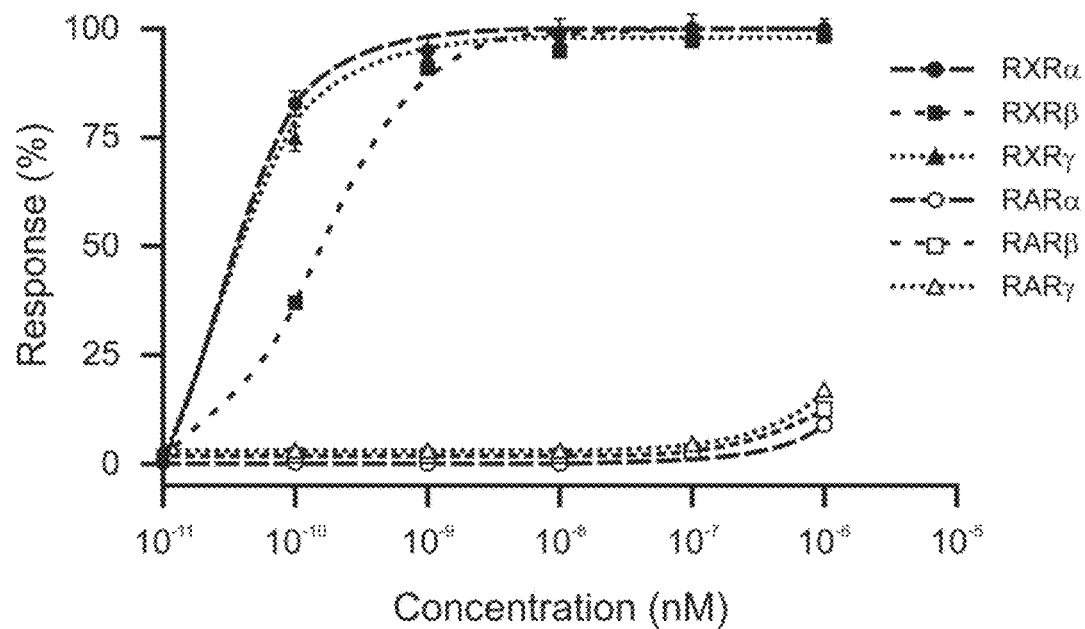
FIG. 1 shows RXR agonist activation of transcription from RXRα, RXRβ, RXRγ, RARα, RARβ, and RARγ using transactivation assays.

Disclosed herein are methods for treating nervous system disorders or cancer using esters of retinoid X receptor (RXR) agonists.

Many diseases of the nervous system are associated with demyelination of axons and neurons. Such disorders of demyelination may be autoimmune diseases or disorders of other etiologies. Multiple sclerosis (MS) is an example of an autoimmune disorder which is also associated with demyelination. Demyelination also plays a role in Parkinson's disease (PD). Accordingly, an optimal drug for the treatment of MS and diseases with a similar etiology would address the autoimmune aspect of the disease while concurrently enhancing remyelination and providing neuroprotection. MS is currently treated by several immunomodulatory drugs that provide clinical benefit by modulating patient immune responses and producing anti-inflammatory effects. These drugs delay disease progression but do not reverse disease pathology or restore neurological function by restoring myelination of damaged neurons. IRX4204 (194204, Formula III), a retinoid X receptor (RXR) ligand that has an unique mechanism of action in being a selective activator of RXR homodimers and RXR-Nurr1 heterodimers, particularly when combined with a thyroid hormone, simultaneously provides immunomodulatory activities and also promotes remyelination and neuroprotection. IRX4204 promotes the differentiation of suppressive Treg cells while simultaneously inhibiting the differentiation of pro-inflammatory Th17 cells thereby favorably affecting the aberrantly skewed Th17/Treg cell ratio which underlies human autoimmune diseases such as MS (see co-pending US2015/0038585, which is incorporated by reference for all it discloses regarding RXR agonists). Thus, by virtue of its effects on Th17/Treg cell ratios, IRX4204 will have clinical benefits similar to current standard of care treatments in MS, but will offer the added benefits of promoting remyelination and neuro protection.

IRX4204 esters are inherently inactive as RXR agonists and function as RXR agonist pro-drugs which need to be converted to free acid or conjugate base form to be active. Esters are expected to become hydrolyzed in the aqueous environment of the body thereby generating the same conjugate base active species as the free acid (that is, the anionic form of the dissociated acid), although the speed of absorption and conversion will typically be slower. Thus, as expected, the ethyl ester of IRX4204 (IRX4204EE) is less active than its parent form (IRX4204) in promoting the differentiation of Treg cells and in inhibiting the differentiation of Th17 cells in in vitro cell culture. IRX4204 can favorably change the skewed Th17/Treg cell ratio in an animal model of MS such as the EAE model of MS. Also, IRX4204 can induce significant oligodendrocyte precursor cell (OPC) differentiation in vitro while the ester, IRX4204EE, was considerably less active. However, in in vivo models of remyelination and neuroprotection, the ester, IRX4204EE, was surprisingly more active than IRX4204 in promoting remyelination of demyelinated CNS neutrons and in promoting neuroprotection. Accordingly, IRX4204 provides immunomodulatory activity and promote remyelination and neuroprotection (and regeneration), and will not only delay disease progression in MS but also effect neural maintenance and repair by protecting and regenerating healthy axons and neurons. IRX4204 is expected to be an optimal drug for the treatment of MS, PD, and other autoimmune diseases which are also associated with demyelination. The superior activity of the ester, IRX4204EE, was completely unexpected since it needs to be converted to the active species of IRX4204 for it to be active. These esters are advantageous because they accumulate in the brain and are converted to the active species to give prolonged, clinically relevant levels of the active form IRX4204 in the brain as compared to administration of the free acid form itself. Indeed, the esters being more lipophilic can more readily penetrate target tissues, such as the brain, contributing to their greater accumulation there. The more stable concentration of the ester observed in brain is consistent with the slower decay of concentration of the active free acid form in the brain than results from administration of the free acid form itself. Consequently, at late times after Tmax, a higher target tissue concentration of the active free acid form can result from administration of the ester than from administration of the free acid form itself.

The retinoic acid receptors (RARs) and the retinoid X receptors (RXRs) and their cognate ligands function by distinct mechanisms. The RARs always form heterodimers with RXRs and these RAR/RXR heterodimers bind to specific response elements in the promoter regions of target genes. The binding of RAR agonists to the RAR receptor of the heterodimer results in activation of transcription of target genes leading to retinoid effects. On the other hand, RXR agonists do not activate RAR/RXR heterodimers. RXR heterodimer complexes like RAR/RXR can be referred to as non-permissive RXR heterodimers as activation of transcription due to ligand-binding occurs only at the non-RXR protein (e.g., RAR); activation of transcription due to ligand binding does not occur at the RXR. RXRs also interact with nuclear receptors other than RARs and RXR agonists may elicit some of its biological effects by binding to such RXR/receptor complexes. These RXR/receptor complexes can be referred to as permissive RXR heterodimers as activation of transcription due to ligand-binding could occur at the RXR, the other receptor, or both receptors. Examples of permissive RXR heterodimers include, without limitation, peroxisome proliferator activated receptor/RXR (PPAR/RXR), farnesyl X receptor/RXR (FXR/RXR), nuclear receptor related-1 protein (Nurr1/RXR) and liver X receptor/RXR (LXR/RXR). Alternately, RXRs may form RXR/RXR homodimers which can be activated by RXR agonists leading to rexinoid effects. Also, RXRs interact with proteins other than nuclear receptors and ligand binding to an RXR within such protein complexes can also lead to rexinoid effects. Due to these differences in mechanisms of action, RXR agonists and RAR agonists elicit distinct biological outcomes and even in the instances where they mediate similar biological effects, they do so by different mechanisms. Moreover, the unwanted side effects of retinoids (RAR-associated toxicities), such as pro-inflammatory responses, hypertriglyceridemia, hypercholesterolemia, headaches, brain edema, or mucocutaneous toxicity, are mediated by activation of one or more of the RAR receptor subtypes. Stated another way, biological effects mediated via RXR pathways would not induce pro-inflammatory responses, and thus, would not result in unwanted side effects.

Thus, aspects of the present specification provide, in part, a RXR agonist. As used herein, the term "RXR agonist", is synonymous with "RXR selective agonist" and refers to a compound that selectively binds to one or more RXR receptors like a RXRα, a RXRβ, or a RXRγ in a manner that elicits gene transcription via an RXR response element. As used herein, the term "selectively binds," when made in reference to a RXR agonist, refers to the discriminatory binding of a RXR agonist to the indicated target receptor like a RXRα, a RXRβ, or a RXRγ such that the RXR agonist does not substantially bind with non-target receptors like a RARα, a RARβ or a RARγ.

In one embodiment, the selective RXR agonist does not activate to any appreciable degree the permissive heterodimers PPAR/RXR, FXR/RXR, and LXR/RXR. In another embodiment, the RXR agonist activates the permissive heterodimer Nurr1/RXR. One example of such a selective RXR agonist is an ester of 3,7-dimethyl-6(S),7(S)-methano, 7-[1,1,4,4-tetramethyl-1,2,3,4-tetrahydronaphth-7-yl]2(E),4 (E) heptadienoic acid (IRX4204) disclosed herein, the structure of which is shown in Formula III. In other aspects of this embodiment, the RXR agonist activates the permissive heterodimers PPAR/RXR, FXR/RXR, or LXR/RXR by 1% or less, 2% or less, 3% or less, 4% or less, 5% or less, 6% or less, 7% or less, 8% or less, 9% or less, or 10% or less relative to the ability of an activating RXR agonist to activate the same permissive heterodimer. Examples of RXR agonists which activates one or more of PPAR/RXR, FXR/RXR, or LXR/RXR include, e.g., LGD1069 (bexarotene) and LGD268.

IRX4204 like some other RXR ligands, does not activate non-permissive heterodimers such as RAR/RXR. However, IRX4204 is unique in that it specifically activates the Nurr1/RXR heterodimer and does not activate other permissive RXR heterodimers such as PPAR/RXR, FXR/RXR, and LXR/RXR. Other RXR ligands generally activate these permissive RXR heterodimers. Thus, all RXR ligands cannot be classified as belonging to one class. IRX4204 belongs to a unique class of RXR ligands which specifically activate RXR homodimers and only one of the permissive RXR heterodimers, namely the Nurr1/RXR heterodimer. This unique receptor profile enables IRX4204 to have both immunomodulatory and neural repair properties. Thus, the use of specific RXR homodimer, Nurr1/RXR activators, such as IRX4204, provides a uniquely effective ways of treating nervous system disorders.

Binding specificity is the ability of a RXR agonist to discriminate between a RXR receptor and a receptor that does not contain its binding site, such as, e.g., a RAR receptor.

More specifically, disclosed herein are esters of RXR agonists. An ester may be derived from a carboxylic acid of C1, or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where the alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc. The various subsets and combinations of these esters are contemplated as further distinct embodiments, including straight-chain, branched, and/or cyclic moieties of any length or set of lengths within the $C_{1-6}$ alkyl genus.

Thus, disclosed herein are esters of RXR agonists having the structure of formula I:

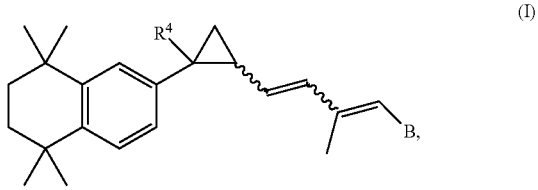

(I)

where $R^4$ is lower alkyl of 1 to 6 carbons; B is —COOR$^8$ where $R^8$ is lower alkyl of 1 to 6 carbons, and the configuration about the cyclopropane ring is cis, and the configuration about the double bonds in the pentadienoic acid or ester chain attached to the cyclopropane ring is trans in each of the double bonds.

In an exemplary embodiment, an ester of a RXR agonist is a compound having the structure of formula II:

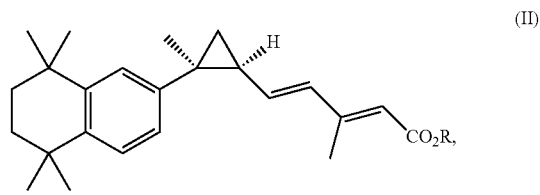

(II)

wherein R is lower alkyl of 1 to 6 carbons.

In a further exemplary embodiment, an ester of a RXR agonist is 3,7-dimethyl-6(S),7(S)-methano,7-[1,1,4,4-tetramethyl-1,2,3,4-tetrahydronaphth-7-yl]2(E),4(E) heptadienoic ethyl ester (IRX4204EE), and has the structure of formula III:

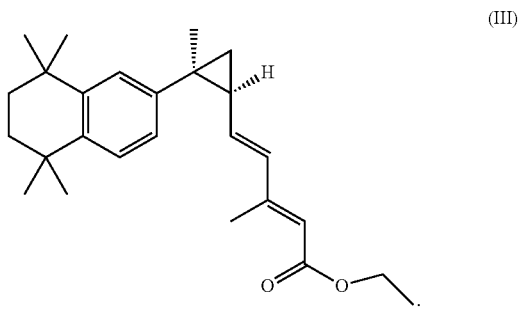 [SMILES: CCOC(=O)/C=C(C)/C=C/[C@@H]1C[C@]1(C)c1ccc2c(c1)C(C)(C)CCC2(C)C]

(III)

In certain embodiments, the free acid form of IRX4204, 3,7-dimethyl-6(S),7(S)-methano,7-[1,1,4,4-tetramethyl-1,2,3,4-tetrahydronaphth-7-yl]2(E),4(E) heptadienoic acid, is not within the scope of the present disclosure.

In certain embodiments, the ester of a RXR agonist is an ester of bexarotene (TARGRETIN®, 4-[1-(3,5,5,8,8-pentamethyl-6,7-dihydronaphthalen-2-yl)ethenyl]benzoic acid, LGD1069, Mylan Pharmaceuticals, Inc.) which has the structure of formula IV:

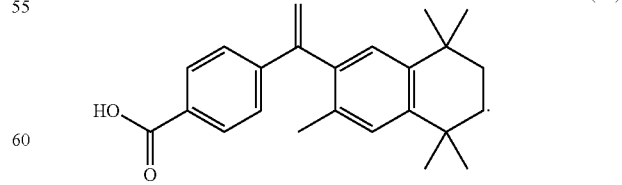

(IV)

In other embodiments, the ester of a RXR agonist is an ester of LG268 (LG100268, 2-[1-(3,5,5,8,8-pentamethyl-5,6,7,8-tetrahydro-2-naphthyl)cyclopropyl]pyridine-5-carboxylic acid) which has the structure of formula V:

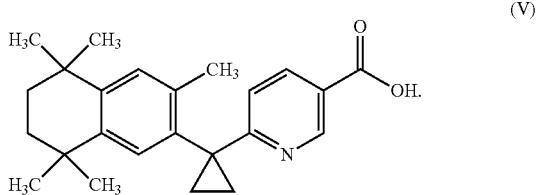 [SMILES: Cc1cc2c(cc1C1(c3ccc(C(=O)O)cn3)CC1)C(C)(C)CCC2(C)C]

(V)

As disclosed herein, an ester of a RXR agonist increases myelination in the central or peripheral nervous system by at least about 10% to at least about 25%, at least about 10% to at least about 50%, at least about 10% to at least about 75%, at least about 10% to at least about 100%, at least about 10% to at least about 200%, at least about 10% to at least about 300%, at least about 10% to at least about 400%, at least about 10% to at least about 500%, at least about 25% to at least about 50%, at least about 25% to at least about 75%, at least about 25% to at least about 100%, at least about 25% to at least about 200%, at least about 25% to at least about 300%, at least about 25% to at least about 400%, at least about 25% to at least about 500%, at least about 50% to at least about 100%, at least about 50% to at least about 200%, at least about 50% to at least about 300%, at least about 50% to at least about 400%, or at least about 50% to at least about 500%, relative to myelination levels in the absence of treatment with the ester of a RXR agonist.

In yet other aspects of this embodiment, an ester of a RXR agonist increases differentiation of oligodendrocyte progenitor cell differentiation into oligodendrocytes in the central or peripheral nervous system by at least about 10% to at least about 25%, at least about 10% to at least about 50%, at least about 10% to at least about 75%, at least about 10% to at least about 100%, at least about 10% to at least about 200%, at least about 10% to at least about 300%, at least about 10% to at least about 400%, at least about 10% to at least about 500%, at least about 25% to at least about 50%, at least about 25% to at least about 75%, at least about 25% to at least about 100%, at least about 25% to at least about 200%, at least about 25% to at least about 300%, at least about 25% to at least about 400%, at least about 25% to at least about 500%, at least about 50% to at least about 100%, at least about 50% to at least about 200%, at least about 50% to at least about 300%, at least about 50% to at least about 400%, or at least about 50% to at least about 500%, relative to differentiation levels in the absence of treatment with the ester of a RXR agonist.

In yet another aspect of the present specification, an ester of a RXR agonist increases the rate of myelin repair in the central nervous system by at least about 10% to at least about 25%, at least about 10% to at least about 50%, at least about 10% to at least about 75%, at least about 10% to at least about 100%, at least about 10% to at least about 200%, at least about 10% to at least about 300%, at least about 10% to at least about 400%, at least about 10% to at least about 500%, at least about 25% to at least about 50%, at least about 25% to at least about 75%, at least about 25% to at least about 100%, at least about 25% to at least about 200%, at least about 25% to at least about 300%, at least about 25% to at least about 400%, at least about 25% to at least about 500%, at least about 50% to at least about 100%, at least about 50% to at least about 200%, at least about 50% to at least about 300%, at least about 50% to at least about 400%, or at least about 50% to at least about 500%, relative to myelin repair rates in the absence of treatment with the ester of a RXR agonist.

Aspects of the present specification provide, in part, a composition comprising an ester of a RXR agonist. Exemplary esters of RXR agonists are IRX4204 ethyl ester (IRX4204EE), an ester of bexarotene, and an ester of LG268.

In certain embodiments, the nervous system disorder is a central nervous system disorder, such as relapsing/remitting, primary progressive, and secondary progressive forms of multiple sclerosis (MS), diffuse white matter injury in preterm infants, neuromyelitis optica, acute disseminated encephalomyelitis, Marburg multiple sclerosis, diffuse myelinoclastic sclerosis (Schilder's disease), Balo concentric sclerosis, solitary sclerosis, optic neuritis, transverse myelitis, amyotrophic lateral sclerosis (ALS), leukodystrophy (multiple variants, e.g. adrenoleukodystrophy, adrenomyeloneuropathy), Parkinson's disease, Alzheimer's disease, progressive supranuclear palsy, stroke, seizure disorders, CNS trauma including traumatic brain injury and traumatic spinal cord injury, radiation induced neuroinflammation, radiation somnolence syndrome, Devic's disease, inflammatory demyelinating diseases, CNS neuropathies, central pontine myelinolysis, Tabes dorsalis (syphilitic myelopathy), progressive multifocal leukoencephalopathy, leukodystrophy, depression, schizophrenia, epilepsy, dementias, and cachexia related to cancer, AIDS, chronic kidney disease, and advanced age.

In certain embodiments, the central nervous system disorder is a demyelination-related disorder such as multiple sclerosis, radiation-induced central nervous system inflammation, Alzheimer's disease or Parkinson's disease.

In certain embodiments, the nervous system disorder is a peripheral nervous system disorder such as Guillain-Barré Syndrome, acute inflammatory demyelinating polyneuropathy, chronic inflammatory demyelinating polyneuropathy, demyelinating diabetic neuropathy, progressive inflammatory neuropathy, drug- or toxin-induced neuropathy, such as chemotherapy-induced neuropathy or organophosphate-induced neuropathy, anti-MAG peripheral neuropathy, Charcot-Marie-Tooth Disease, or copper deficiency.

In certain embodiments the RXR agonist esters are used to provide RXR agonists for the treatment of muscular or autoimmune disorders. The use of RXR agonists in the treatment of muscular disorders is explained in greater detail in WO 2017/155578 which is incorporated by reference herein for all that it teaches about the use of RXR agonists in treating muscular disorders. The use of RXR agonists in the treatment of autoimmune disorders is explained in greater detail in WO 2017/155577 which is incorporated by reference herein for all that it teaches about the use of RXR agonists in treating autoimmune disorders. The activation of retinoic acid receptors (RAR) by non-selective Retinoic X Receptor (RXR) agonists decreases the efficacy of the RXR agonists such as in muscular and autoimmune disorders. As such, the efficacy of RXR agonists in these and other disorders can be improved by administering the RXR agonist at a dose which activates RXR but which activates RAR minimally or not at all. Administration of the herein described RXR agonist esters can be used to provide the RXR agonist at a dose which specifically activates only RXRs gives optimal activity against disorders such as muscular disorders and autoimmune disorders, either alone or when combined with administration of a thyroid hormone. Further disclosed are methods comprising providing to an individual in need thereof a therapeutically effective amount of a RXR agonist by administering and ester of the RXR agonist and one or more thyroid hormones, wherein the RXR agonist and thyroid hormone treat the disorder in the individual more effectively than treatment with the ester of the RXR agonist or thyroid hormone alone.

In some embodiments of treating a muscular disorder, the method treats a muscle wasting disorder selected from the group consisting of acid maltase deficiency, atony, atrophy, ataxia, Becker Muscular Dystrophy (BMD), cardiac muscle ischemia, cardiac muscle infarction, a cardiomyopathy, carnitine deficiency, carnitine palmitoyltransferase deficiency, Central Core Disease (CCD), centronuclear (myotubular) myopathy, cerebral palsy, compartment syndromes, channelopathies, Congenital Muscular Dystrophy (CMD), corticosteroid myopathy, cramps, dermatomyositis, distal muscular dystrophy, Duchenne Muscular Dystrophy (DMD), dystrophinopathies, Emery-Dreifuss Muscular Dystrophy (EDMD), Facioscapulohumeral Muscular Dystrophy (FSHD), fibromyalgia, fibrositis, Limb Girdle Muscular Dystrophy (LGMD), McArdle syndrome, muscular dystrophy, muscle fatigue, myasthenia gravis, myofascial pain syndrome, myopathy, myotonia, Myotonic Muscular Dystrophy type 1, Myotonic Muscular Dystrophy type 2, Nemaline myopathy, Oculopharyngeal Muscular Dystrophy (OCM), myoglobinuria, paramyotonia congenita (Eulenberg's disease), polymyositis, rhabdomyolysis, sarcoglycanopathies, or spasms.

In some embodiments, the muscular disorder is a myopathy such as dermatomyositis, inclusion body myositis, or polymyositis.

In certain embodiments, the muscular disorder is due to cancers, HIV/AIDS, COPD, chronic steroid use, fibromyalgia, or skeletal muscle myopathies.

In other embodiments, the combination of rexinoids and thyroid hormones are beneficial by effecting heart muscle protection or regeneration either in vivo, or in vitro for subsequent implantation of myocytes into damaged cardiac muscle.

In certain embodiments for treating an autoimmune disorder, the methods treats an autoimmune disease selected from the group consisting of acute disseminated encephalomyelitis (ADEM), Addison's disease, an allergy, allergic rhinitis, anti-phospholipid antibody syndrome (APS), an arthritis, asthma, acquired immunodeficiency syndrome (AIDS), autoimmune hemolytic anemia, autoimmune hepatitis, autoimmune inner ear disease, bullous pemphigoid, celiac disease, Chagas disease, chronic obstructive pulmonary disease (COPD), diabetes mellitus type 1 (IDDM), endometriosis, a gastrointestinal disorder, a glomerulonephritis, Goodpasture's syndrome, Graves' disease, Guillain-Barré syndrome (GBS), Hashimoto's thyroiditis, hidradenitis suppurativa, idiopathic thrombocytopenic purpura, interstitial nephritis, interstitial cystitis, a lupus, morphea, multiple sclerosis (MS), myasthenia gravis, a myopathy, myositis, narcolepsy, neuromyotonia, pemphigus vulgaris, pernicious anaemia, primary biliary cirrhosis, psoriasis, psoriatic arthritis, a pulmonary fibrosis, recurrent disseminated encephalomyelitis, rheumatic fever, schizophrenia, scleroderma, Sjögren's syndrome, a skin disorder, tenosynovitis, uveitis, a vasculitis, or vitiligo.

In certain embodiments, the disease is not multiple sclerosis.

In certain embodiments, the arthritis is monoarthritis, oligoarthritis, polyarthritis, osteoarthritis, rheumatoid arthritis, juvenile idiopathic arthritis, septic arthritis, spondyloarthropathy, gout, pseudogout, or Still's disease.

In some embodiments, the gastrointestinal disorder is an irritable bowel disease or an inflammatory bowel disease. In other embodiments, the inflammatory bowel disease is Crohn's disease or ulcerative colitis.

In some embodiments, the lupus is discoid lupus erythematosus, drug-induced lupus erythematosus, lupus nephritis, neonatal lupus, subacute cutaneous lupus erythematosus, or systemic lupus erythematosus.

In some embodiments, the autoimmune dis order is a myopathy with an autoimmune component such as dermatomyositis, inclusion body myositis, or polymyositis.

In some embodiments, the skin disorder is dermatitis, eczema, statis dermatitis, hidradenitis suppurativa, psoriasis, rosacea, or scleroderma.

In some embodiments, the vasculitis is Buerger's disease, cerebral vasculitis, Churg-Strauss arteritis, cryoglobulinemia, essential cryoglobulinemic vasculitis, giant cell arteritis, Golfer's vasculitis, Henoch-Schonlein purpura, hypersensitivity vasculitis, Kawasaki disease, microscopic polyarteritis/polyangiitis, polyarteritis nodosa, polymyalgia rheumatica (PMR), rheumatoid vasculitis, Takayasu arteritis, or Wegener's granulomatosis.

In yet other embodiments, the autoimmune disease is multiple sclerosis, psoriasis, rheumatoid arthritis, glomerulonephritis, pulmonary fibrosis, interstitial nephritis, or an inflammatory bowel disease.

As used herein "therapeutically effective" means that measurable medical benefit is achieved. Such medical benefit can include slowing, halting, or reversing any pathophysiological process of the disease or disorder, up to and including cure, whether permanently or temporarily. It can also include a diminution in the occurrence, frequency, or severity of any symptom associated with the disease or disorder being treated.

In some embodiments, the therapeutically effective amount of the RXR agonist is about 0.001 mg/day to about 100 mg/day. In some embodiments, the therapeutically effective amount of the RXR agonist is about 0.1 mg/day to about 10 mg/day. In some embodiments, the RXR agonist is administered by nasal administration. In some embodiments, the RXR agonist is administered orally. The esters can be administered at similar or the same dosages. However, because conversion of the esters into the active form takes time, a lower Cmax of the active form is generally observed to result from administration of the esters for any particular dosage. Cmax, that is maximum concentration, is most often measured in the blood (the actual measurement is often carried out in plasma although serum could be used as an alternative), however Cmax in a target tissue, for example, brain tissue, can also be specified. Thus in some embodiments it will be possible or desirable to administer the ester at a higher dosage, for example a 2- to 10-fold higher dosage. As conversion to the active species is required for activity, the esters can be administered at higher dosages while avoiding toxicities related to similar dosages of the free acid. That is the esters can have a higher maximum tolerated dose (MTD); the highest dose that will the desired therapeutic effect without producing unacceptable toxicity such as suppression of thyroid hormone production and elevation of triglyceride levels. The esters can also exhibit a better therapeutic index, the ratio of a toxic or lethal dose to an effective dose, than the free acid. Most typically therapeutic index is calculated as the ratio of $LD_{50}:ED_{50}$ when based on animal studies and $TD_{50}:ED_{50}$ when based on studies in humans (though this calculation could also be derived from animal studies and is sometime called the protective index), where $LD_{50}$, $TD_{50}$, and $ED_{50}$ are the doses that are lethal, toxic, and effective in 50% of the tested population, respectively. The esters can also exhibit a broadened therapeutic window as compared to the free acid, that is, the dose range from the lowest dose that exhibits a detectable therapeutic effect up to the MTD.

Thus in various embodiments the esters can be administered at a higher dosage than a toxicity producing dosage of the free acid. In various aspects of these embodiments the toxicity is an observable toxicity, a substantial toxicity, a severe toxicity, or an acceptable toxicity, or a dose-limiting toxicity (such as but not limited to a MTD). By an observable toxicity it is meant that while a change is observed the effect is negligible or mild. By substantial toxicity it is meant that there is a negative impact on the patient's overall health or quality of life. In some instances a substantial toxicity may be mitigated or resolved with other ongoing medical intervention. By a severe toxicity it is meant that the effect requires acute medical intervention and/or dose reduction or suspension of treatment. The acceptability of the toxicity will be influenced by the particular disease being treated and it severity and the availability of mitigating ongoing medical intervention.

Toxicities and adverse events are sometimes graded according to a 5 point scale. A grade 1 or mild toxicity is asymptomatic or induces only mild symptoms; may be characterized by clinical or diagnostic observations only; and intervention is not indicated. A grade 2 or moderate toxicity may impair activities of daily living (such as preparing meals, shopping, managing money, using the telephone, etc.) but only minimal, local, or non-invasive interventions are indicated. Grade 3 toxicities are medically significant but not immediately life-threatening; hospitalization or prolongation of hospitalization is indicated; activities of daily living related to self-care (such as bathing, dressing and undressing, feeding oneself, using the toilet, taking medications, and not being bedridden) may be impaired. Grade 4 toxicities are life-threatening and urgent intervention is indicated. Grade 5 toxicity produces an adverse event-related death. Thus in various embodiments, use of an RXR agonist ester reduces the grade of a toxicity associated with treatment by at least one grade as compared to use of a similar dosage of the RXR agonist free acid. In other embodiments use of an RXR agonist ester confines a toxicity to grade 2 or less, to grade 1 or less, or produces no observation of the toxicity.

While retinoids and rexinoids are often described as selective, meaning they agonize a particular receptor type or sub-type, such designations are typically not absolute. Thus bexarotene is sometimes described in the literature as an RXR-selective agonist although it has measurable agonist activity for RAR as well. Some of the adverse effects of bexarotene can be attributed to this off-target activity. However, a lowering of Cmax, as can be achieved with an ester, will facilitate maintaining effective concentrations of the drug for activating RXR without crossing the concentration threshold that also activates RAR. Thus the range of doses of an ester of an RXR agonist that can be administered the lead to a concentration in the body or target tissue that exceeds an effective concentration for activating RXR but does not exceed a concentration that activates RAR is broader than for the RXR agonist itself. This increased range of acceptable dosage means that dosage needs to be less precisely matched to patient size (e.g., mass or surface area) and that there will be a greater distinction between effective and toxic doses. Problems with toxicity have limited the clinical use of bexarotene. Thus in various embodiments a therapeutically effective amount of a bexarotene ester has reduced severity or incidence of RAR-associated toxicity than a therapeutically effective amount of bexarotene itself. This can be expected to not only increase safety in the treatment of conditions for which bexarotene is currently used, but also to enable use of a bexarotene ester in the use of additional conditions. LG268 has posed even greater toxicity issues than bexarotene and has yet to be developed into a clinically useful drug. An LG268 ester could reduce RAR-associated toxicity to enable clinical use. Thus in various embodiments a therapeutically effective amount of a LG268 ester has reduced severity or incidence of RAR-associated toxicity than a therapeutically effective amount of LG268 itself. Additionally, the lower dosages of the esters needed to maintain therapeutic concentrations in the body may also reduce rexinoid-induced hypothyroidism.

IRX4204 is more selective for RXR over RAR (about 200- to 2000-fold) than is bexarotene (about 2-fold), but such selectivity factors should still be considered with respect to the prospect of inducing RAR-mediated toxicity. The $EC_{90}$ of IRX4204 with RXRα, β, and γ, is about 0.1, 1, and 0.1 nM, respectively, while the $EC_{10}$ of IRX4204 with RARα, β, and γ, is about 300, 200, and 200 nM, respectively. Thus in various embodiments an IRX4204 ester, for example, the ethyl ester, is administered in a dose that produces a systemic concentration of IRX4204, or a concentration of IRX4204 in a target tissue, such as the nervous system, brain, or a tumor, of at least 0.1 nM, or 1 nM (about 35 or 352 μg/ml). However, concentrations as low as 50 pM can promote remyelination, so other embodiments include doses of the ester that produce concentrations systemically or in a target tissue that meet or exceed that concentration. In a further aspect of these embodiments the IRX4204 ester can be administered at a dose that produces a systemic concentration of IRX4204, or a concentration of IRX4204 in a target tissue, such as the nervous system, brain, or a tumor, that does not exceed 200 nM or 300 nM. Systemic concentration is most commonly determined in the blood (plasma or serum). By so confining concentrations of IRX4204 to these ranges one or more toxicities or adverse effects associated with activation of RAR can be reduced or avoided. Using standard dose conversion conventions and the results presented in Example 9 below, a human dose of 0.04 mg/m$^2$ (about 0.07 mg) can be expected to provide a concentration in a target tissue of about 0.1 nM at a late time after Tmax, but have a systemic Cmax (with IV administration) below a RAR activating dose. IV administration will generally overestimate Cmax achieved with other routes of administration. In experiments with IRX4204 it was observed that oral doses of 24 mg/m$^2$/day produced a Cmax of 219 nM, thus dosages of ≤20 mg/m$^2$/day were preferred. Dosages of IRX4204 3, 4, 5, or 6-fold higher may also avoid a Cmax that would be sufficient to even minimally activate RAR and thus potentially induce RAR-associated toxicities.

The esters also persist in the body for a longer period of time than the free acid and they continue to be converted to the active species throughout that time. Thus the active species is present in the body, both in circulation and in target tissues, such as brain tissue, for a prolonged period of time. In other words, administration of the ester will lead to elevated levels of the active species at late times after Tmax as compared to administration of a corresponding dose of the active species itself. In some embodiments, the elevated level of the active species due to administration of the ester becomes apparent at 1, 2, 3, 4, or more hours after Tmax. As a result it can be possible to administer the esters less frequently than the free acid form. For example, the free acid form could be administered once or twice a day while esters could be administered once a day, once every two days, once every three days, once every 4, 5, 6, or 7 days. Also as a result Tmax for the active species, the time after administration that Cmax for the active species is achieved, can be greater.

Some embodiments are methods of providing (a dose of) a RXR agonist, according to structure I, II, III, IV, or V or any individual species or subgenus encompassed therein, to a patient in need thereof, by administering an ester of the RXR agonist to a mammal. (In referring to these RXR agonist structures it is not intended to distinguish between the free acid and the dissociated anionic form found in aqueous solution.) In aspects of these embodiments the Cmax of the RXR agonist following administration of the ester is less than the Cmax of the RXR agonist following administration of the RXR agonist at the same dosage by the same route of administration. In various embodiments the Cmax of the RXR agonist following administration of the ester is ≤50%, ≤40%, ≤30%, ≤25%, ≤20%, ≤18% the Cmax of the RXR agonist following administration of the RXR agonist itself. In a further aspect of these embodiments the efficacy of treatment is not substantially reduced.

In other aspects of these embodiments for providing (a dose of) a RXR agonist by administering an ester of the RXR agonist the ester is administered at a dosage exceeding the MTD of the RXR agonist. In various embodiments the dosage of the ester exceeds the MTD by 10%, 20%, 30%, 40%, 50%, and so on to 500%.

In other aspects of these embodiments for providing (a dose of) a RXR agonist by administering an ester of the RXR agonist, the concentration of the RXR agonist in a body tissue of a mammal is initially less than the concentration of the RXR agonist in the body tissue of the mammal following administration of the same dosage of the RXR agonist itself but is equal or greater at a later time and wherein the equal or greater concentration is a therapeutically effective concentration. In various embodiments a later time is 3, 4, 5, 6, 8, 10, 12, or more hours post-administration. In various embodiments the therapeutically effective concentration in the body tissue is ≥10 pM, ≥100 pM, ≥200 pM, ≥500 pM, or ≥1000 pM. In various embodiments the body tissue is blood, brain, spinal cord, peripheral nerves, or tumor tissue.

In other aspects of these embodiments for providing (a dose of) a RXR agonist by administering an ester of the RXR agonist, the occurrence of a toxicity or an undesirable side-effect is avoided or reduced in severity or frequency as compared to the occurrence of the toxicity or the undesirable side-effect associated with the administration of the same dose of RXR agonist itself. In a further aspect of these embodiments the efficacy of treatment is not substantially reduced. In particular embodiments the undesirable side-effect is the suppression or reduction thyroid hormone levels, induction of hypothyroidism, or the elevation of triglyceride levels.

In some embodiments of the foregoing methods the dosage comparison is made on a weight-to-weight basis. In distinct embodiments the dosage comparison is made on a mole-to-mole basis. In some embodiments the Cmax or other concentration comparison is made on the basis of mass concentrations. In distinct embodiments the Cmax or other concentration comparison is made on the basis of molar concentrations. In still further embodiments comparison is made on the basis of the administration of similar dosages with the difference in molecular weight between a RXR agonist and its ester being neglected. In any of the foregoing embodiments the ester can be a $C_{1-6}$ alkyl ester. In particular embodiments the $C_{1-6}$ alkyl ester is the ethyl ester. In the foregoing methods the mammal can be variously a mouse, a rat, a dog, or a human.

Any of the foregoing embodiments may further be incorporated into a method of treating a disease or disorder for which the RXR agonist is therapeutically effective, especially such diseases or disorders as are herein disclosed, wherein the dose of the RXR agonist is provided as described above. Similarly, in any of the foregoing embodiments the patient in need thereof may be further identified as having a particular disease or disorder for which the RXR agonist is therapeutically effective, especially such diseases or disorders as are herein disclosed, Further parallel embodiments related to the foregoing methods of providing (a dose of) a RXR agonist by administering an ester of the RXR agonist include uses of the ester of the RXR agonist to provide (a dose of) the RXR agonist, compositions of the ester of the RXR agonist to provide (a dose of) the RXR agonist, and use of the ester of the RXR agonist in the manufacture of a medicament for providing (a dose of) the RXR agonist. Any of these uses may be limited to providing the dose of the RXR agonist in a context of treating a disease or disorder for which the RXR agonist is therapeutically effective, especially such diseases or disorders as are herein disclosed.

As used herein The term "treating" or "treatment" broadly includes, both collectively and as individual embodiments, any kind of treatment activity, including the diagnosis, mitigation, or prevention of disease in man or other animals, or any activity that otherwise affects the structure or any function of the body of man or other animals. Treatment activity includes the administration of the medicaments, dosage forms, and pharmaceutical compositions described herein to a patient, especially according to the various methods of treatment disclosed herein, whether by a healthcare professional, the patient his/herself, or any other person. Treatment activities include the orders, instructions, and advice of healthcare professionals such as physicians, physician's assistants, nurse practitioners, and the like that are then acted upon by any other person including other healthcare professionals or the patient his/herself. In some embodiments, treatment activity can also include encouraging, inducing, or mandating that a particular medicament, or combination thereof, be chosen for treatment of a condition—and the medicament is actually used—by approving insurance coverage for the medicament, denying coverage for an alternative medicament, including the medicament on, or excluding an alternative medicament, from a drug formulary, or offering a financial incentive to use the medicament, as might be done by an insurance company or a pharmacy benefits management company, and the like. In some embodiments, treatment activity can also include encouraging, inducing, or mandating that a particular medicament be chosen for treatment of a condition—and the medicament is actually used—by a policy or practice standard as might be established by a hospital, clinic, health maintenance organization, medical practice or physicians group, and the like.

In certain embodiments, treatment with an ester of a RXR agonist reduces at least one symptom of the nervous system disorder, wherein the at one symptom reduced is inflammation, fatigue, dizziness, malaise, elevated fever and high body temperature, extreme sensitivity to cold in the hands and feet, weakness and stiffness in muscles and joints, weight changes, digestive or gastrointestinal problems, low or high blood pressure, irritability, anxiety, or depression, blurred or double vision, ataxia, clonus, dysarthria, fatigue, clumsiness, hand paralysis, hemiparesis, genital anesthesia, incoordination, paresthesias, ocular paralysis, impaired muscle coordination, weakness (muscle), loss of sensation, impaired vision, neurological symptoms, poor short-term memory, long-term memory loss, confusion, hallucinations, delusions, paranoia, impaired reasoning or judgement, unsteady gait, spastic paraparesis, incontinence, hearing problems, or speech problems. In some embodiments, treatment with an ester of a RXR agonist reduces at least two symptoms of the nervous system disorder. In some embodiments, treatment with an ester of a RXR agonist reduces at least five symptoms of the nervous system disorder.

Also disclosed herein are methods of treating cancer by administering an ester of a RXR agonist to a subject in need thereof. Use of RXR agonists in the treatment of cancer is also disclosed in co-pending U.S. provisional application 62/249,219 filed Oct. 31, 2015, which is incorporated by reference for all it discloses regarding use of RXR agonists for the treatment of cancer. In the case of cancer treatment, the RXR agonists act as inhibitors of cancer cell proliferation. Concentrations of 10 nM IRX4204 observably inhibit the proliferation of breast cancer cells in vitro; lower concentrations were not tested. A substantial improvement in effectiveness was seen at 100 nM, but little increased effect beyond that.

Examples of cancers which can be treated by the disclosed methods may include, but are not limited to, acute lymphoblastic leukemia; acute myeloid leukemia, adrenocortical carcinoma; AIDS-related lymphoma; AIDS-related malignancies; anal cancer; bile duct cancer; bladder cancer; bone cancer, brain stem glioma; brain tumor (e.g., astrocytoma, cerebellar astrocytoma; cerebral astrocytoma/malignant glioma; pendymoma brain tumor; supratentorial primitive brain tumor; neuroectodermal tumors; visual pathway and hypothalamic glioma, etc.); breast cancer; bronchial adenomas/carcinoids; carcinoid tumor; carcinoma (adrenocortical; gastrointestinal; islet cell; skin, unknown primary, etc.); cervical cancer; childhood cancers; chronic lymphocytic leukemia; chronic myelogenous leukemia; chronic myeloproliferative disorders; clear cell sarcoma of tendon sheaths; colon cancer; colorectal cancer; cutaneous T-cell lymphoma; endometrial cancer, ependymoma; epithelial cancer; esophageal cancer; Ewing family of tumors; extracranial germ cell tumor; extragonadal germ cell tumor; extrahepatic bile duct cancer; eye cancer, intraocular melanoma; gallbladder cancer; gastric (stomach) cancer; gastrointestinal carcinoid tumor; ovarian germ cell tumor; gestational trophoblastic tumor; hairy cell leukemia; head and neck cancer; hepatocellular (liver) cancer; Hodgkin's lymphoma; hypopharyngeal cancer; islet cell carcinoma (endocrine pancreas); Kaposi's sarcoma; kidney cancer; laryngeal cancer; lip and oral cavity cancer; primary liver cancer; lung cancer, non-small cell lung cancer; small cell lung cancer; primary central nervous system lymphoma; Non-Hodgkin's lymphoma; Waldenstrom's macroglobulinemia; malignant mesothelioma; malignant thymoma; medulloblastoma; melanoma; Merkel cell carcinoma; primary metastatic squamous neck cancer with occult; multiple endocrine neoplasia syndrome; multiple myeloma/plasma cell neoplasm; mycosis fungoides; myelodysplastic syndromes; multiple myeloma; nasal cavity and paranasal sinus cancer; nasopharyngeal cancer; neuroblastoma; oral cancer; oropharyngeal cancer; ovarian epithelial cancer; ovarian low malignant potential tumor; pancreatic cancer; parathyroid cancer; pheochromocytoma penile cancer; pineal and supratentorial primitive neuroectodermal tumors; pituitary tumor; pleuropulmonary blastoma; prostate cancer; rectal cancer; renal cell (kidney) cancer; renal pelvis and ureter, transitional cell cancer; retinoblastoma; rhabdomyosarcoma; salivary gland cancer; sarcoma (e.g., Ewing's family of tumors, Kaposi's; (osteosarcoma)/malignant fibrous histiocytoma of bone, soft tissue, etc.); Sezary syndrome; skin cancer; small intestine cancer; testicular cancer; thymoma; thyroid cancer; trophoblastic tumor; vaginal cancer; vulvar cancer; or Wilms' Tumor. In other embodiments, the method may treat lung cancers, prostate cancer, breast cancer, and pancreatic cancer.

There are two standard methods for the evaluation of oncology treatment response: the WHO and RECIST standards. These methods measure a tumor to compare a current tumor with past measurements or to compare changes with future measurements and make to make changes in a treatment regimen. In the WHO method, the tumor's long and short axes are measured and the product of these two measurements is then calculated; if there are multiple tumors, the sum of all the products is calculated. In the RECIST method, only the long axis is measured. If there are multiple tumors, the sum of all the long axes measurements is calculated. However, with lymph-nodes, the short axis is measured instead of the long axis.

In some embodiments of the current method, the tumor size of a treated patient is reduced by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any other range bound by these values.

In other embodiments, the 1-year survival rate of treated individual is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any other range bound by these values.

In other embodiments, the 5-year survival rate of treated individual is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any other range bound by these values.

In other embodiments, the 10-year survival rate of treated individual is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any other range bound by these values In other embodiments, the method may help to treat or alleviate conditions, symptoms, or disorders related to cancer. In some embodiments, these conditions or symptoms may include, but are not limited to, anemia, asthenia, cachexia, Cushing's Syndrome, fatigue, gout, gum disease, hematuria, hypercalcemia, hypothyroidism, internal bleeding, hair loss, mesothelioma, nausea, night sweats, neutropenia, paraneoplastic syndromes, pleuritis, polymyalgia rheumatica, rhabdomyolysis, stress, swollen lymph nodes, thrombocytopenia, Vitamin D deficiency, or weight loss.

Aspects of the methods of the present disclosure include, in part, treatment of a subject. A subject includes a mammal, such as a human, and a human can be a patient. Other aspects of the present disclosure provide, in part, an individual. An individual includes a mammal and a human, and a human can be a patient.

RXR agonists are known to suppress thyroid function. Treatment of human subjects with the specific rexinoid IRX4204 results first in a reduction in plasma levels of TSH followed by a reduction in circulating thyroxine levels. If a patient on IRX4204 develops adverse clinical symptoms due to the functional hypothyroidism, such clinical symptoms can be resolved by treatment of the patient with pharmacological doses of thyroxine. However supplementation of RXR agonist therapy with thyroid hormones has not been utilized therapeutically. Surprisingly, the combination of an RXR agonist and a thyroid hormone produces unexpectedly better efficacy that the use of RXR agonist alone, demonstrating synergism between the RXR agonist and thyroid hormone independent of regulation of plasma thyroid hormone levels. Therapeutic benefit in the treatment nervous system disorders can be derived at dosages of IRX4204 that generally do not suppress thyroid hormone to the point that the recipient is no longer euthyroid. The flatter kinetic profile achievable with esters of RXR agonists facilitates achieving therapeutic concentrations of RXR agonists without their concentration attaining toxicity inducing levels. In some embodiments hypothyroidism is assessed based on symptomology. Symptoms of hypothyroidism can include fatigue, weakness, weight gain or difficulty losing weight, dry hair or skin, hair loss, sensitivity to cold, muscle cramps and aches, constipation, depression, irritability, memory loss, abnormal menstrual cycles, decreased libido, slowed speech, jaundice, and increased tongue size. In some embodiments hypothyroidism is assessed based on free thyroxine ($T_4$) level or total $T_4$ level, according to the normal standard range in the testing lab.

Aspects of the present disclosure include, in part, administering an ester of a RXR agonist, or a combination of an ester of an RXR agonist and thyroxine. As used herein, the term "administering" means any delivery mechanism that provides a compound, a composition, or a combination disclosed herein to an individual that potentially results in a clinically, therapeutically, or experimentally beneficial result.

An ester of an RXR agonist disclosed herein, or a composition comprising an ester of an RXR agonist, or a combination of an ester of an RXR agonist and thyroxine, is generally administered to an individual as a pharmaceutical composition. In some embodiments the ester of an RXR agonist and the thyroxine are contained in separate pharmaceutical compositions that may be administered together or at separate points in time. Pharmaceutical compositions may be prepared by combining a therapeutically effective amount of at least one ester of an RXR agonist, as an active ingredient, with conventional acceptable pharmaceutical excipients, and by preparation of unit dosage forms suitable for therapeutic use. As used herein, the term "pharmaceutical composition" refers to a therapeutically effective concentration of an active compound, such as, e.g., any of the compounds disclosed herein. Preferably, the pharmaceutical composition does not produce an adverse, allergic, or other untoward or unwanted reaction when administered to an individual. A pharmaceutical composition disclosed herein is useful for medical and veterinary applications. A pharmaceutical composition may be administered to an individual alone, or in combination with other supplementary active compounds, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir, or any other dosage form suitable for administration.

A pharmaceutical composition produced using the methods disclosed herein may be a liquid formulation, semi-solid formulation, or a solid formulation. A formulation disclosed herein can be produced in a manner to form one phase, such as, e.g., an oil or a solid. Alternatively, a formulation disclosed herein can be produced in a manner to form two phases, such as, e.g., an emulsion. A pharmaceutical composition disclosed herein intended for such administration may be prepared according to any method known to the art for the manufacture of pharmaceutical compositions.

Liquid formulations suitable for parenteral injection or for nasal sprays may comprise physiologically acceptable sterile aqueous or nonaqueous solutions, dispersions, suspensions or emulsions and sterile powders for reconstitution into sterile injectable solutions or dispersions. Formulations suitable for nasal administration may comprise physiologically acceptable sterile aqueous or nonaqueous solutions, dispersions, suspensions or emulsions. Examples of suitable aqueous and nonaqueous carriers, diluents, solvents or vehicles include water, ethanol, polyols (propylene glycol, polyethyleneglycol (PEG), glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

Pharmaceutical formulations suitable for administration by inhalation include fine particle dusts or mists, which may be generated by means of various types of metered, dose pressurized aerosols, nebulizers, or insufflators.

Semi-solid formulations suitable for topical administration include, without limitation, ointments, creams, salves, and gels. In such solid formulations, the active compound may be admixed with at least one inert customary excipient (or carrier) such as, a lipid and/or polyethylene glycol.

Solid formulations suitable for oral administration include capsules, tablets, pills, powders and granules. In such solid formulations, the active compound may be admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

In liquid and semi-solid formulations, a concentration of an ester of an RXR agonist typically may be between about 50 mg/mL to about 1,000 mg/mL. In aspects of this embodiment, a therapeutically effective amount of a therapeutic compound disclosed herein may be from, e.g., about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, or about 600 mg/mL to about 1,000 mg/mL.

In semi-solid and solid formulations, an amount of an ester of an RXR agonist typically may be between about 0.01% to about 45% by weight. In aspects of this embodiment, an amount of a therapeutic compound disclosed herein may be from, e.g., about 0.1% to about 45% by weight, about 0.1% to about 40% by weight, about 0.1% to about 35% by weight, about 0.1% to about 30% by weight, about 0.1% to about 25% by weight, about 0.1% to about 20% by weight, about 0.1% to about 15% by weight, about 0.1% to about 10% by weight, about 0.1% to about 5% by weight, about 1% to about 45% by weight, about 1% to about 40% by weight, about 1% to about 35% by weight, about 1% to about 30% by weight, about 1% to about 25% by weight, about 1% to about 20% by weight, about 1% to about 15% by weight, about 1% to about 10% by weight, about 1% to about 5% by weight, about 5% to about 45% by weight, about 5% to about 40% by weight, about 5% to about 35% by weight, about 5% to about 30% by weight, about 5% to about 25% by weight, about 5% to about 20% by weight, about 5% to about 15% by weight, about 5% to about 10% by weight, about 10% to about 45% by weight, about 10% to about 40% by weight, about 10% to about 35% by weight, about 10% to about 30% by weight, about 10% to about 25% by weight, about 10% to about 20% by weight, about 10% to about 15% by weight, about 15% to about 45% by weight, about 15% to about 40% by weight, about 15% to about 35% by weight, about 15% to about 30% by weight, about 15% to about 25% by weight, about 15% to about 20% by weight, about 20% to about 45% by weight, about 20% to about 40% by weight, about 20% to about 35% by weight, about 20% to about 30% by weight, about 20% to about 25% by weight, about 25% to about 45% by weight, about 25% to about 40% by weight, about 25% to about 35% by weight, or about 25% to about 30% by weight.

A pharmaceutical composition disclosed herein can optionally include a pharmaceutically acceptable carrier that facilitates processing of an active compound into pharmaceutically acceptable compositions. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. As used herein, the term "pharmacologically acceptable carrier" is synonymous with "pharmacological carrier" and refers to any carrier that has substantially no long term or permanent detrimental effect when administered and encompasses terms such as "pharmacologically acceptable vehicle, stabilizer, diluent, additive, auxiliary, or excipient." Such a carrier generally is mixed with an active compound or permitted to dilute or enclose the active compound and can be a solid, semi-solid, or liquid agent. It is understood that the active compounds can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., starch, magnesium stearate, mannitol, sodium saccharin, talcum, cellulose, glucose, sucrose, lactose, trehalose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active compound, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, $7^{th}$ ed. 1999); Remington: The Science and Practice of Pharmacy (Alfonso R. Gennaro ed., Lippincott, Williams & Wilkins, $20^{th}$ ed. 2000); Goodman & Gilman's The Pharmacological Basis of Therapeutics (Joel G. Hardman et al., eds., McGraw-Hill Professional, $10^{th}$ ed. 2001); and Handbook of Pharmaceutical Excipients (Raymond C. Rowe et al., APhA Publications, $4^{th}$ edition 2003). These protocols are routine and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, borate buffers, citrate buffers, phosphate buffers, neutral buffered saline, and phosphate buffered saline. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole, and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., sodium chlorite and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

The compounds disclosed herein, such as a combination of an RXR agonist and thyroxine, may also be incorporated into a drug delivery platform in order to achieve a controlled compound release profile over time. Such a drug delivery platform comprises the combination disclosed herein dispersed within a polymer matrix, typically a biodegradable, bioerodible, and/or bioresorbable polymer matrix. As used herein, the term "polymer" refers to synthetic homo- or copolymers, naturally occurring homo- or copolymers, as well as synthetic modifications or derivatives thereof having a linear, branched or star structure. Copolymers can be arranged in any form, such as, e.g., random, block, segmented, tapered blocks, graft, or triblock. Polymers are generally condensation polymers. Polymers can be further modified to enhance their mechanical or degradation properties by introducing cross-linking agents or changing the hydrophobicity of the side residues. If crosslinked, polymers are usually less than 5% crosslinked, usually less than 1% crosslinked.

Suitable polymers include, without limitation, alginates, aliphatic polyesters, polyalkylene oxalates, polyamides, polyamidoesters, polyanhydrides, polycarbonates, polyesters, polyethylene glycol, polyhydroxyaliphatic carboxylic acids, polyorthoesters, polyoxaesters, polypeptides, polyphosphazenes, polysaccharides, and polyurethanes. The polymer usually comprises at least about 10% (w/w), at least about 20% (w/w), at least about 30% (w/w), at least about 40% (w/w), at least about 50% (w/w), at least about 60% (w/w), at least about 70% (w/w), at least about 80% (w/w), or at least about 90% (w/w) of the drug delivery platform. Examples of biodegradable, bioerodible, and/or bioresorbable polymers and methods useful to make a drug delivery platform are described in, e.g., U.S. Pat. Nos. 4,756,911; 5,378,475; 7,048,946; US2005/0181017; US2005/0244464; US2011/0008437; each of which is incorporated by reference for all it discloses regarding drug delivery.

In aspects of this embodiment, a polymer composing the matrix is a polypeptide such as, e.g., silk fibroin, keratin, or collagen. In other aspects of this embodiment, a polymer composing the matrix is a polysaccharide such as, e.g., cellulose, agarose, elastin, chitosan, chitin, or a glycosaminoglycan like chondroitin sulfate, dermatan sulfate, keratan sulfate, or hyaluronic acid. In yet other aspects of this embodiment, a polymer composing the matrix is a polyester such as, e.g., D-lactic acid, L-lactic acid, racemic lactic acid, glycolic acid, caprolactone, and combinations thereof.

One of ordinary skill in the art appreciates that the selection of a suitable polymer for forming a suitable disclosed drug delivery platform depends on several factors. The more relevant factors in the selection of the appropriate polymer(s), include, without limitation, compatibility of polymer with drug, desired release kinetics of drug, desired biodegradation kinetics of platform at implantation site, desired bioerodible kinetics of platform at implantation site, desired bioresorbable kinetics of platform at implantation site, in vivo mechanical performance of platform, processing temperatures, biocompatibility of platform, and patient tolerance. Other relevant factors that, to some extent, dictate the in vitro and in vivo behavior of the polymer include the chemical composition, spatial distribution of the constituents, the molecular weight of the polymer and the degree of crystallinity.

A drug delivery platform includes both a sustained release drug delivery platform and an extended release drug delivery platform. As used herein, the term "sustained release" refers to the release of a compound disclosed herein over a period of about seven days or more. As used herein, the term "extended release" refers to the release of a compound disclosed herein over a period of time of less than about seven days.

In aspects of this embodiment, a sustained release drug delivery platform releases a compound disclosed herein, or the combination of an ester of an RXR agonist and thyroxine, with substantially first order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release drug delivery platform releases a compound disclosed herein with substantially first order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a drug delivery platform releases a compound disclosed herein with substantially first order release kinetics over a period of, e.g., about 1 day after administration, about 2 days after administration, about 3 days after administration, about 4 days after administration, about 5 days after administration, or about 6 days after administration. In other aspects of this embodiment, a drug delivery platform releases a compound disclosed herein with substantially first order release kinetics over a period of, e.g., at most 1 day after administration, at most 2 days after administration, at most 3 days after administration, at most 4 days after administration, at most 5 days after administration, or at most 6 days after administration.

Administration of a compound, a composition, or a combination disclosed herein include a variety of enteral or parenteral approaches including, without limitation, oral administration in any acceptable form, such as, e.g., tablet, liquid, capsule, powder, or the like; topical administration in any acceptable form, such as, e.g., drops, spray, creams, gels or ointments; buccal, nasal, and/or inhalation administration in any acceptable form; rectal administration in any acceptable form; vaginal administration in any acceptable form; intravascular administration in any acceptable form, such as, e.g., intravenous bolus injection, intravenous infusion, intra-arterial bolus injection, intra-arterial infusion and catheter instillation into the vasculature; peri- and intra-tissue administration in any acceptable form, such as, e.g., intraperitoneal injection, intramuscular injection, subcutaneous injection, subcutaneous infusion, intraocular injection, retinal injection, or sub-retinal injection or epidural injection; intravesicular administration in any acceptable form, such as, e.g., catheter instillation; and by placement device, such as, e.g., an implant, a stent, a patch, a pellet, a catheter, an osmotic pump, a suppository, a bioerodible delivery system, a nonbioerodible delivery system or another implanted extended or slow release system. An exemplary list of biodegradable polymers and methods of use are described in, e.g., *Handbook of Biodegradable Polymers* (Abraham J. Domb et al., eds., Overseas Publishers Association, 1997).

A compound, a composition, or a combination disclosed herein can be administered to a mammal using a variety of routes. Routes of administration suitable for treating a demyelination-related disorder as disclosed herein include both local and systemic administration. Local administration results in significantly more delivery of a compound, a composition, or a combination to a specific location as compared to the entire body of the mammal, whereas, systemic administration results in delivery of a compound, a composition, or a combination to essentially the entire body of the individual. Routes of administration suitable for or treating a demyelination-related disorder as disclosed herein also include both central and peripheral administration. Central administration results in delivery of a compound, a composition, or a combination to essentially the central nervous system of the individual and includes, e.g., nasal administration, intrathecal administration, epidural administration as well as a cranial injection or implant. (Central administration by the nasal route, which targets drug absorption through the vascular plexus of the nasal cavity, is distinct from administration by nasal inhalation which delivers drug through the pulmonary system. Whereas the latter typically uses liquid or dry powder aerosols with mean particle sizes less than 10 microns, and preferably around 2 microns or less, central administration is typically accomplished using mean particle sizes of 10-20 microns or larger. Mists and aerosols can be generated using nebulizers, dry powder inhalers, pressurized aerosols, and atomization pumps, the latter being preferred. Though generally less efficient, it is also feasible to use nose drops for central administration by the nasal route.) Peripheral administration results in delivery of a compound, a composition, or a combination to essentially any area of an individual outside of the central nervous system and encompasses any route of administration other than direct administration to the spine or brain. The actual route of administration of a compound, a composition, or a combination disclosed herein used can be determined by a person of ordinary skill in the art by taking into account factors, including, without limitation, the type of demyelination-related disorder, the location of the demyelination-related disorder, the cause of the demyelination-related disorder, the severity of the demyelination-related disorder, the duration of treatment desired, the degree of relief desired, the duration of relief desired, the particular compound, composition, or combination, the rate of excretion of the compound, composition, or combination used, the pharmacodynamics of the compound, composition, or combination used, the nature of the other compounds to be included in the composition or combination, the particular route of administration, the particular characteristics, history and risk factors of the individual, such as, e.g., age, weight, general health and the like, the response of the individual to the treatment, or any combination thereof. An effective dosage amount of a compound, a composition, or a combination disclosed herein can thus readily be determined by the person of ordinary skill in the art considering all criteria and utilizing his best judgment on the individual's behalf.

In an embodiment, a compound, a composition, or a combination disclosed herein is administered systemically to a mammal. In another embodiment, a compound, a composition, or a combination disclosed herein is administered locally to a mammal. In an aspect of this embodiment, a compound, a composition, or a combination disclosed herein is administered to a site of a demyelination-related disorder of a mammal. In another aspect of this embodiment, a compound, a composition, or a combination disclosed herein is administered to the area of a demyelination-related disorder of a mammal.

In other embodiments, the compound, a composition, or a combination is administered directly to the central nervous system by intrathecal administration, epidural administration, cranial injection or implant, or nasal administration.

In other embodiments, the ester of the RXR agonist is administered orally, buccally, by nasal, and/or inhalation administration, intravascularly, intravenously, by intraperitoneal injection, intramuscularly, subcutaneously, intraocularly injection, by epidural injection; or by intravesicular administration and thyroxine is administered orally. The ester of the RXR agonist and the thyroxine do not need to be administered by the same route or on the same administration schedule.

Aspects of the present specification provide, in part, administering a therapeutically effective amount of an ester of an RXR agonist or a combination of an ester of an RXR agonist and thyroxine. As used herein, the term "therapeutically effective amount" is synonymous with "therapeutically effective dose" and when used in reference to treating a demyelination-related disorder means the minimum dose of a compound, a composition, or a combination necessary to achieve the desired therapeutic effect and includes a dose sufficient to reduce at least one symptom associated with a demyelination-related disorder. In aspects of this embodiment, a therapeutically effective amount of a compound, a composition, or a combination reduces at least one symptom associated with a demyelination-related disorder by, e.g., at least 10%, at least 20%, at least 30%, at least 40%, at least 50%, at least 60%, at least 70%, at least 80%, at least 90% or at least 100%. In other aspects of this embodiment, a therapeutically effective amount of a compound, a composition, or a combination disclosed herein reduces at least one symptom associated with a demyelination-related disorder by, e.g., at most 10%, at most 20%, at most 30%, at most 40%, at most 50%, at most 60%, at most 70%, at most 80%, at most 90% or at most 100%. In yet other aspects of this embodiment, a therapeutically effective amount of a compound, a composition, or a combination disclosed herein reduces at least one symptom associated with a demyelination-related disorder by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%. In still other aspects of this embodiment, a therapeutically effective amount of a compound, a composition, or a combination is the dosage sufficient to reduces at least one symptom associated with a demyelination-related disorder for, e.g., at least one week, at least one month, at least two months, at least three months, at least four months, at least five months, at least six months, at least seven months, at least eight months, at least nine months, at least ten months, at least eleven months, or at least twelve months. When comparing effective doses of an RXR agonist and an ester of the RXR agonist the term "corresponding effective dose" is used to indicate that the same criteria is being used to define effectiveness for both compounds.

IRX4204 shows relevant activity for treatment of nervous system disorders at low concentrations. Transactivation of the Nurr1/RXR heterodimer is apparent at 100 pM, and 1 nM is sufficient to achieve full activation. In vitro measures of therapeutic effects, such as oligodendrocyte differentiation and remyelination, are clearly positive at concentrations as low as 10 pM, with marginal activity detected at 1 pM. To gain other therapeutic effects relevant to treatment of diseases of the nervous system somewhat higher concentrations of 100 pM to 1 nM can be required. For example, a concentration of 1 nM substantially enhances the formation of Treg cells and profoundly inhibits production of IL-17. Thus in various embodiments a therapeutically effective dose is one that produces a concentration in excess of 10 pM, 100 pM, or at least about 1 nM, systemically or in tissues of the nervous system. In some embodiments concentration is measured in the blood. In other embodiments concentration is measured in an affected or target tissue or organ, such as brain tissue or tumor tissue. In still other embodiments it is measured in an organ or tissue of the immune system.

In further embodiments, treatment with the compound, composition, or combination reduces at least one symptom, at least two symptoms, at least three symptoms, at least four symptoms, or at least five symptoms of a demyelination-related disorder.

The amount of active component in a compound, composition, or combination disclosed herein for treating a demyelination-related disorder can be varied so that a suitable dosage is obtained. The actual therapeutically effective amount of a compound, composition, or combination disclosed herein to be administered to a mammal can be determined by a person of ordinary skill in the art by taking into account factors, including, without limitation, the type of the demyelination-related disorder, the location of the demyelination-related disorder, the cause of the demyelination-related disorder, the severity of the demyelination-related disorder, the duration of treatment desired, the degree of relief desired, the duration of relief desired, the particular compound or composition used, the rate of excretion of the compound, composition, or combination used, the pharmacodynamics of the compound, composition, or combination used, the nature of the other compounds to be included in the composition, the particular route of administration, the particular characteristics, history and risk factors of the individual, such as, e.g., age, weight, general health and the like, the response of the individual to the treatment, or any combination thereof. An effective dosage amount of a compound or a composition disclosed herein can thus readily be determined by the person of ordinary skill in the art considering all criteria and utilizing his best judgment on the individual's behalf.

Additionally, where repeated administration of a compound, a composition, or a combination disclosed herein is used, the actual effect amount of compound, composition, or combination disclosed herein will further depend upon factors, including, without limitation, the frequency of administration, the half-life of the compound, composition, or combination disclosed herein. In is known by a person of ordinary skill in the art that an effective amount of a compound or a composition disclosed herein can be extrapolated from in vitro assays and in vivo administration studies using animal models prior to administration to humans. Wide variations in the necessary effective amount are to be expected in view of the differing efficiencies of the various routes of administration. For instance, oral administration generally would be expected to require higher dosage levels than administration by intravenous or intravitreal injection. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors.

As a non-limiting example, when administering an ester of an RXR agonist disclosed herein to a mammal, a therapeutically effective amount generally is in the range of about 0.001 mg/day to about 3000 mg/day. In aspects of this embodiment, an effective amount of a compound or a composition disclosed herein can be, e.g., about 0.01 mg/day to about 0.1 mg/day, about 0.03 mg/day to about 3.0 mg/day, about 0.1 mg/day to about 3.0 mg/day, about 0.3 mg/day to about 3.0 mg/day, about 1 mg/day to about 3 mg/day, about 3 mg/day to about 30 mg/day, about 10 mg/day to about 30 mg/day, about 10 mg/day to about 100 mg/day, about 30 mg/day to about 100 mg/day, about 100 mg/day to about 1000 mg/day, about 100 mg/day to about 300 mg/day, or about 1000 mg/day to about 3000 mg/day. In yet other aspects of this embodiment, a therapeutically effective amount of a compound or a composition disclosed herein can be, e.g., at least 0.001 mg/day, at least 0.01 mg/day, at least 0.1 mg/day, at least 1.0 mg/day, at least 3.0 mg/day, at least 10 mg/day, at least 30 mg/day, at least at least 100 mg/day, at least 300 mg/day, or at least 1000 mg/day. In yet other aspects of this embodiment, a therapeutically effective amount of a compound or a composition disclosed herein can be, e.g., at most 0.001 mg/day, at most 0.01 mg/day, at most 0.1 mg/day, at most 1.0 mg/day, at most 3.0 mg/day, at most 10 mg/day, at most 30 mg/day, at most 100 mg/day, at most 300 mg/day, at most 1000 mg/day, or at most 3000 mg/day. In some embodiments the therapeutic dosage is in the range of about 0.010 to about 1 mg/kg/day, for example about 0.014, 0.043, 0.07, 0.14, 0.21, 0.29, 0.36, 0.43, 0.50, 0.57, 0.64, 0.71, or 1.4 mg/kg/day, or a range bounded by any pair of these values. For a 70 kg subject these exemplary doses correspond to about 1, 3, 5, 10, 15, 20, 25, 30, 35, 40, 45, 50, and 100 mg/day, respectively. Dosage is also sometimes expressed in relation to body surface area, for example in mg/m$^2$/day. Average body surface are for a human adult can range from 1.638 to 2.060, depending on age and sex. Overall averages for cancer patients of 1.73 and 1.79 m$^2$ have been observed. Taking the latter value, doses of 1, 3, 5, 10, 15, 20, 25, 30, 35, 40, 45, 50, and 100 mg/day correspond to about 0.56, 1.68, 2.79, 5.6, 8.4, 11.2, 14.0, 16.8, 19.6, 22.4, 25.1, 27.9, and 55.9 mg/m$^2$/day, respectively. Such interconversions based on other dosages or body sizes are also contemplated. It is generally preferred to scale doses between species based on body surface area rather than on mass, but the latter is used on occasion.

As used herein, the term "thyroid hormone" refers to thyroxine and triiodothyronine. Thyroxine (thyroid hormone $T_4$, levothyroxine sodium) is a tyrosine-based hormone produced by the thyroid gland and is primarily responsible for regulation of metabolism. Thyroxine is a prohormone for triiodothyronine ($T_3$). RXR agonists are known to suppress thyroid function. However supplementation of RXR agonist therapy with thyroid hormones has not been utilized therapeutically.

Suitable thyroxine doses are generally from about 5 μg/day to about 250 μg/day orally initially with an increase in dose every 2-4 weeks as needed. In other embodiments, the suitable thyroxine dose is from about 5 µg/day to about 225 µg/day, from about 7.5 µg/day to about 200 µg/day, from about 10 µg/day to about 175 µg/day, from about 12.5 µg/day to about 150 µg/day, from about 15 µg/day to about 125 µg/day, from about 17.5 µg/day to about 100 µg/day, from about 20 µg/day to about 100 µg/day, from about 22.5 µg/day to about 100 µg/day, from about 25 µg/day to about 100 µg/day, from about 5 µg/day to about 200 µg/day, from about 5 µg/day to about 100 µg/day, from about 7.5 µg/day to about 90 µg/day, from about 10 µg/day to about 80 µg/day, from about 12.5 µg/day to about 60 µg/day, or from about 15 µg/day to about 50 µg/day. Increases in dose are generally made in increments of about 5 µg/day, about 7.5 µg/day, about 10 µg/day, about 12.5 µg/day, about 15 µg/day, about 20 µg/day, or about 25 µg/day.

Dosing can be single dosage or cumulative (serial dosing), and can be readily determined by one skilled in the art. For instance, treatment of a demyelination-related disorder may comprise a one-time administration of an effective dose of a compound, composition, or combination disclosed herein. As a non-limiting example, an effective dose of a compound, composition, or combination disclosed herein can be administered once to a mammal, e.g., as a single injection or deposition at or near the site exhibiting a symptom of a demyelination-related disorder or a single oral administration of the compound, composition, or combination. Alternatively, treatment of a demyelination-related disorder may comprise multiple administrations of an effective dose of a compound, composition, or combination disclosed herein carried out over a range of time periods, such as, e.g., daily, once every few days, weekly, monthly or yearly. As a non-limiting example, a compound, a composition, or a combination disclosed herein can be administered once or twice weekly to a mammal. The timing of administration can vary from mammal to mammal, depending upon such factors as the severity of a mammal's symptoms. For example, an effective dose of a compound, composition, or combination disclosed herein can be administered to a mammal once a month for an indefinite period of time, or until the mammal no longer requires therapy. A person of ordinary skill in the art will recognize that the condition of the mammal can be monitored throughout the course of treatment and that the effective amount of a compound, composition, or combination disclosed herein that is administered can be adjusted accordingly.

A compound, composition, or combination disclosed herein as disclosed herein can also be administered to a mammal in combination with other therapeutic compounds to increase the overall therapeutic effect of the treatment. The use of multiple compounds to treat an indication can increase the beneficial effects while reducing the presence of side effects.

Also disclosed herein for the treatment of nervous system disorders are combinations of esters of RXR agonists and a thyroid hormone co-administered with one or more neurotrophic factors, including but not limited to brain-derived neurotrophic factor (BDNF), glial-derived neurotrophic factor (GDNF), nerve growth factor (NGF), neurotrophin-3 (NT-3), fibroblast growth factor, basic (bFGF), ciliary neurotrophic factor (CNTF), neurotrophic factors-4/5 (NT-4/5), insulin-like growth factor (IGF), insulin; or another neurotrophic factor; or a synthetic mimetic molecule effecting similar biological activities as BDNF, GDNF, NGF, NT-3, bFGF, CNTF, NT-4/5, IGF, insulin or another neurotrophic factor.

Administration of a combination of esters of RXR agonists and thyroid hormone with a neurotrophic factor, or a neurotrophic factor mimetic, may be used to affect neuroprotection, i.e enhanced survival of various types of neural system cells (including neurons and glial cells).

In addition, administration of a combination of esters of RXR agonists and thyroid hormone with a neurotrophic factor, or a neurotrophic factor mimetic, may be used to effect repair of damaged neural system cells (including neurons and glial cells), as manifested by promotion of neurite outgrowth, resulting in formation and/or restoration of neural connections; or formation or restoration of glial structures, such as myelin sheaths around neurons, which are essential for supporting optimal neuronal signal transmission and nervous system functions.

Specific examples of uses of a combination of esters of RXR agonists and thyroid hormone with a neurotrophic factor or neurotrophic factor mimetic include, but are not limited to: co-administration of a combination of a thyroid hormone and an ester of an RXR agonist such as IRX4204EE with GDNF or a GDNF mimetic, to promote dopaminergic neuron survival, or promote repair or restoration of dopaminergic neurons, in patients with Parkinson's disease or other diseases of dopaminergic neurons; co-administration with GDNF or a GDNF mimetic to enhance survival or promote repair or restoration of motor neurons in patients with amyotrophic lateral sclerosis; co-administration with BDNF or a BDNF mimetic, or with insulin or insulin-like growth factor, to enhance survival or promote repair or restoration of cortical or hippocampal neurons in Alzheimer's disease; or co-administration with NGF to enhance survival or promote repair or restoration of sensory neurons in patients with peripheral neuropathies. Other combinations of esters of RXR agonists and thyroid hormone with other neurotrophic factors or neurotrophic factor mimetics, may be used for enhancing survival or promoting repair or restoration of neurons or glial cells for additional diseases of the central or peripheral nervous systems, including but not limited to multiple sclerosis of various forms, including relapsing-remitting or progressive multiple sclerosis; optic neuritis; stroke of various etiologies; nervous system trauma of various types; neuropathies of various etiologies; nervous system hypoxia; toxic insults of the nervous system of various types; dementias of various etiologies; retinopathies of various etiologies; Huntington's disease, various synucleinopathies such as progressive supranuclear palsy; epilepsy; autism; schizophrenia; depression, or aging-related nervous system degeneration.

In the above embodiments, the neurotrophic factor or neurotrophic factor mimetic may be delivered to the patient orally, or by a parenteral route, or by a topical route such as nasally, or as an inhaled medicament; or alternatively by means of an implantable or wearable slow release formulation or slow delivery device.

A combination of esters of RXR agonists and thyroid hormone and a neurotrophic factor, or neurotrophic factor mimetic also may be used for in vitro promotion of survival or growth of neurons or glial cells of various types, for subsequent implantation into the nervous system of a patient with a neurologic disease.

LIST OF PARTICULAR EMBODIMENTS

The following listing of embodiments is illustrative of the variety of embodiments with respect to breadth, combinations and sub-combinations, class of invention, etc., elucidated herein, but is not intended to be an exhaustive enumeration of all embodiments finding support herein. The embodiments listed below relate to IRX4204 (formula (III)), but it should be apparent that there are corresponding embodiments for the genera represented by formulas (I) and (II) and their individual species, as well as formulas (IV) and (V), bexarotene and LG268, respectively.

Embodiment 1

A method of providing IRX4204 to a patient in need thereof, comprising a step of administering a $C_{1-6}$ alkyl ester of IRX4204, wherein an effective dose of the $C_{1-6}$ ester of IRX4204 is lower than a corresponding effective dose of IRX4204.

Embodiment 2

A method of providing IRX4204 to a patient in need thereof, comprising a step of administering a $C_{1-6}$ alkyl ester of IRX4204, wherein an effective dose of the $C_{1-6}$ ester of IRX4204 is greater than a toxicity producing dose of IRX4204.

Embodiment 3

A method of providing IRX4204 to a patient in need thereof, comprising a step of administering a $C_{1-6}$ alkyl ester of IRX4204, wherein a dose-dependent toxicity associated with an effective dose of the $C_{1-6}$ alkyl ester of IRX4204 are reduced as compared to a corresponding effective dose of IRX4204.

Embodiment 4

A method of providing IRX4204 to a patient in need thereof, comprising a step of administering a $C_{1-6}$ alkyl ester of IRX4204, wherein a therapeutic index for administration of the $C_{1-6}$ alkyl ester of IRX4204 is greater than the therapeutic index for administration of IRX4204.

Embodiment 5

A method of providing IRX4204 to a patient in need thereof, comprising a step of administering a $C_{1-6}$ alkyl ester of IRX4204, wherein elevated levels of IRX4204 persist for a longer time interval following administration than following administration of a corresponding dose of IRX4204.

Embodiment 6

A method of providing IRX4204 to a patient in need thereof, comprising a step of administering a $C_{1-6}$ alkyl ester of IRX4204, wherein Cmax of IRX4204 is less than results from administration of a same dose of IRX4204.

Embodiment 7

A method of providing IRX4204 to a patient in need thereof, comprising a step of administering a $C_{1-6}$ alkyl ester of IRX4204, wherein Tmax of IRX4204 is greater than results from administration of a same dose of IRX4204.

Embodiment 8

The method of Embodiment 3, wherein the dose dependent toxicity comprises hypothyroidism.

Embodiment 9

The method of Embodiment 3, wherein the dose dependent toxicity comprises elevation of triglyceride level.

Embodiment 11

The method of Embodiment 3, wherein the dose dependent toxicity is a RAR-associated toxicity.

Embodiment 12

The method of Embodiment 4, wherein the therapeutic index is the therapeutic index with respect to induction of hypothyroidism.

Embodiment 13

The method of Embodiment 4, wherein the therapeutic index is the therapeutic index with respect to induction of elevated triglyceride level.

Embodiment 14

The method of Embodiment 4, wherein the therapeutic index is the therapeutic index with respect to a RAR-associated toxicity.

Embodiment 15

The method of any one of Embodiments 5-7, wherein Cmax is determined in blood, serum, or plasma.

Embodiment 16

The method of Embodiment 15, wherein IRX4204 concentration is determined in blood, serum, or plasma of a human.

Embodiment 17

The method of Embodiment 15, wherein IRX4204 concentration is determined in blood, serum, or plasma of a non-human mammal.

Embodiment 18

The method of any one of Embodiments 5-7, wherein IRX4204 concentration is determined in brain tissue.

Embodiment 19

The method of any one of Embodiments 1-18, wherein corresponding doses of IRX4204 and the $C_{1-6}$ alkyl ester of IRX4204 are compared on a mass basis.

Embodiment 20

The method of any one of Embodiments 1-18, wherein corresponding doses of IRX4204 and the $C_{1-6}$ alkyl ester of IRX4204 are compared on a molar basis.

Embodiment 21

The method of any one of Embodiments 1-20, wherein the $C_{1-6}$ alkyl ester of IRX4204 is an ethyl ester.

Embodiment 22

The method of any one of Embodiments 1-21, wherein an effective dose of the $C_{1-6}$ alkyl ester of IRX4204 is in the range of about 0.001 mg/day to about 3000 mg/day.

Embodiment 23

The method of any one of Embodiments 1-22, wherein administration of the $C_{1-6}$ alkyl ester of IRX4204 produces a systemic concentration IRX4204 of at least 0.1 nM.

Embodiment 24

The method of any one of Embodiments 1-22, wherein administration of the $C_{1-6}$ alkyl ester of IRX4204 produces a systemic concentration of IRX4204 at least 1 nM.

Embodiment 25

The method of any one of Embodiments 1-22, wherein administration of the $C_{1-6}$ alkyl ester of IRX4204 produces a concentration of IRX4204 in a target tissue of at least 0.1 nM.

Embodiment 26

The method of any one of Embodiments 1-22, wherein administration of the $C_{1-6}$ alkyl ester of IRX4204 produces a concentration of IRX4204 in a target tissue of at least 1 nM.

Embodiment 27

The method of Embodiment 25 or 26 wherein the target tissue is a tumor.

Embodiment 28

The method of Embodiment 25 or 26 wherein the target tissue is a central nervous system tissue Embodiment 29 The method of Embodiment 27 wherein the central nervous system tissue is the brain.

Embodiment 30

The method of any one of Embodiments 1-27 wherein administration of the $C_{1-6}$ alkyl ester of IRX4204 produces a systemic concentration of IRX4204 that does not exceed 200 nM.

Embodiment 31

The method of any one of Embodiments 1-27 wherein administration of the $C_{1-6}$ alkyl ester of IRX4204 produces a systemic concentration of IRX4204 that does not exceed 300 nM.

Embodiment 32

The method of Embodiment 31, wherein the ester of IRX4204 is administered orally at a dosage of up to 24, 40, 60, 80, 100, or 120 mg/m$^2$/day.

Embodiment 33

The method of Embodiment 31 or 32, wherein the dosage exceeds 20 mg/m$^2$/day.

Embodiment 34

The method of any one of Embodiments 1-27 or 29-33, wherein the need is a need to treat cancer.

Embodiment 35

A method of treating cancer comprising providing IRX4204 according to the method of any one of Embodiments 1-27 or 29-31.

Embodiment 36

The method of Embodiment 34 or 35, wherein the cancer is acute lymphoblastic leukemia; acute myeloid leukemia, adrenocortical carcinoma; AIDS-related lymphoma; AIDS-related malignancies; anal cancer; bile duct cancer; bladder cancer; bone cancer, brain stem glioma; brain tumor (e.g., astrocytoma, cerebellar astrocytoma; cerebral astrocytoma/malignant glioma; pendymoma brain tumor; supratentorial primitive brain tumor; neuroectodermal tumors; visual pathway and hypothalamic glioma, etc.); breast cancer; bronchial adenomas/carcinoids; carcinoid tumor; carcinoma (adrenocortical; gastrointestinal; islet cell; skin, unknown primary, etc.); cervical cancer; childhood cancers; chronic lymphocytic leukemia; chronic myelogenous leukemia; chronic myeloproliferative disorders; clear cell sarcoma of tendon sheaths; colon cancer; colorectal cancer; cutaneous T-cell lymphoma; endometrial cancer, ependymoma; epithelial cancer; esophageal cancer; Ewing family of tumors; extracranial germ cell tumor; extragonadal germ cell tumor; extrahepatic bile duct cancer; eye cancer, intraocular melanoma; gallbladder cancer; gastric (stomach) cancer; gastrointestinal carcinoid tumor; ovarian germ cell tumor; gestational trophoblastic tumor; hairy cell leukemia; head and neck cancer; hepatocellular (liver) cancer; Hodgkin's lymphoma; hypopharyngeal cancer; islet cell carcinoma (endocrine pancreas); Kaposi's sarcoma; kidney cancer; laryngeal cancer; lip and oral cavity cancer; primary liver cancer; lung cancer, non-small cell lung cancer; small cell lung cancer; primary central nervous system lymphoma; Non-Hodgkin's lymphoma; Waldenstrom's macroglobulinemia; malignant mesothelioma; malignant thymoma; medulloblastoma; melanoma; Merkel cell carcinoma; primary metastatic squamous neck cancer with occult; multiple endocrine neoplasia syndrome; multiple myeloma/plasma cell neoplasm; mycosis fungoides; myelodysplastic syndromes; multiple myeloma; nasal cavity and paranasal sinus cancer; nasopharyngeal cancer; neuroblastoma; oral cancer; oropharyngeal cancer; ovarian epithelial cancer; ovarian low malignant potential tumor; pancreatic cancer; parathyroid cancer; pheochromocytoma penile cancer; pineal and supratentorial primitive neuroectodermal tumors; pituitary tumor; pleuropulmonary blastoma; prostate cancer; rectal cancer; renal cell (kidney) cancer; renal pelvis and ureter, transitional cell cancer; retinoblastoma; rhabdomyosarcoma; salivary gland cancer; sarcoma (e.g., Ewing's family of tumors, Kaposi's; (osteosarcoma)/malignant fibrous histiocytoma of bone, soft tissue, etc.); Sezary syndrome; skin cancer; small intestine cancer; testicular cancer; thymoma; thyroid cancer; trophoblastic tumor; vaginal cancer; vulvar cancer; or Wilms' Tumor. In other embodiments, the method may treat lung cancers, prostate cancer, breast cancer, or pancreatic cancer.

Embodiment 37

The method of any one of Embodiments 1-26 or 28-33 wherein the need is a need to treat a nervous system disorder.

Embodiment 38

A method of treating a nervous system disorder comprising providing IRX4204 according to the any one of Embodiments 1-26 or 28-33.

Embodiment 39

The method of Embodiment 37 or 38, wherein the nervous system disorder is a peripheral nervous system disorder.

Embodiment 40

The method of Embodiment 39, wherein the peripheral nervous system disorder is Guillain-Barré Syndrome, acute inflammatory demyelinating polyneuropathy, chronic inflammatory demyelinating polyneuropathy, demyelinating diabetic neuropathy, progressive inflammatory neuropathy, drug- or toxin-induced neuropathy, such as chemotherapy-induced neuropathy or organophosphate-induced neuropathy, anti-MAG peripheral neuropathy, Charcot-Marie-Tooth Disease, or copper deficiency.

Embodiment 41

The method of Embodiment 37 or 38, wherein the nervous system disorder is a central nervous system disorder.

Embodiment 42

The method of Embodiment 41, wherein the central nervous system disorder is a demyelination-related disorder such as multiple sclerosis, radiation-induced central nervous system inflammation, Alzheimer's disease or Parkinson's disease.

Embodiment 43

The method of Embodiment 4, wherein the central nervous system disorder is relapsing/remitting, primary progressive, and secondary progressive forms of multiple sclerosis (MS), diffuse white matter injury in pre-term infants, neuromyelitis optica, acute disseminated encephalomyelitis, Marburg multiple sclerosis, diffuse myelinoclastic sclerosis (Schilder's disease), Balo concentric sclerosis, solitary sclerosis, optic neuritis, transverse myelitis, amyotrophic lateral sclerosis (ALS), leukodystrophy (multiple variants, e.g. adrenoleukodystrophy, adrenomyeloneuropathy), Parkinson's disease, Alzheimer's disease, progressive supranuclear palsy, stroke, seizure disorders, CNS trauma including traumatic brain injury and traumatic spinal cord injury, radiation induced neuroinflammation, radiation somnolence syndrome, Devic's disease, inflammatory demyelinating diseases, CNS neuropathies, central pontine myelinolysis, Tabes dorsalis (syphilitic myelopathy), progressive multifocal leukoencephalopathy, leukodystrophy, depression, schizophrenia, epilepsy, dementias, and cachexia related to cancer, AIDS, chronic kidney disease, and aging-related nervous system degeneration.

Embodiment 44

A $C_{1-6}$ alkyl ester of IRX4204 for use to provide IRX204 to a patient in need thereof, wherein an effective dose of the $C_{1-6}$ ester of IRX4204 is lower than a corresponding effective dose of IRX4204.

Embodiment 45

A $C_{1-6}$ alkyl ester of IRX4204 for use to provide IRX204 to a patient in need thereof, wherein an effective dose of the $C_{1-6}$ ester of IRX4204 is greater than a maximum tolerated dose of IRX4204.

Embodiment 46

A $C_{1-6}$ alkyl ester of IRX4204 for use to provide IRX204 to a patient in need thereof, wherein a dose-dependent toxicity associated with an effective dose of the $C_{1-6}$ alkyl ester of IRX4204 are reduced as compared to a corresponding effective dose of IRX4204.

Embodiment 47

A $C_{1-6}$ alkyl ester of IRX4204 for use to provide IRX204 to a patient in need thereof, wherein a therapeutic index for administration of the $C_{1-6}$ alkyl ester of IRX4204 is greater than the therapeutic index for administration of IRX4204.

Embodiment 48

A $C_{1-6}$ alkyl ester of IRX4204 for use to provide IRX204 to a patient in need thereof, wherein elevated levels of IRX4204 persist for a longer time interval following administration than following administration of a corresponding dose of IRX4204.

Embodiment 49

A $C_{1-6}$ alkyl ester of IRX4204 for use to provide IRX4204 to provide IRX204 to a patient in need thereof, wherein Cmax of IRX4204 is less than results from administration of a same dose of IRX4204.

Embodiment 50

A $C_{1-6}$ alkyl ester of IRX4204 for use to provide IRX204 to a patient in need thereof, wherein Tmax of IRX4204 is greater than results from administration of a same dose of IRX4204.

Embodiment 51

The $C_{1-6}$ alkyl ester of IRX4204 of any one of Embodiments 30-36, in the treatment of cancer.

Embodiment 52

The $C_{1-6}$ alkyl ester of IRX4204 of any one of Embodiments 30-36, in the treatment of a nervous system disorder.

Embodiment 53

The use of a $C_{1-6}$ alkyl ester of IRX4204 in the manufacture of a medicament to provide IRX4204 to a patient in need thereof for the treatment of cancer or a nervous system disorder, wherein an effective dose of the $C_{1-6}$ ester of IRX4204 is lower than a corresponding effective dose of IRX4204.

Embodiment 54

The use of a $C_{1-6}$ alkyl ester of IRX4204 in the manufacture of a medicament to provide IRX4204 to a patient in need thereof for the treatment of cancer or a nervous system disorder, wherein an effective dose of the $C_{1-6}$ ester of IRX4204 is greater than a maximum tolerated dose of IRX4204.

Embodiment 55

The use of a $C_{1-6}$ alkyl ester of IRX4204 in the manufacture of a medicament to provide IRX4204 to a patient in need thereof for the treatment of cancer or a nervous system disorder, wherein a dose-dependent toxicity associated with an effective dose of the $C_{1-6}$ alkyl ester of IRX4204 are reduced as compared to a corresponding effective dose of IRX4204.

Embodiment 56

The use of a $C_{1-6}$ alkyl ester of IRX4204 in the manufacture of a medicament to provide IRX4204 to a patient in need thereof for the treatment of cancer or a nervous system disorder, wherein a therapeutic index for administration of the $C_{1-6}$ alkyl ester of IRX4204 is greater than the therapeutic index for administration of IRX4204.

Embodiment 57

The use of a $C_{1-6}$ alkyl ester of IRX4204 in the manufacture of a medicament to provide IRX4204 to a patient in need thereof for the treatment of cancer or a nervous system disorder, wherein elevated levels of IRX4204 persist for a longer time interval following administration than following administration of a corresponding dose of IRX4204.

Embodiment 58

The use of a $C_{1-6}$ alkyl ester of IRX4204 in the manufacture of a medicament to provide IRX4204 to a patient in need thereof for the treatment of cancer or a nervous system disorder, wherein Cmax of IRX4204 is less than results from administration of a same dose of IRX4204.

Embodiment 59

The use of a $C_{1-6}$ alkyl ester of IRX4204 in the manufacture of a medicament to provide IRX4204 to a patient in need thereof for the treatment of cancer or a nervous system disorder, wherein Tmax of IRX4204 is greater than results from administration of a same dose of IRX4204.

Embodiment 60

The use of a $C_{1-6}$ alkyl ester of IRX4204 in the manufacture of a medicament to provide IRX4204 to a patient in need thereof for the treatment of cancer or a nervous system disorder, wherein the $C_{1-6}$ alkyl ester of IRX4204 is administered less frequently than a corresponding dose of IRX4204.

Embodiment 61

The use of a $C_{1-6}$ alkyl ester of IRX4204 in the manufacture of a medicament to provide IRX4204 to a patient in need thereof for the treatment of cancer or a nervous system disorder, wherein the medicament comprises an effective amount of the $C_{1-6}$ alkyl ester of IRX4204 that is less than a corresponding effective dose of IRX4204.

Embodiment 62

The use of a $C_{1-6}$ alkyl ester of IRX4204 in the manufacture of a medicament to provide IRX4204 to a patient in need thereof for the treatment of cancer or a nervous system disorder, wherein the medicament comprises more of the $C_{1-6}$ alkyl ester of IRX4204 than the corresponding amount of a maximum tolerated dose of IRX4204.

It should be manifest that each or Embodiments 44-62 can be modified in a manner similar to the modification of Embodiments 1-7 by Embodiments 8-43.

Aspects of the present specification may also be described as follows:

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the methods of treating an autoimmune disorder, in particular a demyelination-related disorder using the RXR agonists or esters of RXR agonists disclosed herein, uses of RXR agonists or esters of RXR agonists disclosed herein to manufacture a medicament and/or treat an autoimmune disorder, in particular a demyelination-related disorder.

Example 1

T Cell Differentiation is Mediated Through RXR Signaling by RXR Agonists

To determine whether a RXR agonist can mediate its effects via RXRα receptor homodimers, RXRβ receptor homodimers, RXRγ receptor homodimers, or any combination thereof, or the corresponding RAR/RXR heterodimers, receptor-mediated transactivation assays were performed. For transactivation assays assessing RXR homodimer signaling, CV-1 cells were transfected with 1) an expression construct including a full length RXRα, RXRβ, or RXRγ; and 2) a rCRBPII/RXRE-tk-Luc reporter construct that included RXR homodimer-specific RXRE/DR1 responsive element linked to a luciferase gene. For transactivation assays assessing RAR/RXR heterodimer signaling, CV-1 cells were transfected with 1) an expression construct comprising a fusion protein including an estrogen receptor (ER) DNA binding domain linked to the ligand binding domain of RARα, RARβ, or RARγ and 2) a ERE-tk-Luc reporter construct that included an estrogen receptor responsive element linked to a luciferase gene. The ER-RAR fusion proteins provided an accurate readout of only the transfected ER-RAR. After transfection, CV-1 cells were treated with RXR agonist IRX4204 at increasing concentrations for 20 hours before measuring luciferase activity. Luciferase activity is expressed as percent of maximal activity obtained using 1 µM RXR agonist IRX4204 for RXRs and 1 µM all-trans-retinoic acid (ATRA) for RARs (Table 1). Data are mean values±SE from five independent experiments.

TABLE 1

RXR Agonist Potencies in Activating RXRs and RARs

| Compound | Structure | EC$_{50}$ (nM) Efficacy (% of 1 µM IRX4204) | | | EC$_{50}$ (nM) Efficacy (% of 1 µM ATRA) | | |
| --- | --- | --- | --- | --- | --- | --- | --- |
| | | RXRα | RXRβ | RXRγ | RARα | RARβ | RARγ |
| IRX4204 | [structure] | 0.08 ± 0.01 100 | 0.47 ± 0.05 100 | 0.09 ± 0.01 100 | >1,000 | >1,000 | >1,000 |

Figure 5A:
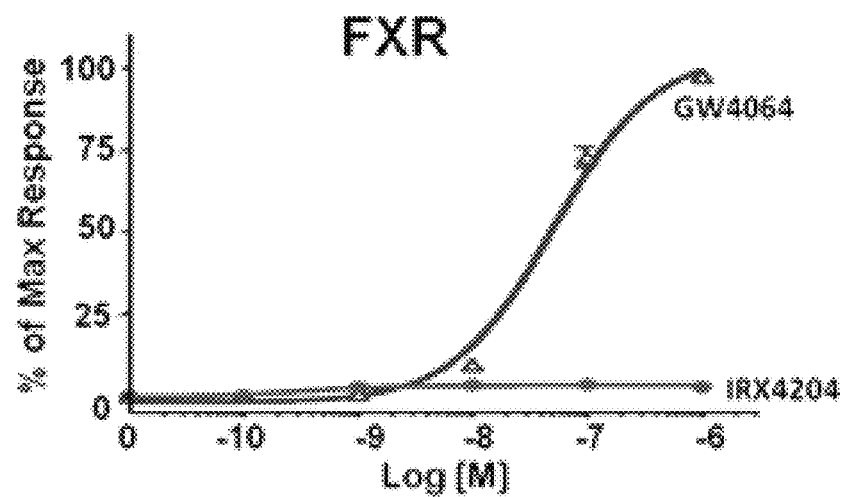
FIG. 5A-D shows that IRX4204 selectively activates RXR-Nurr1 heterodimers. Transactivation assay of IRX4204 (194204, Formula III) for farnesoid X receptor FXR (FIG. 5A); for liver X receptors LXRα and LXRβ (FIG. 5B); for peroxisome proliferator-activated receptor PPARγ (FIG. 5C); and for Nurr1 receptor in the presence or absence of RXR (FIG. 5D).
Figure 5B:
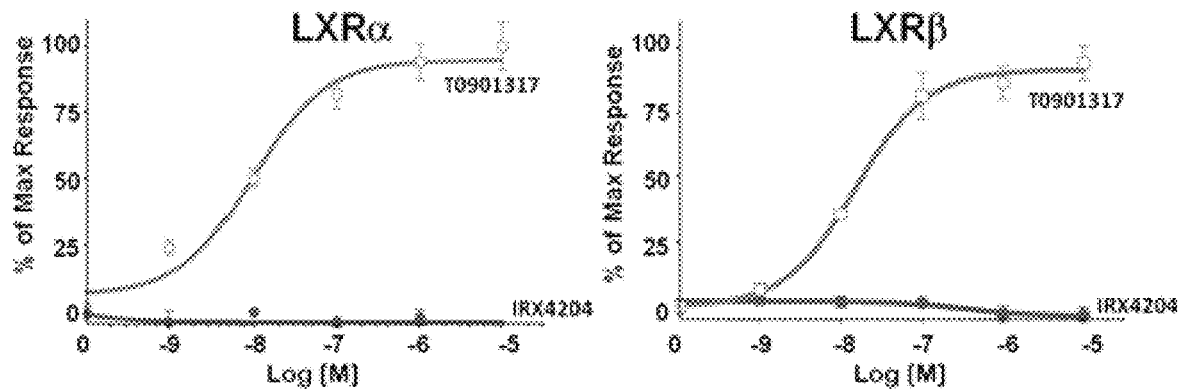
Figure 5C:
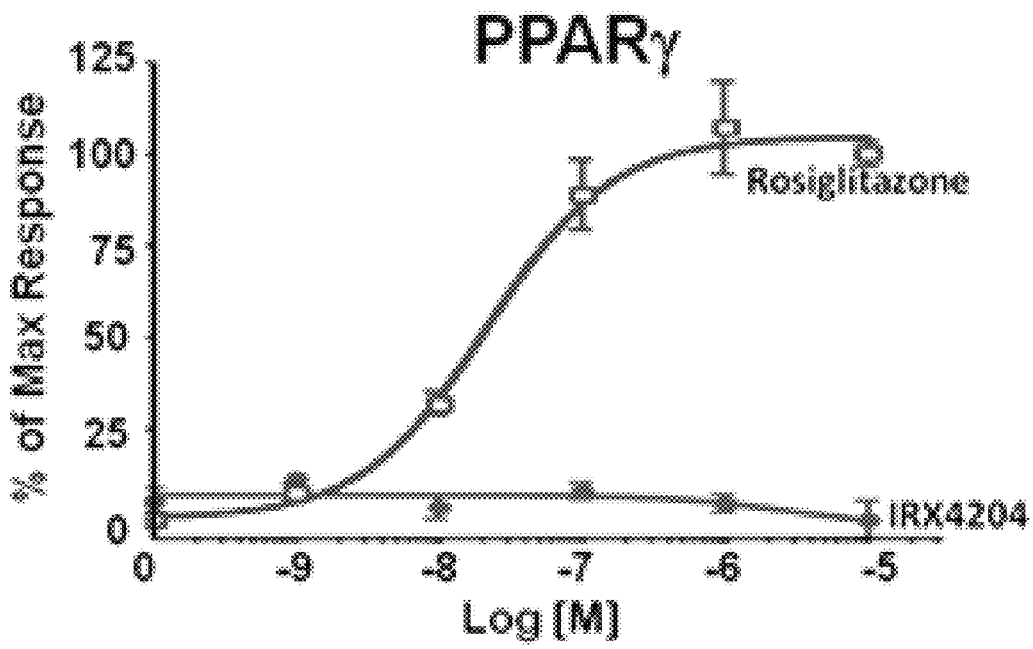
Figure 5D:
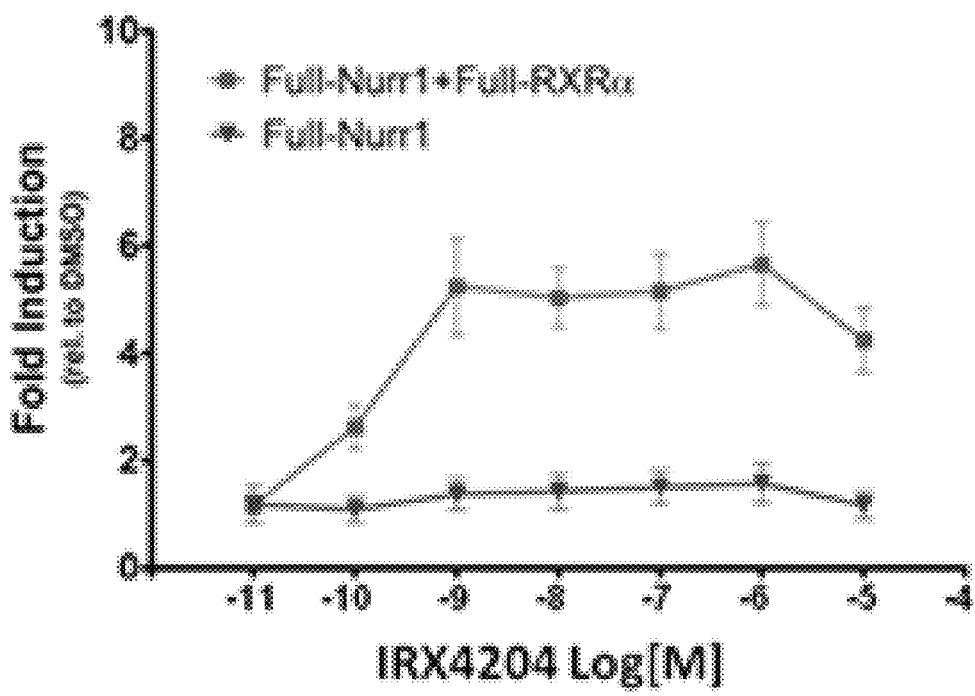

These results indicate that RXR agonist IRX4204 activated RXR receptors with very high potency (EC$_{50}$<0.5 nM) for all three RXR subtypes (Table 1). In contrast, EC$_{50}$ of the RXR agonist for RARs was >1,000 nM with minimal activity detected at ≥1 µM. This difference represents >2,000-fold selectivity for RXRs over RARs in functional transactivation assays. Additionally, these data demonstrate that RXR agonist IRX4204 was more than 1,000-fold more potent in activating RXR receptors rather than RAR receptors. These results indicate that Treg differentiation was mediated through a RXR signaling pathway and not via a RAR signaling pathway. Also, using appropriate receptor and reporter constructs, RXR agonist IRX4204 was shown not to transactivate so called "permissive RXR heterodimers" PPAR/RXR, FXR/RXR and LXR/RXR (FIG. 5A-C). In this regard, RXR agonist IRX4204 is distinct from other RXR agonists. Additionally, IRX4204 selectively activates the Nurr1/RXR permissive heterodimer (FIG. 5D). Thus, RXR agonist IRX4204 has a unique profile in that it selectively activates only RXR homodimers and Nurr1/RXR heterodimers.

A representative example of esters of RXR agonists described herein, namely the ethyl ester of IRX4204 (IRX4204EE), is evaluated in these transactivation assays and is found to be substantially inactive in these assays having EC50 values greater than 1,000 nM. This suggests that esters of RXR agonists, such as IRX4204EE, do not interact with the RXR and RAR receptors, but the activity of these esters in in vivo systems is due to interconversion to the active dissociated acid (conjugate base) forms (for example, IRX4204).

Example 2

Binding Affinity of RXR Agonists

To determine the binding affinity for a RXR agonist, competitive displacement assays were performed. RXRα, RXRβ, RXRγ, RARα, RARβ, or RARγ were expressed in SF21 cells using a baculovirus expression system and the resulting proteins were purified. To determine the binding affinity for a RXR agonist for an RXR, purified RXRα, RXRβ, and RXRγ were separately incubated with 10 nM [$^3$H]-9CRA, and the binding affinity of the RXR agonist IRX4204 was determined by competitive displacement of [$^3$H]-9CRA from the receptor. To determine the binding affinity for a RXR agonist for an RAR, purified RARα, RARβ, and RARγ were incubated with 5 nM [$^3$H]-ATRA, and the binding affinity of the RXR agonist IRX4204 was determined by competitive displacement of [$^3$H]-ATRA from the receptor. Ki values are mean values of at least two independent experiments (Table 2). Standard errors (±) among independent experiments are indicated.

As shown in Table 2, RXR agonist IRX4204 displayed high affinity for RXRα, RXRβ, and RXRγ with Ki values being 1.7, 16, and 43 nM, respectively. In contrast, the RXR agonist IRX4204 bound with very low affinity to each of the RARs (Ki values being >1,000 nM). These data indicate that IRX4204 is highly selective for the RXRs relative to the RARs.

Also, the esters of RXR agonists (such as IRX4204EE) are tested in these binding assays and found to be substantially inactive (Ki values >1,000 nM) indicating that these esters are pro-drugs that do not interact directly with the receptors

TABLE 2

| | | RXR Binding Affinity Ki (nM) | | | RAR Binding Affinity Ki (nM) | | |
|---|---|---|---|---|---|---|---|
| Compound | Structure | RXRα | RXRβ | RXRγ | RARα | RARβ | RARγ |
| IRX4204 | [chemical structure] | 1.7 ± 0.1 | 16 ± 1.0 | 43 ± 3.0 | 6344 ± 674 | 7552 ± 638 | 4742 ± 405 |

Example 3

RXR Agonists and Esters of RXR Agonists Attenuate EAE in B6 Mice

To determine whether a RXR agonist can attenuate multiple sclerosis, C57BL/6 (B6) mice were immunized (day 0) to induce experimental autoimmune encephalomyelitis (EAE) by subcutaneous (s.c.) injection at the base of their spine with 200 μL of adjuvant containing 125 μg myelin oligodendrocyte glycoprotein peptide (35-55) (MOG peptide; Peptides International, Louisville, Ky.) and 400 μg non-viable M. tuberculosis H37 desiccate emulsified in a mixture of incomplete Freund's adjuvant and phosphate buffered saline (PBS). Mice were also given 200 ng of pertussis toxin in PBS administered by inter-peritoneal (i.p.) injection on the same day as MOG emulsion injection (day 0) and 2 days later (day 2). Starting on day 7 after immunization, mice were given the RXR agonist IRX4204 (50 μg), or the ester of IRX4204 (IRX4204EE; 50 μg) or vehicle control i.p. every other day for the duration of the experiment (n=6-7 mice/group). Statistics show the results of a Mann Whitney test (analyzed from start of treatment to the end of the experiment). Mice were scored using the following scale: 0—Mice have no disease, 1—Mice have distal limp tail or rear leg weakness (paresis), 1.5—Mice have distal limp tail and rear leg weakness, 2—Mice have complete limp tail and rear leg weakness, 2.5—Mice have complete limp tail and weakness in both rear legs, 3—Mice have complete limp tail and paralysis in both rear legs, 3.5—Mice have complete limp tail, paralysis in both rear legs, and forelimb weakness. Mice receiving a score of 3.5 were immediately euthanized.

Figure 2:
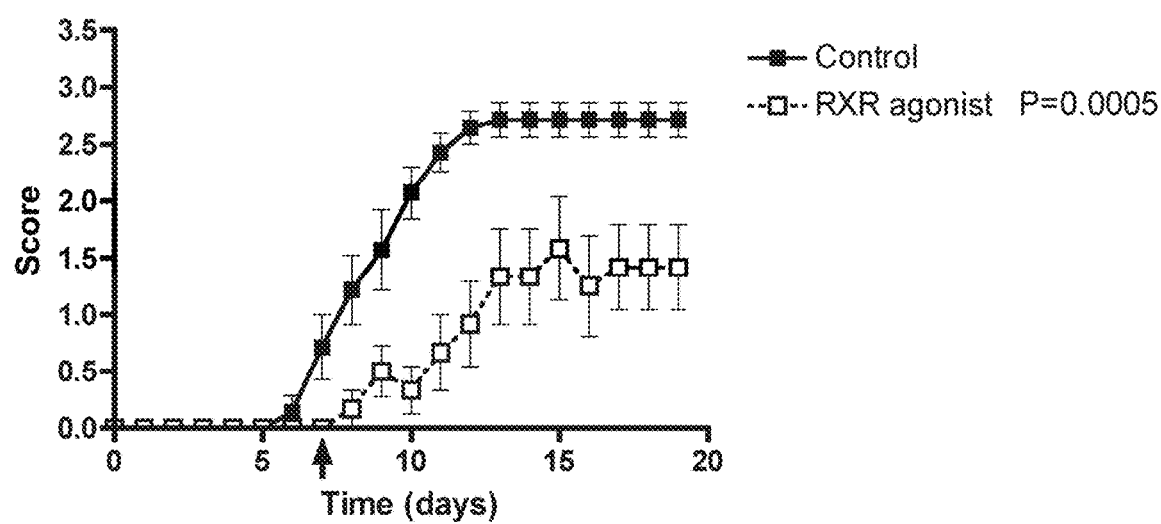
FIG. 2 shows that RXR agonists attenuate experimental autoimmune encephalomyelitis (EAE) in C57BL/6 mice.

FIG. 2 depicts scores of disease severity over time. The results indicate that administration of the RXR agonist IRX4204 at 50 μg significantly reduces the symptoms of EAE in mice. Efficacy of the RXR agonist was observed after the first administration (day 7) and maintained throughout the course of the study (day 20). Surprisingly, the ester pro-drug, IRX4204EE, is more effective than IRX4204 in reducing the symptoms of EAE A dose titration experiment was also conducted in EAE mice. EAE was induced in 28 B6 mice with MOG/CFA and PT as above. Mice were scored on day 7 as indicated above and divided into groups by score so means are as equal as possible. Starting day 8, mice were scored and injected with a vehicle control or IRX4204 (50 μg, 100 μg, or 200 μg) every day.

Figure 7:
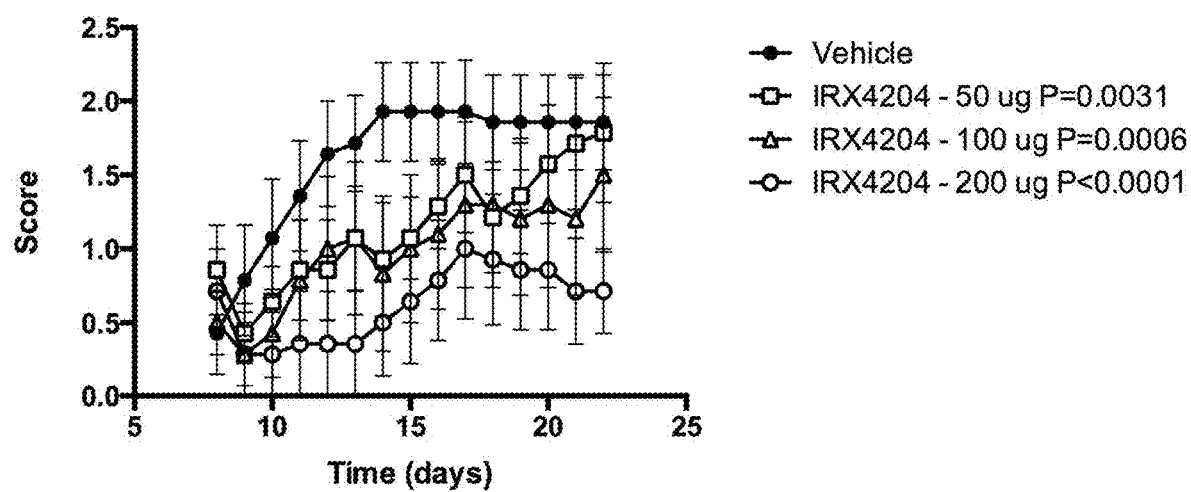
FIG. 7 depicts effects of RXR agonist IRX4204 on EAE in mice.

The mice were weighed at the beginning of experiment and every day they had a score of 2.5 or higher and mice were euthanized if they lost 15% or more of their start weight. All mice were treated with IRX4204 had significantly less disease overall (FIG. 7). A similar dose titration experiment is carried out with IRX4204EE and the ester, IRX4204EE, is more active than IRX4204 at each of the doses tested. At the completion of the experiment, the vehicle control and 200 μg/day groups were euthanized and spleen and CNS samples obtained.

Figure 8A:
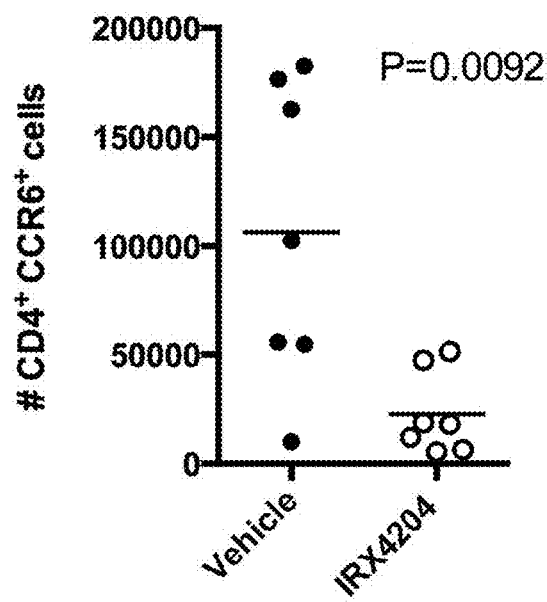
FIG. 8A-B depicts expression of CCR6 (FIG. 8A) and CD49d (FIG. 8B) on splenocytes from EAE mice treated with 200 µg/day of IRX4204 or control.
Figure 8B:
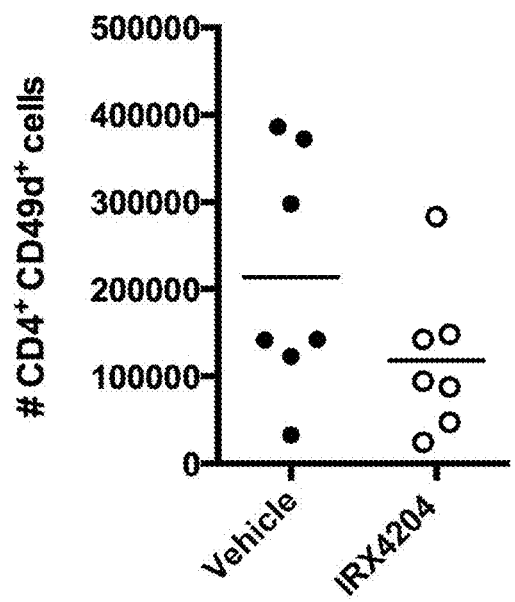

The spleen samples were evaluated for CD49d (FIG. 8A) and CCR6 (FIG. 8B), and IRX4204 treatment lowered CCR6, but not CD49d, expression on CD4 T cells. Additionally, CD4+CD25hi cells (generally consisting of TReg) were reduced, although the frequency was not altered (FIGS. 9A and 9B). The total number of effector and memory CD4 T cells, as indicated by CD44 expression, decreased with IRX4204 treatment (FIG. 12C) and the total number of recently activated CD4 T cells, as indicated by expression of both CD69 and CD44, was also decreased with IRX4204 treatment (FIG. 9D).

Figure 10:
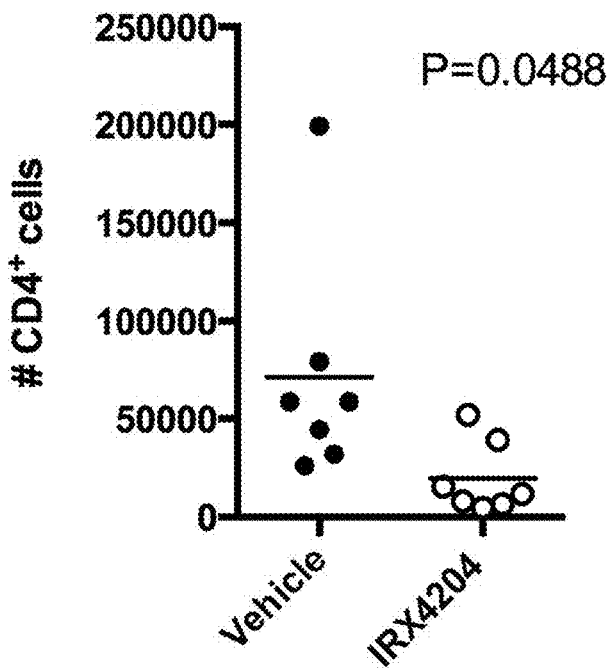
FIG. 10 depicts the total number of infiltrating CD4 T cells in the CNS of EAE mice treated with 200 µg/day of IRX4204 or control.
Figure 11A:
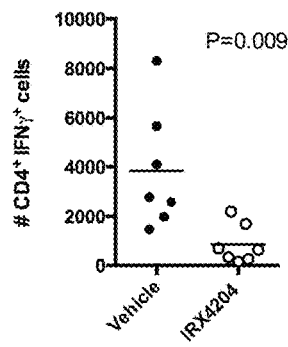
FIG. 11A-D depicts restimulation of the infiltrating lymphocytes of FIG. 10 to determine expression of interferon gamma (IFNγ) (FIG. 11A), IL-17A (FIG. 11B), tumor necrosis factor (TNF) (FIG. 11C), and IL-4 (FIG. 11D).
Figure 11B:
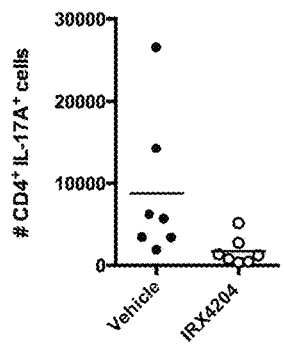
Figure 11C:
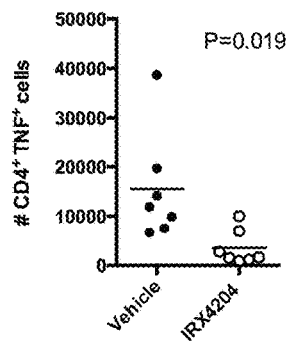
Figure 11D:
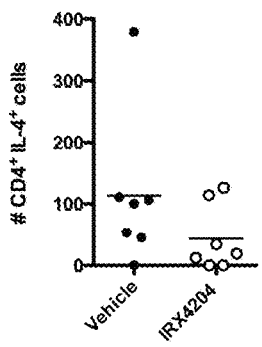
Figure 12A:
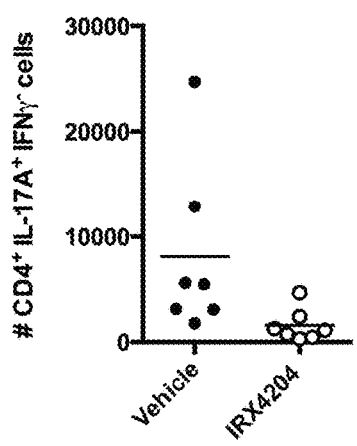
FIG. 12A-C depicts the quantification of co-expression of IFNγ and IL-17A by CD4 T cells of FIG. 10 expressing IL-17A and not IFNγ (FIG. 12A), IL-17A and IFNγ (FIG. 12B), IFNγ and not IL-17A (FIG. 12C).
Figure 12B:
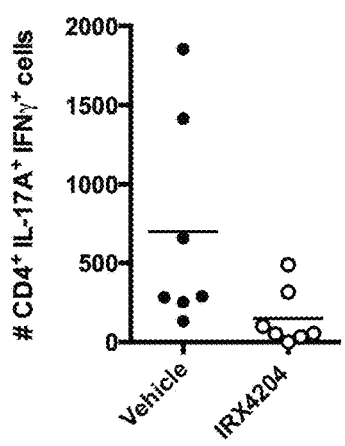
Figure 12C:
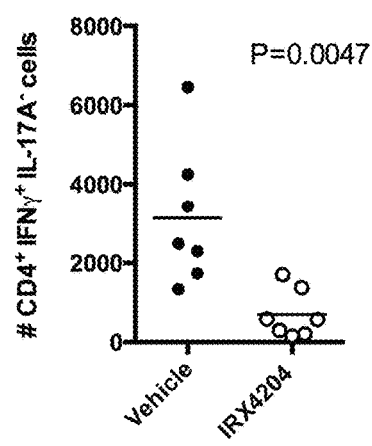

In the CNS, the total the total number of infiltrating CD4 T cells was reduced with IRX4204 treatment (FIG. 10). Restimulation with PMA/Ionomycin was used to help detect the cytokine production. Both IFNγ (FIGS. 11A and 11B) and TNF (FIGS. 11C and 11D) were significantly reduced with treatment. Co-expression of IFNg and IL-17A by CD4 T cells in CNS was quantified, but was not significantly different between groups (FIG. 12A-12C).

Example 4

RXR Agonist-Treated Mice have Reduced Central Nervous System Infiltrating Cells To determine whether a RXR agonist can reduce central nervous system (CNS) infiltrating cells, C57BL/6 (B6) mice were treated as described in Example 6. On day 20 after immunization, mice were sacrificed and perfused with phosphate buffered saline (PBS). Brain and spinal cord tissue was isolated, digested with DNase and LIBERASE DL® (Roche Diagnostics, Indianapolis, Ind.) for 30 minutes, and homogenized through 70 micron nylon mesh filters. Resulting cells were placed over a Percoll gradient to remove myelin. The remaining cells (microglia and CNS infiltrating cells) were counted, stained for molecules of interest, and run on a flow cytometer. Based on the frequencies obtained by FACS of these cell populations, total cell numbers of CNS infiltrating leukocytes expressing CD45, including $CD4^+$ T cells and $CD11c^+$ $CD11b^+$ myeloid dendritic cells (DC), were calculated.

Figure 3A:
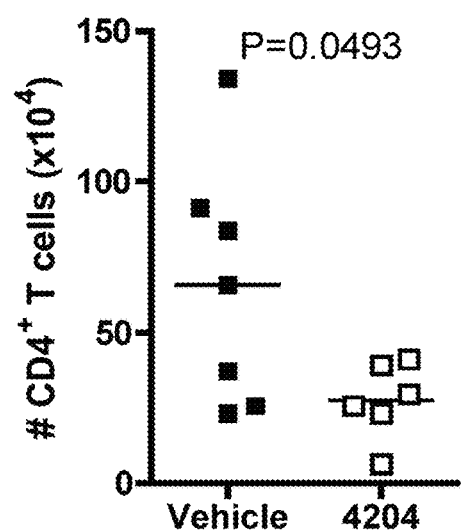
FIG. 3A-B shows that RXR agonists reduce leukocyte infiltration into the central nervous system.
Figure 3B:
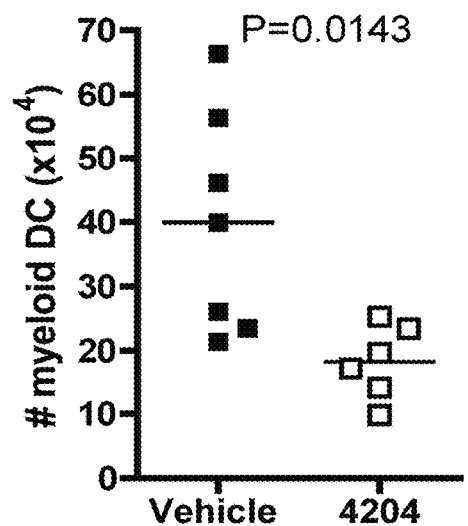

FIG. 3 depicts the number of $CD4^+$ cells (FIG. 3A) or $CD11c^+$ $CD11b^+$ cells (myeloid DC; FIG. 3B) in mice treated with the RXR agonist IRX4204 versus the vehicle control. There was a significant reduction in the infiltration of both $CD4^+$ cells and $CD11c^+$ $CD11b^+$ cells in animals treated with a RXR agonist as compared to the control. A similar experiment is carried out with IRX4204EE and there is an even greater reduction in these infiltrating cells than there is with IRX4204. As disease is propagated in the CNS through the $CD4^+$ cells infiltrating the CNS and becoming re-activated by $CD11c^+$ $CD11b^+$ cells, this suggests that part of the mechanism of action in this model is to limit the presence of the cells in the CNS.

Example 5

RXR Agonists Attenuate EAE in SJL Mice

To determine whether a RXR agonist or an ester of a RXR agonist can attenuate multiple sclerosis, SJL mice were immunized to induce EAE by s.c. injection at the base of their spine with 200 µL of adjuvant containing 200 µg proteolipid proteins (139-151) (PLP peptide; Peptides International, Louisville, Ky.) and 400 µg of non-viable *M. tuberculosis* H37 desiccate emulsified in a mixture of incomplete Freund's adjuvant and PBS. Mice were also given 150 ng of pertussis toxin in PBS i.p. on the same day as PLP emulsion injection and 2 days later. Starting day 7 after immunization, mice were given the RXR agonist IRX4204 (50 µg), or the same amount of ester pro-drug (IRX4204EE) or vehicle control i.p. every other day for the duration of the experiment (n=6 mice/group). Mice were scored using the scale described in Example 6.

Figure 4:
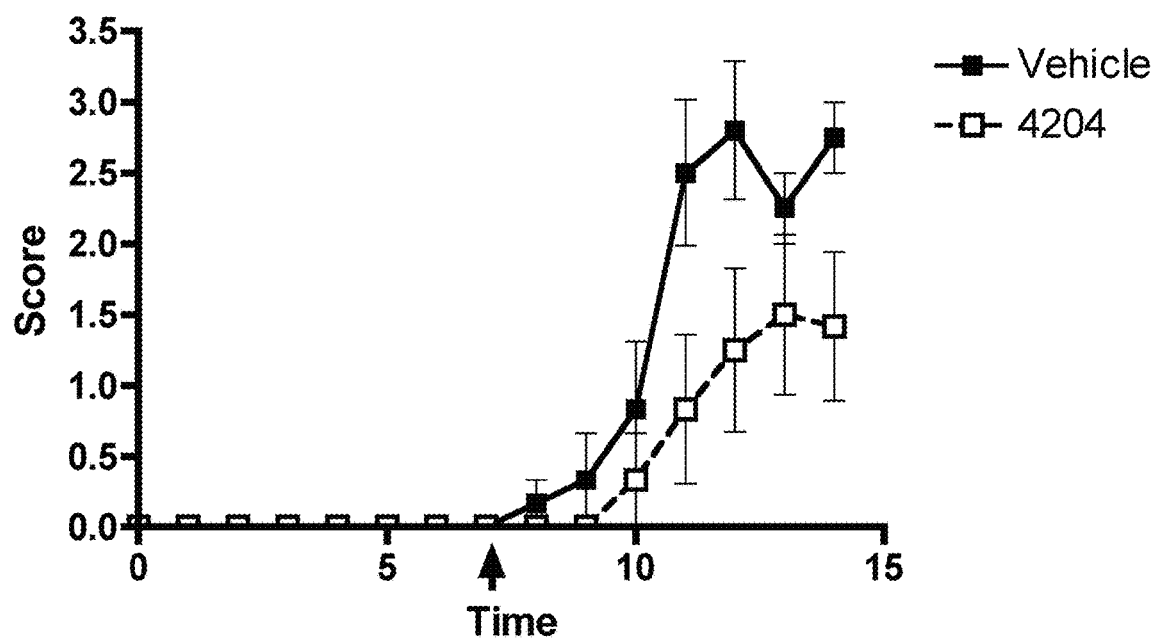
FIG. 4 shows RXR agonists attenuate EAE in SJL mice.

The results indicate that administration of the RXR agonist IRX4204 significantly reduces the symptoms of EAE in mice. Table 3 shows the features of a RXR agonist IRX4204 treatment in SLJ mice. FIG. 4 depicts scores of disease severity over time. Efficacy of the RXR agonist was observed after the second administration (day 8) and maintained throughout the course of the study (day 14). A similar experiment is performed with the ester, IRX4204EE, and greater efficacy than IRX4204 is observed with the ester in EAE induced in SJL mice.

TABLE 3

RXR agonist Treatment in SJL Mice

| Clinical Features | Vehicle | IRX4204 |
|---|---|---|
| Mean Maximum Score | 3.2 ± 0.6 | 1.5 ± 1.4 |
| Disease Incidence | 6/6 | 4/6 |
| Death from Disease | 4/6 | 0/6 |

Example 6

RXR Agonist IRX4204 as a Selective Activator of Nurr1/RXR Permissive Heterodimer In order to determine which permissive RXR heterodimer is activated by the RXR agonist IRX4204, receptor transactivation assays were carried out as follows for PPARγ/RXR, FXR/RXR, LXRα/RXR, LXRβ/RXR, and Nurr1/RXR. For PPARγ: CV-1 cells were transfected with 3×(rAOX/DR1)-tk-Luc reporter gene and an expression vector for PPARγ. For FXR:CV-1 cells were transfected with 3×(IBABP/IRI)-tk-Luc reporter gene and vectors for FXR and RXRα. For LXR:CV-1 cells were transfected with 3×(PLTP/LXRE)-tk-Luc reporter gene with vectors for LXRα or LXR3. For Nurr1: COS7 cells were transfected with 3×NBRE-tk-luc reporter gene and full length Nurr-1 with or without full-length RXRα plasmid. Cells were then treated with vehicle or IRX4204 for 20 hr. Luciferase data were normalized to co-transfected 3-gal activity. Luciferase activity was expressed as percent of maximal activity obtained using specific agonists. Rosiglitazone (PPARγ), GW4064 (FXR), T0901317 (LXR). The data indicate that IRX4204 does not activate FXR/RXR (FIG. 5A), LXRα/RXR or LXRβ/RXR (FIG. 5B), or PPARγ/RXR (FIG. 5C). In contrast, IRX4204 potently ($EC_{50}$<1 nm) activates the Nurr1/RXR heterodimer. These data collectively indicate that IRX4204 is a unique RXR agonist in that it selectively activates the Nurr1/RXR heterodimer but not the PPARγ/RXR, FXR/RXR or LXR/RXR heterodimers. The ethyl ester pro-drug, IRX4204EE, is tested in the same receptor transactivation assays and is found to have very little activity again suggesting that it needs to be converted to IRX4294 for it to have activity.

Example 7

Effect of RXR Agonists on Oligodendrocyte Precursor Cell Differentiation

Figure 6:
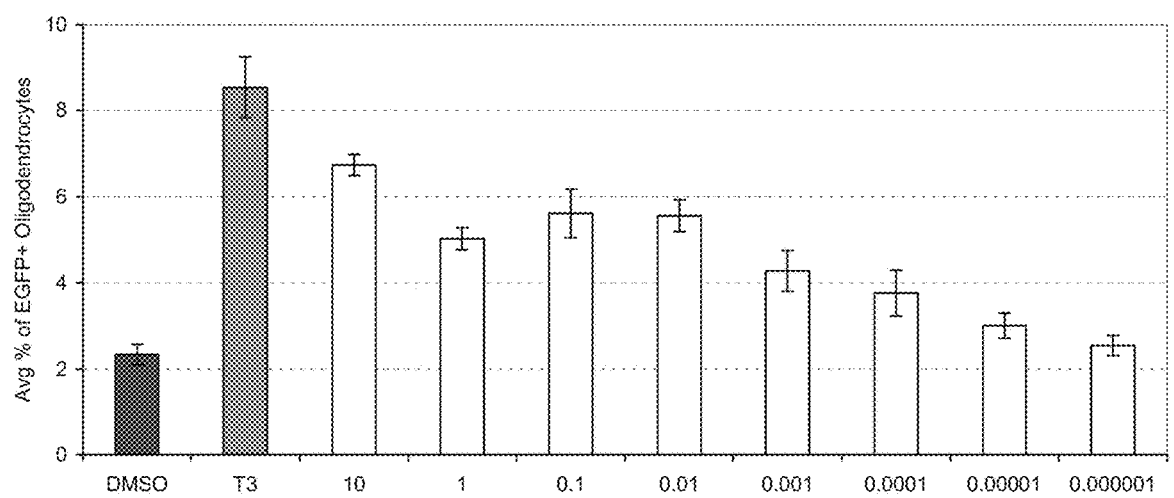
FIG. 6 shows the percentage of green fluorescent protein (EGFP) positive oligodendrocytes after culture of oligodendrocyte precursor cells derived from embryonic mouse brains with various concentrations of IRX4204.

The goal of this study was to evaluate the effect of IRX4204 on differentiation of oligodendrocyte precursor cells (OPCs) into oligodendrocytes. OPCs were generated from a neurosphere culture of E14.5 PLP-EGFP (on C57BL/6J background) mouse brains. The isolated OPCs were treated with IRX4204 to evaluate the expression of green fluorescent protein (EGFP), which correlates with differentiation of OPCs into oligodendrocytes. The EGFP expressing cells were quantified with Cellomics Neuronal Profiling Algorithm. The positive (T3) control demonstrated differentiation of OPCs as expected. The results demonstrate that IRX4204 promotes OPC differentiation into oligodendrocytes as shown by the increase in the number of the EGFP positive cells compared to negative control (DMSO). All tested concentrations but the lowest concentration ($1^{-6}$ µM) showed a significant increase in OPC differentiation into oligodendrocytes (FIG. 6, data for IRX4204 are shown as open bars with concentrations expressed in µM).

The EGFP expressing cells in controls and all compounds were quantified with Cellomics Neuronal Profiling Algorithm. The experiment was successful as demonstrated by the significant increase in % EGFP cells in positive control (T3; 8.5%) compared to the negative control (DMSO; 2.3%). IRX4204 promotes OPC differentiation into oligodendrocytes as demonstrated by the dose dependent increase in the number of the EGFP positive cells compared to negative control (DMSO). IRX4204 did not show any differences in total cell number and pyknotic cells compared to controls. The results from this study demonstrate that IRX4204 promotes OPC differentiation. The data show a dose-dependent increase in the percentage of EGFP cells compared to the negative control. These date indicate that IRX4204 promotes the growth of myelin-forming cells in cell culture. The ester, IRX4204EE, is tested in the oligodendrocyte precursor cell differentiation assay and has essentially no activity, again suggesting that it needs to be converted in vivo to the IRX4204 active species for the ester to show activity.

Example 8

IRX4204 Enhances Central Nervous System (CNS) Remyelination in an In Vivo Model by Acting Directly on the Remyelination Process A focal toxin (ethidium bromide) induced rat model of demyelination is used to ascertain the direct effects of IRX4204 on acute demyelination independent of the immunomodulatory effects of IRX4204. The experiment uses rats of relatively advanced age (1 year) since such rats undergo remyelination in a less efficient manner, thereby providing data that are more relevant to the clinical treatment of human patients with multiple sclerosis or other demyelination disorders.

Focal demyelination is induced in one year old rats (approximately 300 g in weight) by injecting stereotactically 5 μl of ethidium bromide solution (0.01% vol/vol in saline) in a bilateral manner into the caudal cerebellar peduncles (CCP). Starting seven days after injection of the ethidium bromide, the rats are treated by oral gavage with 10 mg/kg/day of IRX4204 (in DMSO and corn oil) or vehicle (DMSO and corn oil) for fourteen days (day 7 to day 21 post-ethidium bromide treatment). The rats are killed on day 24 post-ethidium bromide treatment for analysis of remyelination by quantitative polymerase chain reaction (qPCR) and microscopy.

Analysis of the lesions reveal the following: the densities of Olig2$^+$ oligodendrocyte lineage cells and CC1+ differentiated oligodendrocytes increased in IRX4204-treated animals relative to vehicle treated animals; Nkx2.2+oligodendrocyte precursor cells (OPCs) increased in IRX4204-treated lesions relative to vehicle treated lesions. Also, real-time qPCR analysis of lesion samples show an increase in Mbp expression and an increase in Pdgfra expression indicating higher levels of myelin regeneration in IRX4204-treated animals. Ultrastructural analyses of CCP lesions further demonstrate that IRX4204 treatment results in more remyelinated axons in animals than vehicle treatment. AG-ratio analysis (this ratio is that of axon diameter to myelinated axon) also shows that IRX4204-reated animals have a lower G-ratio than vehicle treated animals and that this lower ratio is due to the formation of thicker remyelinated sheaths surrounding axons in IRX4204-treated animals. All these findings are consistent with an increase in CNS remyelination in IRX4204-treated animals.

The ester, IRX4204EE is similarly tested in the focal toxin induced rat model of demyelination and tested for the same end-points. Surprisingly, the ester, IRX4204EE, is somewhat more active than the free acid, IRX4204 suggesting that IRX4204EE reaches target organs and tissues at higher concentrations than IRX4204 and then converted efficiently into IRX4204.

Example 9

IRX4204 Ethyl Ester (IRX4204EE) Exhibits a Longer Presence but Lower Cmax than IRX4204 in Both Blood and Brain Esters are expected to become hydrolyzed in the aqueous environment of the body thereby generating the same active species as the free acid (that is, the anionic form of the dissociated acid; the conjugate base), although the speed of absorption and conversion will typically be slower. To assess whether this was the case for IRX4204EE the concentration in blood and brain of IRX4204 and IRX4204EE following intravenous injection was determined in mice.

A group of male ICR mice (N=9) weighing approximately 20-24 g each were each injected intravenously in the tail vein with either IRX4204 or IRX4204EE. The compounds were dissolved in 4% DMSO, 1% Tween80 and 95% PBS (v/v) at a concentration of 0.2 mg/ml. Each mouse was injected with a volume to deliver 1 mg/kg of the compound (corresponding to 3 mg/m$^2$).

At designated time points (0.5, 1.5, and 3 hr), with the mice under terminal isofluorane anesthesia, systemic blood sample (ca 0.4-0.5 mL) were collected by cardiac puncture into micro-tube containing sodium EDTA-K$_2$ as anti-coagulant (n=3 at each time point). Blood samples from the IRX4204EE arm of the study had appropriate esterase inhibitors added. The blood was centrifuged at 13000 rpm for 3 min at 4° C. to obtain plasma and protein was precipitated with acetonitrile prior to being assayed for compound content. The brain was removed and transferred to a pre-weighed vessel for weight determination. Brain tissue was homogenized in five volumes of PBS, centrifuged, and the supernatant assayed for compound content. A specific and sensitive LC-MS/MS assay was developed to quantitate both IRX4204 and IRX4204EE. The same standard curve was used to quantitate analyte concentrations in both brain and plasma.

Figure 13A:
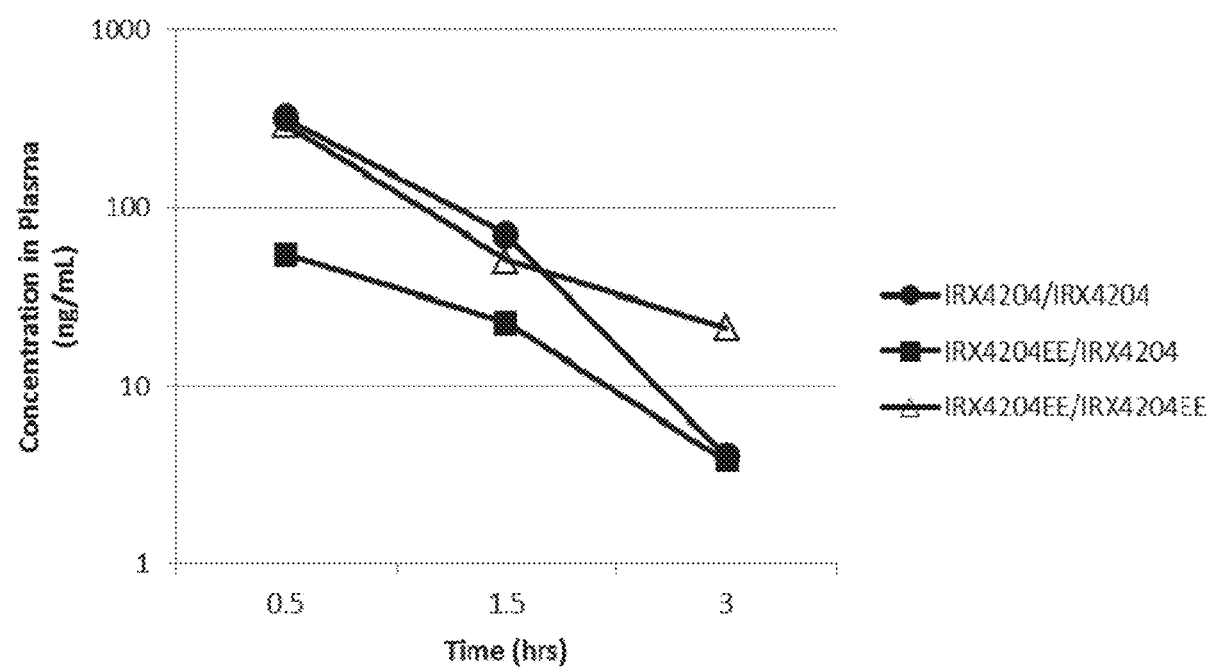

Initially (at the half-hour time point) both IRX4204 and IRX4204EE were present at similar concentrations in the blood; the concentration of IRX4204 due to conversion of IRX4204EE was only about one sixth that due to the IV injection of IRX4204. As IRX4204 concentration was already falling at this point, and falling more rapidly for the IRX4204 administration, the systemic IRX4204 Cmax achieved through use of IRX4204EE is reduced to a greater extent than by a factor of one sixth. At three hours the concentration of IRX4204 in the blood resulting from administration of the free acid and ester forms was about the same, while the concentration of the ester itself was about 5-fold greater (see FIG. 13A). The remaining substantial concentration of the ester and slower decay of the concentration of ester-derived IRX4204 suggests that at longer times the concentration of IRX4204 from direct administration with fall below that derived from the ester.

In the brain, initially a much higher concentration of IRX4204 was seen from direct administration than from conversion of the ester; almost 8-fold higher. The concentration of the unconverted ester was similar to that of the ester-derived active form at this time point. The concentration of the ester in the brain rose slightly over the course of this experiment. In contrast the concentration of IRX4204, whether from direct administration or conversion of the ester, fell over this time interval, the former faster than the latter. At the 3 hour time point the concentration of the ester in blood and brain was approximately the same (see FIG. 13 B). The concentration of IRX4204 in brain tissue 3 hours post-administration corresponds to approximately 7.9-8.2 nM. By many in vitro measures of effectiveness IRX4204 is effective at concentrations variously between 0.1 and 1 nM, and concentrations as low as 10 μM support remyelination. Whereas administration of IRX4204 provides a single source of the compound to the brain, the concentration of IRX4204 following administration of IRX4204EE reflects the absorption of IRX4204 from the blood stream following conversion from the ester, as well as conversion of IRX4204EE in the brain itself following absorption of the ester. The still substantial concentrations of IRX4204EE in both the blood stream and in brain tissue at 3 hours post administration lead to the expectation that going forward the decline in concentration of IRX4204 in the brain resulting from administration of IRX4204EE will continue to be slower than from administration of IRX4204 itself. Thus administration of IRX4204EE will lead to therapeutic levels of IRX4204 for a prolonged period of time as compared to administration of IRX4204 itself.

The flatter IRX4204 pharmacokinetic curve obtained from administration of the ethyl ester leads to several conclusions:

- it should be possible to administer the ester at higher dosages than IRX4204 itself while avoiding or minimizing dose-dependent toxicities that would occur if IRX4204 were administered at those higher dosages.
- administration of the ester will provide therapeutically effective concentrations of IRX4204 in the body for a longer period of time than administration of IRX4204 itself for any particular dosage.
- on any periodic dosage schedule IRX4204EE will provide therapeutically effective concentrations for a greater period of the interval between doses or maintain a greater margin above a therapeutic threshold concentration.
- on a dosage schedule designed to maintain drug concentration above some threshold value it will be possible to administer the ester prodrug less frequently and/or at a lower dose.
- the ester will have a higher maximum tolerated dose.
- the ester will have a better therapeutic index. That is, the distinction between a effective dose and a toxic dose will be greater, or more precisely that the ratio of a toxic dose to an effective dose will be greater.

The ester will have a broader therapeutic window.

Example 10

IRX4204 and IRX4204 Ethyl Ester (IRX4204EE) Accelerate Remyelination in a Mouse Model of Demyelinationx The cuprizone (bis-cyclohexanone oxaldihydrazone) model facilitates reliable, reproducible and unequivocal analysis of myelin parameters in both white and grey matter. The cuprizone model is a model for toxic demyelination. In this model, young mice are fed with the copper chelator cuprizone, leading to oligodendrocyte death and a subsequent reversible demyelination. The cuprizone-fed mice are also dosed with rapamycin, a drug that blocks mTOR and spontaneous remyelination, allowing better quantification of oligodendrocyte turnover. In the acute cuprizone paradigm, male C57BL/6 mice at 6 to 9 weeks of age are fed a diet of chow mixed with 0.2% cuprizone over the course of 6 weeks. By the third week of cuprizone feeding, consistent demyelination can be observed in the corpus callosum, the largest white matter tract in the mouse brain. Demyelination reaches a maximum at 5 or 6 weeks. Chronic demyelination can be induced if C57BL/6 mice are maintained on a diet with cuprizone for 12 weeks.

In this study, the chronic (12-week) model will be used to assess remyelination potential of IRX4204 and IRX4204EE. Mice are fed a cuprizone-containing diet and injected with rapamycin daily (CR regimen) for 12 weeks to induce demyelination. One group of animals is sacrificed at 12 weeks to evaluate demyelination. The remaining mice are discontinued from the cuprizone/rapamycin regimen, and treatment with IRX4204, IRX4204EE, or vehicle control with each treatment being done with and without thyroxine (T4) is initiated for a three week treatment period. At the end of the study, all mice are sacrificed and one or more of the following parameters are determined: (1) PPD (p-phenylenediamine) staining to visualize and quantify myelinated axons in corpus callosum to assess demyelination and remyelination in white matter; (2) myelin proteolipid protein (PLP) immunostaining to visualize and quantify myelin in hippocampus to assess demyelination and remyelination in grey matter (hippocampus); (3) PLP immunostaining to visualize and quantify myelin in cortex to assess demyelination and remyelination in grey matter (cortex); (4) PDGFRα immunostaining to visualize and quantify OPCs in corpus callosum; (5) GSTpi immunostaining to visualize and quantify oligodendrocytes in corpus callosum; (6) Iba1 (ionized calcium-binding adapter molecule 1) and/or Mac-2 (galectin-3) immunostaining to visualize and quantify total and activated microglia in corpus callosum; (7) GFAP (glial fibrillary acidic protein) immunostaining to visualize and quantify astrocytes in corpus callosum To assess astroglial activation; and (8) 3D-electron microscopy in corpus callosum to assess ratio of myelinated and non-myelinated axons, internodal length, G-ratio, mitochondrial changes, etc.

The goal of this study is to evaluate the remyelination potential of IRX4204EE with or without thyroid hormone supplementation in a mouse model of toxic demyelination. Previous studies have demonstrated efficacy of IRX4204 in an EAE model of MS. Also, previous data demonstrates that IRX4204 can induce significant oligodendrocyte precursor cell (OPC) differentiation in vitro. The current study is conducted to further investigate the CNS effects of IRX4204EE in the cuprizone model of MS and determine the effects of combination with thyroxine on remyelination and neuroprotection. IRX4204EE does not interact directly with the RXRs and rather is metabolized in vivo into IRX4204.

The animals (8 week-old male C57BL/6J mice) are subjected to cuprizone diet plus rapamycin injections (CR) for 12 weeks to induce demyelination in white matter (CC, corpus callosum). After 12 weeks, CR is discontinued and subsets of animals are treated daily for 6 weeks with one of the following treatment regimens:

TABLE 4

| Group # | Treatment |
|---|---|
| 1 | Oral IRX4204/IRX4204EE vehicle |
| 2 | SC thyroxine vehicle |
| 3 | IRX4204 (10 mg/kg/d PO) + SC thyroxine vehicle |
| 4 | IRX4204 (10 mg/kg/d PO) + 20 ng/g thyroxine SC |
| 5 | IRX4204EE (10 mg/kg/d PO) + SC thyroxine vehicle |
| 6 | IRX4204EE (10 mg/kg/d PO) + 20 ng/g thyroxine SC |
| 7 | No treatment (sacrificed) after 12 wks of CR |

All animals are sacrificed after 12 weeks of CR (Group 7) or after further 6 weeks of treatment (Groups 1-6) to evaluate myelin in white matter (corpus callosum) and gray matter (hippocampus and cortex). In addition, the size of myelinated axons are quantified and the large myelinated axons are further assessed by 3D-electron microscopy (3D-EM).

The results from this study demonstrate that IRX4204EE significantly increases the size of myelinated axons in the corpus callosum. In addition, these large myelinated fibers demonstrate a healthy phenotype. Thus, the combination of IRX4204EE and thyroxine has a neuroprotective effect on myelinated neurons. IRX4204 has a substantial neuroprotective effect only in combination with thyroxine and the overall remyelination induced by IRX4204 is less than that induced by IRX4204EE. The results from this study are surprising since the ester IRX4204EE does not interact directly with the RXRs and hence does not function as a rexinoid directly. It functions as a rexinoid only by acting as a pro-drug and being converted to the active parent free acid form (IRX4204). Thus, the ester is expected to be significantly less active than the free acid IRX4204.

Induction of Demyelination by CR Regimen

A total of 92 mice are included in the study. Eight week-old male C57BL/6J mice are placed on a rodent chow (Harlan) containing 0.3% cuprizone for 12 weeks. These mice are also injected with rapamycin (approximately 10 mg/kg body weight at the volume of 0.1 ml, IP) daily for 12 weeks. Eight mice are maintained on a normal diet. The weight of the animals is monitored on a weekly-basis.

Drug Treatment

Following 12 weeks of CR, one group of mice (n=12, Group 3) will receive treatment with oral IRX4204 and subcutaneously thyroxine vehicle for 6 weeks. The drug is reconstituted in vehicle (DMSO/PBS/Tween) and fresh drug is made up once a week and administered orally once daily. Another group of CR-treated mice (n=12, Group 4) receive treatment with oral IRX4204 once daily and subcutaneous thyroxine injections once daily. Similarly, subgroups (n=12) of CR treated mice are treated with oral IRX4204EE and subcutaneous thyroxine vehicle (Group 5) or oral IRX4204EE and subcutaneous thyroxine (Group 6) at the indicated doses. Control CR treated mice receive daily oral IRX4204 vehicle (n=12; Group 1) or daily subcutaneous thyroxine vehicle n=12, Group 2).

Transcardial Perfusion and Extraction of Brain

To harvest tissue for histological analysis, mice are perfused with buffered 4% PFA (paraformaldehyde). All mice are anaesthetized with 100 μl ketamine/xylazine mix (50 μl into each side of the abdomen, beneath ribs). A lack of response to a toe pinch is used to ensure sufficient depth of anesthesia. The thoracic cavity is opened surgically and diaphragm is cleared from ribs, and a flap including sternum is cut and pinned back. Pericardium is cleared from the heart and a needle (with fixative and pump attached) is inserted into the left ventricle of the heart, the right atrium is cut, and 4% PFA is pumped through the circulatory system. The animals are checked for stiffness during and after perfusion. Brains are then removed from the cranial cavity.

Brain Slicing

Brains are placed (dorsal side down) on a custom made brain slicing mold. Two single-edge knives are placed at an angle on groove #4 and #5. One edge of the knife is held with one finger and the knives are slowly pushed down on the brain using the other hand. The slice is then transferred to a glass vial containing 2.5% glutaraldehyde/4% PFA fixative in Sorenson's buffer and post-fixed overnight. To dissect out the corpus callosum (CC), the slice is placed in a petri dish containing Sorenson's buffer and two cuts are made along the edge of the corpus callosum. The curvature of the cortex serves as a landmark for the orientation. A third cut is made along the midline of the CC. The two halves of the CC are then stored in glu/PFA for 3-5 days before embedding in Epon for further analysis.

The remaining rostral and caudal brain parts are placed in buffered PFA for 2-3 days at 4° C. and transferred to cryoprotection solution at 4° C. until completely infiltrated. Cryoprotected brain tissues are retained for future studies.

Epon Embedding

Vials are labeled and the labels are covered with tape. Specimens are washed for 3×10 minutes in 0.08M Sorenson's buffer. Tissues are placed in 2% osmium tetroxide ($OsO_4$) in Sorenson's buffer for 2 hours at room temperature. The tissues are washed 2× in 0.08 M Sorenson's buffer and dehydrated through graded alcohol at room temperature in a fume hood on a rotator:

70% EtOH for 2-times @ 10 min each
80% EtOH for 2-times @ 10 min each
95% EtOH for 2-times @ 10 min each
100% EtOH for 3-times @ 15 min each (fresh 100% EtOH)

The tissues are then washed twice with polypropylene oxide (10 min each wash) and then placed in 1:1 polypropylene oxide/Epon mix and rotated overnight an uncapped tube in the hood. The tissues are placed in fresh Epon for 1 hour on the rotator and then embedded in fresh Epon in a mold with labels and baked at 60° C. for 24 to 48 hrs.

Epon Sections (1-μm) and Paraphenylenediamine (PPD) Staining

Epon blocks are trimmed with a razor blade to expose the tissue region of interest. Blocks are faced by cutting a number of 1-2 micron sections until the block-face is smooth and all mechanical damage is removed. Six additional 1-μm thick sections are cut and placed on a slide, which is baked on a hot plate until the tissues are dry. A drop of filtered toluidine blue stain is added and tissues stained for ~30 sec, or as necessary to develop sufficient staining. Toluidine blue is washed in running water and the slide dried, and mounted with CYTOSEAL™ (Thermo Scientific) using a thin (No. 1) coverslip. Excess CYTOSEAL™ is squeezed onto an absorbent paper and the slide is examined with dry microscope lenses (10× and 20×) to check for section suitability, integrity and orientation. If the sections are acceptable, additional sections are cut for at least 10 slides and dried by baking on a hot plate. Two slides are stained with PPD and the remaining slides are stored at room temperature for future analysis.

The PPD stain is filtered before use and the procedure is performed in a Coplin jar. The slides are stained for 15 minutes and rinsed 3 times in absolute ethanol. The slides are then rinsed 3 times in xylene, air-dried and coverslipped for analysis.

Microscopic Evaluation of PPD and PLP Stained Sections

Epon-PPD stained sections of corpus callosum are evaluated in bright field at 10×, 20× and 63× (oil objective). A total of 4 images (63×) per animal are collected in the region of interest (ROI), which is a specific region between the rostral corpus callosum and the junction of the fornix. The images outside the ROI are not scored. The images are then evaluated using NIH ImageJ (aka. Fiji) to identify and count myelinated axons in the region of interest. The numbers of PPD-stained myelinated axons in all of the counting boxes for each image are counted. Using the polygon selection tool, the margins of the corpus callosum in each slice are identified and ImageJ is then used to calculate the total area of the CC in that slice. The total number of myelinated axons in a specific area of the corpus callosum is then calculated by dividing the total area of the CC by the total area of the counting boxes and multiplying by the combined number of myelinated axons that are counted in all of the counting boxes for each image. The average number of myelinated axons per this anatomically defined region of the corpus callosum from each of the 4 images of each animal in each treatment group is then used for statistical calculations. The size of individual myelinated axons is measured by using NIH ImageJ.

Whole sections stained with anti-PLP are scanned in a Mirax slide scanner with a 20× lens (NA 0.8). The images are then exported at 10× for further processing using NIH ImageJ software. Specific regions of interest in cortex and hippocampus are analyzed using ImageJ software, where the area occupied by PLP staining is calculated.

Three Dimensional Electron Microscopy (3D-EM)

Plastic embedded corpus callosum samples from a subset of animals in various groups are stained with heavy metals and examined by 3D-EM (serial blockface scanning EM) to visualize myelin and axonal ultrastructural changes. Following identification of the region of interest (ROI), one tissue block is selected per animal for further analysis by 3D-EM. Zeiss Sigma VP scanning electron microscope with Gatan 3View in-chamber ultramicrotome is used to evaluate all the tissue blocks containing ROI. The system is run using standard settings that provide optimal spatial resolution to assess axonal mitochondrial populations in several axons (typically 2.0 kV/10 nm/pixel and 40 nm slices). Axon lengths of approximately 30 micrometer are traced and reconstructed using Reconstruct software to evaluate various axonal and mitochondrial parameters.

Statistical Analysis

GraphPad Prism is used to conduct all statistical analyses. All data are tested for normal distribution by Kolmogorov-Smirnov or Shapiro-Wilk tests. The normally distributed data are subjected to Student's t-test or one-way ANOVA followed by post hoc testing by Dunnett's or Tukey multiple comparison tests. The data that does not pass normality or equal variance test are compared by using Mann-Whitney Rank Sum test.

Results

A total of 92 animals are included in the study, where all 92 animals receive CR demyelination for 12 weeks. After demyelination, a subset (n=10, Group 7) of animals are sacrificed to serve as controls to assess baseline demyelination. The remaining animals are divided into groups (n=12) which are treated daily with oral IRX4204 (10 mg/kg)+SC administered vehicle for thyroxine (Group 3), oral IRX4204 (10 mg/kg)+SC thyroxine (20 ng/g, Group 4), oral IRX4204EE+SC thyroxine vehicle (Group 5), oral IRX4204EE and SC thyroxine (Group 6), oral vehicle for IRX4204/IRX4204EE alone (Group 1), or SC thyroxine vehicle alone (Group 2).

There is no mortality or any obvious health concerns during the treatment phase.

ANOVO analysis of terminal body weights with multiple group comparison show no significant difference in any of the groups.

Floating brain sections are immunostained with PLP to visualize and quantify myelin in gray matter, hippocampus and cortex. The percentage area covered by PLP staining in animals treated with vehicles only after discontinuation of the demyelination regimen is significantly greater than in animals who were sacrificed immediately after CR demyelination demonstrating the occurrence of spontaneous remyelination.

The anticipated average percentage areas covered by PLP staining (myelin) are listed in Table 5. There is no significant difference in the extent of gray matter remyelination in IRX4204+thyroxine vehicle treated animals after 6 weeks of treatment in either hippocampus or cortex when compared to vehicles only control. However, the percentage areas of PLP staining in gray matter (hippocampus and cortex) is significantly higher in animals treated with IRX4204+thyroxine supplement compared to animals treated with IRX4204 and thyroxine vehicle or animals treated with vehicles only. The results obtained in the IRX4204EE groups are very surprising since the ester is expected to be significantly less active than the free acid. The percentage area of hippocampal myelin in the IRX4204EE group (Group 5) is 68% compared to 38% in the IRX4204 group (Group 3). With thyroxine supplementation, the hippocampal area of myelination is 84% for IRX4204EE (Group 6) compared to 54% for the IRX4204 group (Group 4). Similar results are obtained with the cortex; IRX4204EE without thyroxine (Group 5) gives 85% cortical myelination, while the IRX4204 group (Group 4) cortical myelination area (48%) is not different from the vehicles only groups (Group 1 and 2). Cortical myelination in the IRX4204EE plus thyroxine group (Group 6) is as high as 95%.

TABLE 5

| Group # | % Area of Myelin | |
| --- | --- | --- |
| | Hippocampus | Cortex |
| 1 | 38 | 46 |
| 2 | 37 | 47 |
| 3 | 38 | 48 |
| 4 | 54 | 70 |
| 5 | 68 | 85 |
| 6 | 84 | 95 |
| 7 | 3 | 24 |

The anticipated number of myelinated axons in the corpus callosum are shown in Table 6. The number and density of PPD stained myelinated axons in the corpus callosum are significantly higher in the IRX4204+thyroxine treated animals compared to animals treated with vehicles only or with IRX4204+thyroxine vehicle or animals sacrificed after demyelination. Surprisingly again, groups treated with IRX4204EE (Groups 5 and 6) give significantly higher numbers of myelinated axons in the corpus callosum than found in the IRX4204 groups (Groups 3 and 4). The number of myelinated axons in the group treated with IRX4204 and thyroxine vehicle (Group 3) is 1570 while this number is increased to 4300 in the group treated with IRX4204EE and thyroxine vehicle (Group 5). In the thyroxine supplemented groups, the relevant number for IRX4204 treatment (Group 4) is 2200 while it is 5100 for the IRX4204EE treatment.

TABLE 6

| Group # | # of Myelinated Axons per CC unit |
| --- | --- |
| 1 | 1530 |
| 2 | 1532 |
| 3 | 1570 |
| 4 | 2200 |
| 5 | 4300 |
| 6 | 5100 |
| 7 | 135 |

Further analysis of the myelinated axons demonstrate that the average diameter is significantly larger in the animals treated with IRX4204+thyroxine vehicle (Group 3, approximately 0.9 µm) or with IRX4204+thyroxine (Group 4, approximately 1.1 µm) compared to the diameter in the animals treated with only the vehicles (Groups 1 and 2, approximately 0.83 µm). Three dimensional election microscopy (3D-EM) confirms this increased axonal diameter in the IRX4204 treated groups. Furthermore, 3D-EM examination of mitochondrial metrics (volume, length, and diameter) and morphological integrity show the larger diameter myelinated axons in the IRX4204-treated animals have normal mitochondria with well-formed cristi. Cyctoskeletal assessments also demonstrate good cytoskeletal integrity of the larger caliber myelinated axons. These findings indicate that IRX4204 treatment of demyelinated CR mice with, or without, thyroxine supplementation, produces a population of larger, healthy myelinated axons.

IRX4204 produces the same number of myelinated axons as the vehicles only control but the axons are larger in diameter. An assessment of myelin volume demonstrates an approximately 15% increase in myelin volume in the IRX4204 treated animals compared to control. The IRX4204+thyroxine treated animals produce an approximately 30% increase in myelin volume compared to the vehicles control.

The trend of the greater activity of IRX4204EE compared to the free acid is maintained in the assays for axonal diameter and 3D-EM evaluations. IRX4204EE treatment, with or without thyroxine, results in both increased amounts of myelinated axons as well as increased axonal diameter. Examination by 3D-EM of mitochondrial metrics and morphological integrity show that the larger diameter myelinated axons produced by IRX4204EE treatment are healthy. Myelin volume is increased by approximately 25% by IRX4204EE treatment and, in addition, the number of myelinated axons are increased. The IRX4204EE plus thyroxine treated animals produce an approximately 40% increase in myelin volume compared to the vehicle controls.

IRX4204 demonstrates in vitro a significant increase in OPC differentiation to oligodendrocytes, the cells that make new myelin. The goal of this study is to evaluate remyelination and neuroprotective potential of IRX4204 and its ethyl ester (IRX4204EE) in a mouse model of toxic demyelination. Mice are subjected to CR regimen for 12 weeks followed by treatment with IRX4204 or IRX4204EE, with or without thyroxine, or vehicle control for 6 weeks.

IRX4204 alone does not promote a significant increase in the number and density of myelinated axons in either white or gray matter following toxic demyelination. However, a significant increase in the size of the myelinated axons after treatment with IRX4204 is observed. Furthermore, the increase in the size is more pronounced in the largest caliber axons. This increase in larger caliber axons is demonstrated to represent a population of larger, healthy myelinated axons by ultrastructural assessment of mitochondria and cytoskeletal integrity. These findings suggest that IR4204 has a direct impact on the axons thereby affording neuroprotection.

Combination treatment with IRX4204 and thyroxine in the CR mouse model of toxic demyelination results in significant increases in the number and density of myelinated axons in white and gray matter. Furthermore, an even greater increase in healthy, myelinated larger caliber axons is observed with the combination. These findings suggest that treatment with IRX4204 with concurrent administration of thyroxine to approximate a euthyroid condition will be optimally effective in CNS diseases by promoting remyelination and neuroprotection.

Surprisingly, groups treated with IRX4204EE show across the board greater remyelination and neuroprotection activity than the corresponding IRX4204 treated groups. This increased activity cannot be ascribed to the intrinsic rexinoid activity of IRX4204EE since it is a pro-drug which needs to be converted to its conjugate base form (IRX4204) to show rexinoid activity. In other words, IRX4204 is a more active rexinoid than IRX4204EE. The superior activity of IRX4204EE in the CR model of toxic demyelination and hence in treating human MS is an unexpected finding.

Example 11

Combination of IRX4204EE and Thyroid Hormone as Preventing Demyelination in Mouse Model of Toxic Demyelination In a variation of Example 9, mice are treated with a combination of IRX4204EE and thyroxine at the same levels as in Example 9, during the demyelination phase to determine if the combination can protect neurons from demyelination. It is predicted that treatment with the combination results in a significantly higher number of remyelinated axons compared to the vehicle control.

Example 12

A Human Clinical Trial to Ascertain Effects of the Combination of IRX4204EE and Thyroxine on Myelin Repair in Multiple Sclerosis Patients with Relapsing-Remitting Disease A proof of concept clinical trial of the combination of IRX4204EE and thyroxine is conducted in multiple sclerosis (MS) patients to ascertain the direct effects of IRX4204EE on myelin repair in patients with relapsing-remitting MS. Patients with relapsing-remitting MS are recruited to participate in the clinical trial and are provided informed consent describing risks and potential benefits of participation. The MS patients are treated with one of several dose levels of IRX4204EE, ranging from 1 mg/day to 40 mg/day, administered orally as capsules, once per day and thyroxine, administered at 12.5 µg/day to 250 µg/day orally. Some patients are randomized to receive a placebo dose using matching capsules, which do not contain IRX4204EE or thyroxine. Patients are dosed for a minimum of 30 days, and as long as 180 days. Patients are assessed for the status of myelin damage and speed of repair of demyelination in MS lesions that occur over this period of time in their brains, spinal cords, and/or optic nerves. Quantitation of myelin damage and repair is performed at baseline and periodically through the dosing, using specialized imaging methods, which specifically examine and quantitate myelin damage and repair in these parts of the nervous system. Such methods include, but are not limited to, Positron Emission Tomography (PET) scanning, utilizing imaging agents such as the thioflavine-T derivative 2-(4'-methylaminophenyl)-6-hydroxybenzothiazole (PIB), which also binds to amyloid plaques. This compound is useful for useful for quantitating myelin repair. Alternatively, magnetic resonance imaging (MRI) using special contrast agents that bind to or enhance the appearance of areas of myelin damage or repair is utilized; or special MRI analytical algorithms, such as magnetization transfer imaging, or diffusion tensor imaging, are utilized to quantitate myelin damage and repair in the IRX4204EE and thyroxine-treated patients compared to the placebo-treated patients. Dose response relationships of the IRX4204EE/thyroxine combination to myelin protection or repair are analyzed across the cohorts of patients treated with various dose levels of IRX4204EE and thyroxine. In addition to the quantitation of myelin damage and repair by imaging methods, the clinical status of the MS patients' disease progression is preliminarily evaluated using standard clinical endpoints for MS clinical trials, such as the Expanded Disability Status Scale (EDSS). The EDSS is a 10 point scale which quantitates the MS patients' levels of disability by evaluating physical activities of daily life, such as walking, swallowing, bowel and bladder function, etc. In addition, visual acuity testing is performed to quantitate effects of the IRX4204EE/thyroxine combination on myelin damage and repair in the optic nerves.

Example 13

A Human Clinical Trial to Evaluate the Effects of a Combination of IRX4204EE and Thyroxine Treatment on Progression of Disability in Multiple Sclerosis Patients with Relapsing-Remitting Disease A clinical trial to provide definitive evidence of benefit of IRX4204EE/thyroxine treatment on progression of disability in MS is conducted in MS patients with relapsing-remitting MS. Patients with relapsing-remitting MS are recruited to participate in the clinical trial and are provided informed consent describing risks and potential befits of participation. The MS patients are randomized to treatment with a dose level of IRX4204EE, in the range of 1 to 40 mg/day administered orally, and a dose level of thyroxine (12.5 µg/day to 250 µg/day orally) or matching placebo, for 24 months. The primary clinical efficacy outcome measure is the EDSS, a 10 point scale which quantitates the MS patients' levels of disability by evaluating physical activities of daily life, such as walking, swallowing, bowel and bladder function, etc. The clinical trial uses a sample size selected to demonstrate to a statistically significant level, a difference in change in the mean EDSS over time, of a least 1 point, between the IRX4204EE/thyroxine-treated group, and the placebo-treated group, at the end of 24 months of treatment. In addition, in this clinical trial visual acuity testing is performed to quantitate effects of IRX4204EE/thyroxine on myelin damage and repair in the optic nerves. A sample size is selected which will demonstrate to a statistically level, a difference in change in visual acuity over time, of a least 1 line on the standard visual acuity chart, between the IRX4204EE/thyroxine-treated group, and the placebo-treated group, at the end of 24 months of treatment.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of providing IRX4204 to a patient in need thereof, comprising administering to the patient an ethyl ester of IRX4204, wherein IRX4204 has the structure

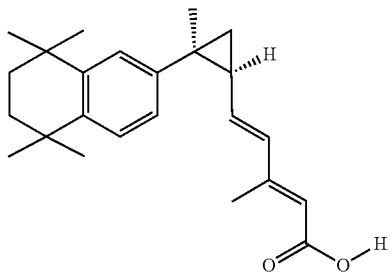 [SMILES: CC(/C=C/[C@@H]1C[C@]1(C)c1ccc2c(c1)C(C)(C)CCC2(C)C)=C\C(=O)O]

wherein an effective dose of the IRX4204 ethyl ester is lower than a corresponding effective dose of IRX4204 in treating a nervous system disorder, wherein the nervous system disorder is selected from Parkinson's disease, multiple sclerosis, Alzheimer's disease, amyotrophic lateral sclerosis, and aging-related neurodegeneration.

2. A method of providing IRX4204 to a patient in need thereof, comprising administering to the patient an ethyl ester of IRX4204, wherein the dose of the IRX4204 ethyl ester is greater than a toxicity producing dose of IRX4204 in treating a nervous system disorder, wherein the nervous system disorder is selected from Parkinson's disease, multiple sclerosis, Alzheimer's disease, amyotrophic lateral sclerosis, and aging-related neurodegeneration.

3. A method of providing IRX4204 to a patient in need thereof, comprising administering to the patient an ethyl ester of IRX4204, wherein Cmax of the active species is less than would result from administration of a same dose of IRX4204 in treating a nervous system disorder, wherein the nervous system disorder is selected from Parkinson's disease, multiple sclerosis, Alzheimer's disease, amyotrophic lateral sclerosis, and aging-related neurodegeneration.

4. A method of providing IRX4204 to a patient in need thereof, comprising administering an ethyl ester of IRX4204 to the patient, wherein Tmax of the active species is greater than would result from administration of a same dose of IRX4204 in treating a nervous system disorder, wherein the nervous system disorder is selected from Parkinson's disease, multiple sclerosis, Alzheimer's disease, amyotrophic lateral sclerosis, and aging-related neurodegeneration.

5. The method of claim 4, wherein Tmax is determined in the plasma.

6. The method according to claim 1, wherein target tissue penetration by the ester is greater than by a same dose of IRX4204.

7. The method according to claim 1, wherein the doses of IRX4204 and the IRX4204 ethyl ester are compared on a mass basis.

8. The method according to claim 1, wherein the doses of IRX4204 and the IRX4204 ethyl ester are compared on a molar basis.

9. The method of claim 1, wherein the IRX4204 ethyl ester is administered at a dosage that produces a systemic concentration of IRX4204≥50 pM.

10. The method of claim 1, wherein the IRX4204 ethyl ester is administered at a dosage that produces a systemic concentration of IRX4204≥0.1 nM.

11. The method of claim 1, wherein the IRX4204 ethyl ester is administered at a dosage that produces a systemic concentration of IRX4204≥1 nM.

12. The method of claim 1, wherein the IRX4204 ethyl ester is administered at a dosage that produces a concentration of IRX4204≥50 pM in a target tissue.

13. The method of claim 1, wherein the IRX4204 ethyl ester is administered at a dosage that produces a concentration of IRX4204≥0.1 nM in a target tissue.

14. The method of claim 1, wherein the IRX4204 ethyl ester is administered at a dosage that produces a concentration of IRX4204≥1 nM in a target tissue.

15. The method of claim 1, wherein the IRX4204 ethyl ester is administered at a dosage that produces a systemic concentration of IRX4204 that does not exceed 200 nM.

16. The method of claim 15, wherein the IRX4204 ethyl ester is administered nasally.

17. The method of claim 15, wherein the IRX4204 ethyl ester is administered orally.

18. The method of claim 17, wherein the dosage is up to 24, 40, 60, 80, 100, or 120 mg/m$^2$/day.

19. The method of claim 18, wherein the dosage exceeds 20 mg/m$^2$/day.

20. The method according to claim 1, further comprising administration of a neurotrophic factor or a mimetic thereof.

21. The method of claim 20, wherein the neurotrophic factor is brain-derived neurotrophic factor (BDNF), glial-derived neurotrophic factor (GDNF), nerve growth factor (NGF), neurotrophin-3 (NT-3), basic fibroblast growth factor (bFGF), ciliary neurotrophic factor (CNTF), neurotrophic factors-4/5 (NT-4/5), insulin-like growth factor (IGF), or insulin, or a mimetic thereof.

22. The method according to claim 1, further comprising administration of a therapeutically effective amount of thyroid hormone.

23. The method according to claim 21, further comprising administration of a therapeutically effective amount of thyroid hormone.

* * * * *